(12) United States Patent
Chao et al.

(10) Patent No.: US 9,512,086 B2
(45) Date of Patent: Dec. 6, 2016

(54) COMPOUND FOR PROMOTING APOPTOSIS OF CANCER CELLS AND A PHARMACEUTICAL COMPOSITION CONTAINING THE SAME AND USES THEREOF

(71) Applicant: National Chiao Tung University, Hsinchu (TW)

(72) Inventors: Jui-I Chao, Hsinchu (TW); Su-Pei Wang, Hsinchu (TW); Chinpiao Chen, Hsinchu (TW); Kai-Hao Yin, Hsinchu (TW); Jinn-Moon Yang, Hsinchu (TW); Ya-Hui Wu, Hsinchu (TW)

(73) Assignee: National Chiao Tung University, Hsinchu (TW)

( * ) Notice: Subject to any disclaimer, the term of this patent is extended or adjusted under 35 U.S.C. 154(b) by 0 days.

(21) Appl. No.: 14/596,495

(22) Filed: Jan. 14, 2015

(65) Prior Publication Data
US 2016/0068495 A1 Mar. 10, 2016

(30) Foreign Application Priority Data
Sep. 5, 2014 (TW) ............... 103130727 A

(51) Int. Cl.
*A61K 31/496* (2006.01)
*C07D 239/94* (2006.01)
*A61K 31/517* (2006.01)

(52) U.S. Cl.
CPC ........... *C07D 239/94* (2013.01); *A61K 31/496* (2013.01); *A61K 31/517* (2013.01)

(58) Field of Classification Search
CPC . C07D 239/94; A61K 31/496; A61K 31/517
USPC .................. 514/252.1, 252.17; 544/283, 359
See application file for complete search history.

(56) References Cited

U.S. PATENT DOCUMENTS 5,770,599 A * 6/1998 Gibson ............... C07D 403/12
514/228.2

OTHER PUBLICATIONS

Yin et al, "Bioorganic & Medicinal Chem Letters," 2014.*

*Primary Examiner* — Kamal Saeed
*Assistant Examiner* — Janet L Coppins
(74) *Attorney, Agent, or Firm* — McCarter & English, LLP; Yu Lu

(57) ABSTRACT

The present invention provides a compound of Formula (I) and a salt thereof,

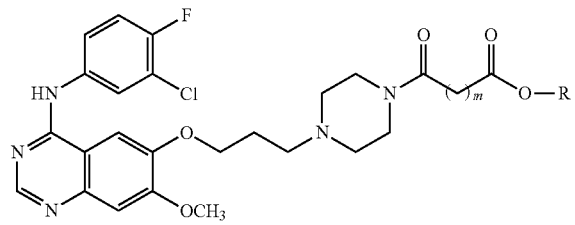

(I)

wherein, m is an integer of 2 to 7, and R is independently at least one selected from the group consisting of hydrogen and $C_1$-$C_{20}$ alkyl. The compound promotes apoptosis in cancer cell and inhibits its growth. The present invention also provides a pharmaceutical composition which comprises the compound of Formula (I), a salt thereof and a pharmaceutically acceptable carrier. The present invention further provides a method for production of the pharmaceutical composition used for treating cancer.

6 Claims, 13 Drawing Sheets

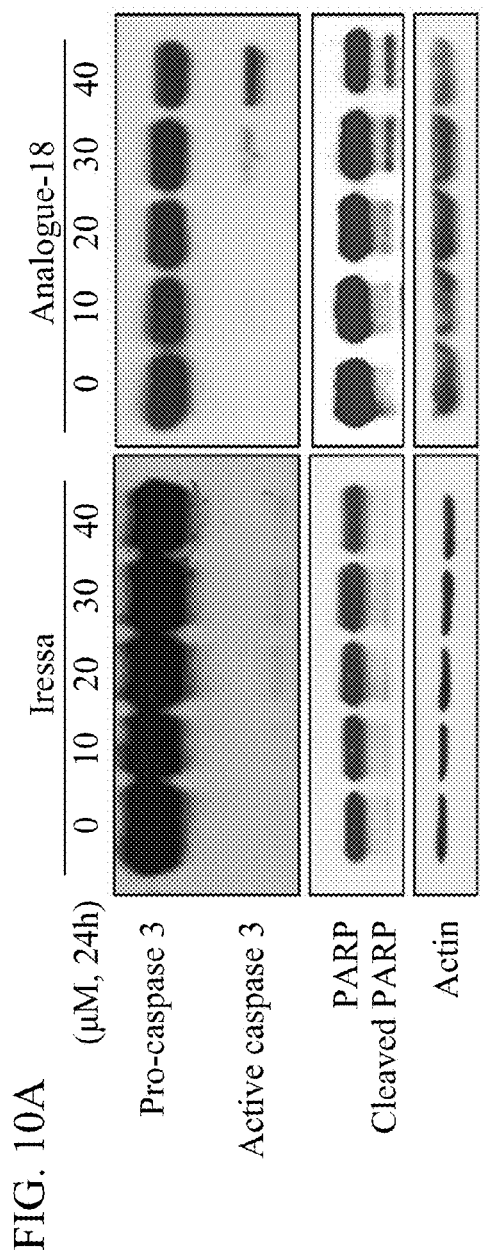
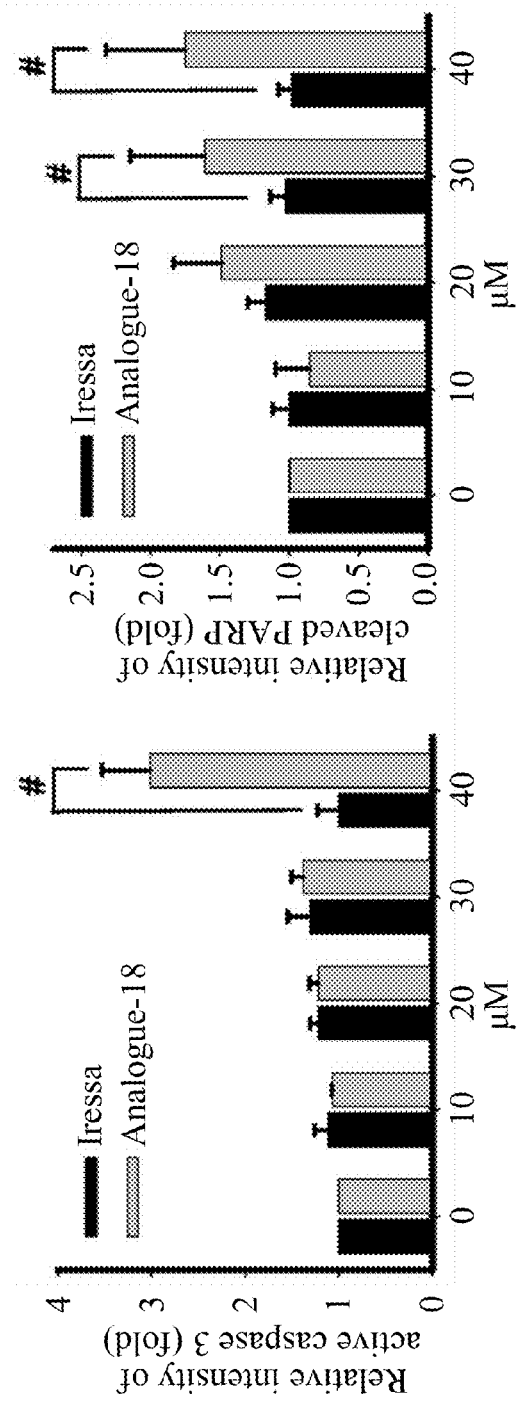
FIG. 10A
FIG. 10B
FIG. 10C

SEQUENCE LISTING

```
<160> NUMBER OF SEQ ID NOS: 4

<210> SEQ ID NO 1
<211> LENGTH: 21
<212> TYPE: DNA
<213> ORGANISM: Artificial sequence
<220> FEATURE:
<223> OTHER INFORMATION: Forward primer of survivin

<400> SEQUENCE: 1 ggcatgggtgccccgacgttg                                              21

<210> SEQ ID NO 2
<211> LENGTH: 21
<212> TYPE: DNA
<213> ORGANISM: Artificial sequence
<220> FEATURE:
<223> OTHER INFORMATION: Reverse primer of survivin

<400> SEQUENCE: 2 cagaggcctcaatccatggca                                              21

<210> SEQ ID NO 3
<211> LENGTH: 24
<212> TYPE: DNA
<213> ORGANISM: Artificial sequence
<220> FEATURE:
<223> OTHER INFORMATION: Forward primer of GAPDH

<400> SEQUENCE: 3 cggagtcaacggatttggtcgtat                                           24

<210> SEQ ID NO 4
<211> LENGTH: 24
<212> TYPE: DNA
<213> ORGANISM: Artificial sequence
<220> FEATURE:
<223> OTHER INFORMATION: Reverse primer of GAPDH

<400> SEQUENCE: 4 agccttctccatggtggtgaagac                                           24
```

COMPOUND FOR PROMOTING APOPTOSIS OF CANCER CELLS AND A PHARMACEUTICAL COMPOSITION CONTAINING THE SAME AND USES THEREOF

CROSS-REFERENCE TO RELATED APPLICATION

This application claims foreign priority under 35 U.S.C. §119(a) to Patent Application No. 103130727, filed on Sep. 5, 2014, in the Intellectual Property Office of Ministry of Economic Affairs, Republic of China (Taiwan, R.O.C.), the entire content of which patent application is incorporated herein by reference.

BACKGROUND OF THE INVENTION

1. Field of the Invention

This invention relates to a new compound, more particularly, to a compound for inhibiting growths of cancer cells and promoting apoptosis of the cancer cells.

2. Description of Related Art

Lung cancer has become one of the leading causes of cancer-related morbidity and mortality in the world. According to statistics, lung cancer is the most common cause of death of cancer in Taiwan. Lung cancer can be mainly divided into a small cell lung carcinoma (hereinafter referred to SCLC) and a non-small cell lung carcinoma (hereinafter referred to NSCLC). Among these, NSCLC takes about 80% of the lung cancer cases and SCLC takes about 20%. Most of the NSCLC patients were observed an overexpression of epidermal growth factor receptor (hereinafter referred to EGFR). Therefore, EGFR which has a mutation with abnormal overexpression becomes one of the target proteins for new drugs.

Irresa, also known as Gefitinib or ZD1839, is a small molecule tyrosine kinase inhibitor (TKI) and has been approved for clinical treatment of NSCLC. Irresa competes with the binding of ATP to the substrate binding site of the intracellular tyrosine kinase domain of EGFR; thereby inhibit tyrosine kinase autophosphorylation and block downstream signal transduction.

The anticancer activities of Irresa are related to the mutation of EGFR. For example, the deletions in exon 19 and the substitution of an arginine for leucine at codon 858 (L858R) in exon 21 are the most common EGFR activating mutations, which increase the sensitivity of Irresa in tumors. The resistances of Irresa in lung cancer therapy have been reported in several studies and the other secondary EGFR mutations have been found to associate with acquired resistance. Based on clinical data, about 50% of NSCLC patients having resistances to Irresa have a mutation at position 790 of the amino acid sequence of EGFR, T790M (from a threonine to a methionine). T790M mutation is located in the ATP-binding site of EGFR structure and blocks EGFR-TKI binding. Moreover, T790M also can increase the affinity of ATP binding to the cleft to enhance the activity of EGFR.

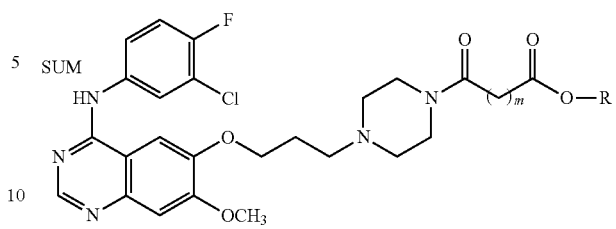

Formula (I) and a salt thereof,
wherein, m is an integer of 2 to 7, and R is independently at least one selected from the group consisting of hydrogen and $C_1$-$C_{20}$ alkyl.

In an embodiment of the present invention, m is 2 and R is $C_1$-$C_{13}$ alkyl.

In an embodiment of the present invention, m is 2 and R is $C_{12}$ alkyl.

In an embodiment of the present invention, the compound of the present invention is used to promote an apoptosis in cancer cell and inhibit a growth of the cancer cell. Preferably, the cancer cell is at least one selected from the group consisting of lung cancer cell, rectal cancer cell and bladder cancer cell.

In an embodiment of the present invention, the compound of Formula (I) of the present invention is used to suppress an activity of epidermal growth factor receptor (hereinafter referred to EGFR) protein kinase, so as to promote an apoptosis in the cancer cell.

This invention further provides a pharmaceutical composition comprising the compound of Formula (I) or a salt thereof and a pharmaceutically acceptable carrier.

This invention further provides a method for treating a cancer in a subject, comprising a step of administrating an effective amount of the pharmaceutical composition of the present invention to the subject wherein the cancer is at least one selected from the group consisting of lung cancer, rectal cancer and bladder cancer.

BRIEF DESCRIPTION OF THE DRAWINGS

FIG. 1A shows RKO human rectal cancer cell line, hereinafter referred to "RKO cells," group. FIG. 1B shows BFTC905 human bladder cancer cell line, hereinafter referred to "BFTC905," group.

FIG. 2A shows A549 human lung adenocarcinoma cell line, hereinafter referred to "A549 cells. " FIG. 2B shows H1299 human non-small cell lung cell line, hereinafter referred to "H1299 cells. " FIG. 2C shows CL3 human lung cancer cell line, hereinafter referred to "CL3 cells." The results of FIGS. 2A-2C were obtained from 3 experiments and the bar represents the mean±S.E. ##p<0.01 indicates significant differences between the sample treated with Irresa and the one treated with Analogue-18. FIG. 2D shows HFL1 human normal lung fibroblast cell line, hereinafter referred to "HFL1 cells." The results of FIG. 2D were obtained from 6 experiments and the bar represents the mean±S.E.

FIG. 4A shows the standard curve for conversion of ATP to ADP, which is positively related to ADP amount. FIG. 4B shows the luminescence intensities quantified by IVIS system. FIG. 4C shows the kinase specific activity calculated by using standard conversion curve from FIG. 4A. FIG. 4D shows the EGFR kinase activity expressed as percent of the maximal enzyme activity, wherein the specific activity of kinase in the absence of Irresa or Analogue-18 is taken as 100%. The results of FIGS. 4A-4D were obtained from 3 experiments and the bar represents the mean±S.E. *$p<0.05$ and **$p<0.01$ indicate significant differences between the control (without any compound) and the sample treated with Irresa or Analogue-18.

FIGS. 10A-10C show that Analogue-18 is more effective in inducing protein expression of caspase 3 and poly ADP ribose polymerase (hereinafter referred to PARP) than Irresa in human lung cancer cells. (FIG. 10A) A549 cells were treated with 0 to 40 μM Analogue-18 or Irresa for 24 hours. The total protein extracts were subjected to Western blot analysis using specific antibodies for caspase 3, PARP and actin. The actin was used as an internal protein control group. Representative Western blot results were shown from one of three independent experiments with similar findings. In FIGS. 10B and 10C, the relative protein intensity of active caspase 3 and cleaved-PARP was obtained from Western analysis by semi-quantification. The results were obtained from 3 experiments and the bar represents the mean±S.E. *$p<0.05$ indicates significant difference between the control (without any compound) and the sample treated with Analogue-18.

(FIG. 11A) A549 cells were treated with 0 to 40 μM Analogue-18 or Irresa for 24 hours. The total RNA was extracted from A549 cells according to the manufacturer's protocol. The mRNA expression was analyzed by semi-quantitative reverse transcription polymerase chain reaction (hereinafter referred to RT-PCR). GAPDH was the internal control. Representative RT-PCR results were shown from one of three independent experiments with similar findings. (FIG. 11B) The bar represents the mean±S.E. #$p<0.05$ indicates significant difference between the samples treated with Irresa and those treated with Analogue-18. (FIG. 11C) A549 cells were treated with 0 to 40 μM Irresa or Analogue-18 for 24 hours. The total protein extracts were subjected to Western blot analysis using specific antibodies for surviving and actin. Representative Western blot results were shown from one of three independent experiments with similar findings. (FIG. 11D) The relative protein intensity of surviving was from Western analysis by semi-quantification. The results were obtained from three experiments. The bar represents the mean±S.E. *$p<0.05$ indicates significant difference between the control (without any compound) and the samples treated with Irresa or Analogue-18. #$p<0.05$ indicates significant difference between the samples treated with Irresa and those treated with Analogue-18.

(FIG. 12A) The total protein extracts were subjected to Western blot analysis. (FIG. 12B) After transfection and treatment with Analogue-18, the cell viability was measured by MTT assay. The results were obtained from three experiments and the bar represents the mean±S.E. **$p<0.01$ indicates significant difference between the transfection of the control and surviving vector or those treated with Analogue-18. ##$p<0.01$ indicates significant difference between the control and surviving vector by the samples treated with Analogue-18.

(FIG. 13A) The tumor volume was measured every four days. The results were obtained from 8 nude mice and the bar represents the mean±S.E. ***$p<0.001$ indicates significant difference between the control (without treating any compound) and the samples treated with Analogue-18. (FIG. 13B) Tumors were harvested from scarified nude mice after drug treatment at day 16. (FIG. 13C) The xenograft tumor tissues from each group were homogenized and the total lysates were subjected to Western blot analysis using specific antibodies for surviving and actin. Representative Western blot results were shown from one of three independent experiments with similar findings. The relative protein intensity of surviving was from Western analysis by semi-quantification. The results were obtained from three experiments.

DETAILED DESCRIPTION OF THE INVENTION

Figure 1A:
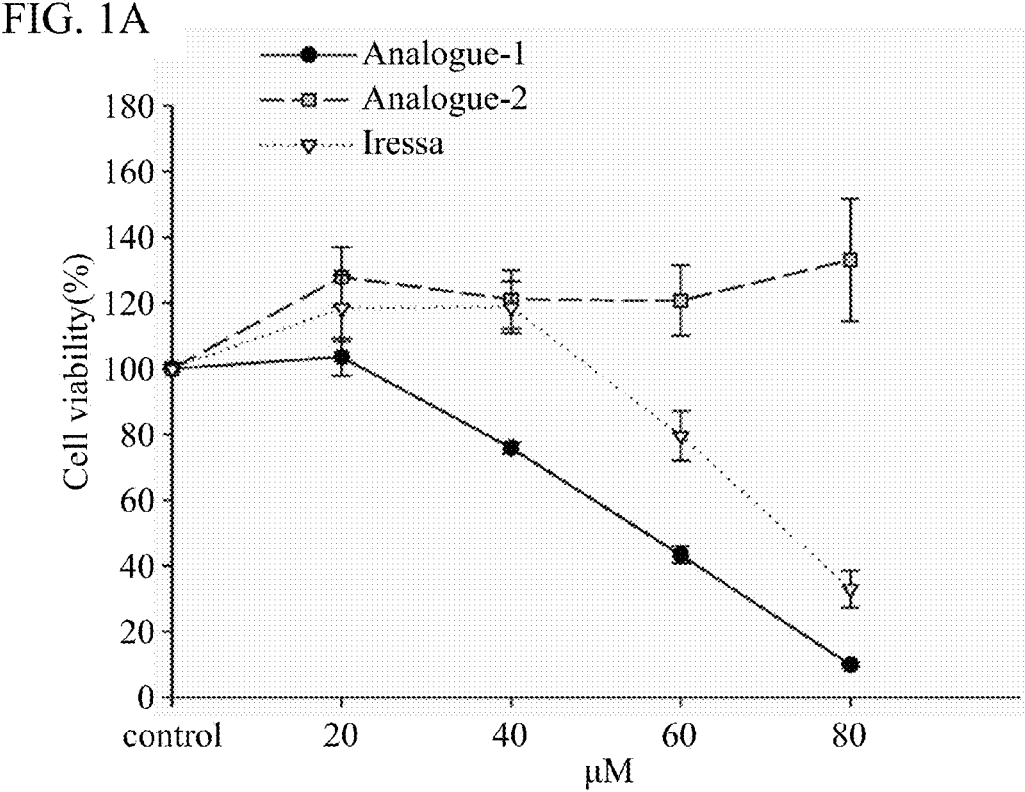
FIGS. 1A-1B show the cell viability results for treating different cancer cell lines respectively with different concentrations of Irresa-Analogue (hereinafter referred to "Analogue")-1, Analogue-2 and Irresa for 24 hours.

A detailed description of this invention is illustrated by the following specific embodiments. Person skilled in the art can conceive other advantages and effects of this invention based on the disclosure contained in the specification of this invention. This invention can be executed or applied by the other methods. Without affecting the purpose of this invention, any detail in the description can be modified or changed based on different viewpoints and applications and it shall still be covered within the scope of this invention.

This invention provides a compound of Formula (I) and a salt thereof,

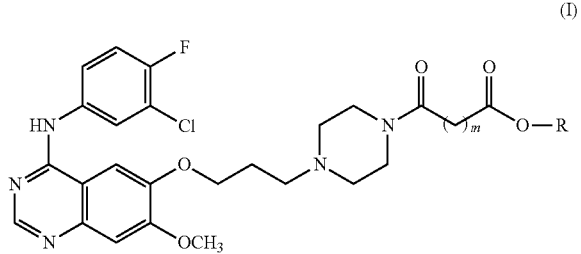

(I)

wherein, m is an integer of 2 to 7, and R is independently at least one selected from the group consisting of hydrogen and $C_1$-$C_{20}$ alkyl.

In an embodiment of the present invention, preferably, m is 2 and R is $C_1$-$C_{20}$ alkyl. The most preferably, m is 2 and R is $C_{12}$ alkyl.

In an embodiment of the present invention, the compound is dodecyl-4-(4-(3-(4-(3-chloro-4-fluorophenylamino)-7-methoxyquinazolin-6-yloxy)propyl)piperazin-1-yl)-4-oxobutanoate (i.e., Analogue-18).

In an embodiment of the present invention, the compound is used to promote an apoptosis in a cancer cell and inhibits a growth of the cancer cell. The cancer cell is preferably at least one selected from the group consisting of a lung cancer cell, a rectal cancer cell and a bladder cancer cell.

In an embodiment of the present invention, the compound of Formula (I) is used to suppress the activity of EGFR protein kinase, so as to promote an apoptosis in the cancer cell.

In an embodiment of the present invention, the compound is used to promote the activation of caspase 3, for the cleavage of PARP, and to suppress protein and gene expression of surviving in cancer cell, so as to promote an apoptosis in cancer cell.

The present invention further provides a pharmaceutical composition comprising the compound of Formula (I), a salt thereof and a pharmaceutically acceptable carrier.

The compound of the present invention has low toxicity and may be mixed with a pharmaceutically acceptable carrier to form a pharmaceutical composition for mammals, such as human, mice, rat, rabbit, dog, cat, cattle, horse, pig and monkey.

The pharmaceutically acceptable carrier that may be used to produce the pharmaceutical composition of the present invention includes various organic or inorganic carrier substances in common use as pharmaceutical materials, including excipients, lubricants, binders, disintegrants, water-soluble polymers and basic inorganic salts for solid preparations; and solvents, solubilizing agents, suspending agents, isotonizing agents, buffers and soothing agents for liquid preparations. Other ordinary pharmaceutical additives such as preservatives, antioxidants, colorants, sweetening agents, and the like may also be used as necessary.

Examples of the dosage form of the pharmaceutical composition include oral preparation, such as tablet including dragee, film coated tablet, sublingual tablet and orally disintegrating tablet, capsule including soft capsule and microcapsule, granule, powder, opiate, syrup, emulsion, suspension, film, such as orally disintegrating film, and their analogues; parenteral agent, such as injection fluid (for example, subcutaneous injection fluid, intravenous injection fluid, intraperitoneal injection fluid and drip injection fluid), pill, nasal preparation, lung preparation, or inhalant, and their analogues. This invention further provides a method for treating a cancer in a subject, comprising a step of administrating an effective amount of the pharmaceutical composition of the present invention to the subject, wherein the cancer is at least one selected from the group consisting of lung cancer, rectal cancer and bladder cancer.

The term "Iressa" indicates a trade name of a drug for treating lung cancer and its scientific name is Gefitinib. Iressa is an inhibitor of EGFR.

In the specification of the present invention, the term "Analogue" indicates a series of piperazine analogues of Gefitinib, wherein the morpholino group of Gefitinib is substituted by various piperazine.

EXAMPLES

Cell Lines and Cell Culture

RKO cell line is a human rectal cancer cell line. BFTC905 cell line is a human bladder cancer cell line. A549 cell line (ATCC number: CCL-185) was derived from lung adenocarcinoma of a 58-year-old Caucasian male that contained the wild type p53. H1299 cell line is a human NSCLC cell line (p53 null). CL3 cell line was derived from lung cancer kindly provided by Dr. Pan-Chyr Yang (National Taiwan University). HFL1 cell (ATCC number: CCL-153) is normal lung fibroblast derived from a Caucasian fetus. A431 cell line (EGFR overexpressed) was an epidermoid carcinoma cell line derived from an 85-year-old female. BFTC905, A549, H1299 and CL3 cell lines were cultured in RPMI-1640 medium (Gibco, Life Technologies, Grand Island, N.Y., USA). RKI cells, HFL1 cells and A431 cells were cultured in DMEM medium (Gibco, Life Technologies, Grand Island, N.Y., USA). The complete medium was supplemented with 10% fetal bovine serum (hereinafter referred to FBS), 100 units/ml penicillin, 100 μg/ml streptomycin and sodium bicarbonate. These cells were maintained at 37° C. and 5% $CO_2$ in a humidified incubator (310/Thermo, Forma Scientific, Inc., Marietta, Ohio).

Statistical Analysis

Each experiment was repeated at least three times. Data were analyzed using Student's t test or analysis of variance (a comparison of multiple groups), and a p value of <0.05 was considered statistically significant in each experiment.

Example 1

Synthesis of Irresa Analogues

1. Synthesis of Irresa Analogue (Hereinafter Referred to Analogue)-1 and Analogue-2

(1). Compound-1: 4-methoxy-4-oxobutanoic acid (step 1)

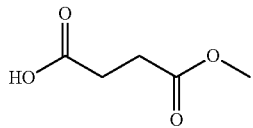

A mixture of succinic anhydride (1.00 g, 10.00 mmol) and dry methanol (20 mL, 500 mmol) was stirred vigorously while heated at reflux 2.5 hours. The excess of methanol was removed under reduced pressure and the residue was taken up in water, and the solution was extracted with dichloromethane (hereinafter referred to DCM), dried over $MgSO_4$, and evaporated to obtain Compound-1 (0.90 g, 6.81 mmol) in 68% yield.

$^1$H NMR (400 MHz, $CDCl_3$, δ): 10.89 (b, 1H), 3.70 (s, 3H), 2.71-2.61 (m, 4H); $^{13}$C NMR (100.6 MHz, $CDCl_3$, δ): 178.1, 172.6, 51.9, 28.8, 28.6; IR (KBr): 3028, 2957, 1736, 1690, 1175, 1003 cm$^{-1}$; MS m/z: 132.0 (M$^+$, 0.1), 114.1 (11.2), 101.0 (100.0), 73.1 (20.9), 59.1 (17.2), 55.0 (41.8); HRMS-EI (m/z): [M]$^+$ calculated for $C_5H_8O_4$, 132.0423. found, 132.0424.

(2). Compound-2: methyl 4-(4-benzylpiperazin-1-yl)-4-oxobutanoate (step 2)

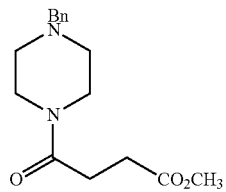 [SMILES: COC(=O)CCC(=O)N1CCN(Cc2ccccc2)CC1]

A solution of Compound-1 (0.35 g, 2.65 mmol) and thionyl chloride (0.22 mL, 2.9 mmol) in benzene (5 mL) was refluxed for 1.5 hours. Subsequently, the majority of the thionyl chloride and benzene were removed by distillation. The mixture was cooled down to room temperature and dried under a vacuum to give a crude 3-chlorocarbonyl-propionic acid methyl ester. A solution of 3-chlorocarbonyl-propionic acid methyl ester (0.5 g, 2 mmol) in dichloromethane (5 mL) was added to a round flask containing 1-benzylpiperazin (0.50 g, 2.84 mmol) in dichloromethane through cannula, and subsequently pyridine (0.65 mL, 8.00 mmol) was added. The resulting solution was stirred at room temperature overnight, and quenched by adding water. The pH of the solution was made basic (pH 9), by adding 2 M NaOH solution. The solution was extracted with dichloromethane, dried over $MgSO_4$, and evaporated to give a crude residue which was purified by column chromatography, eluting by ethyl acetate/hexane (1:2.3, 1:1, 3:1) to provide Compound-2 (0.26 g, 0.90 mmol) in 34% yield.

$^1$H NMR (400 MHz, $CDCl_3$, δ): 7.32-7.29 (m, 4H), 7.28-7.27 (m, 1H), 3.69 (s, 3H), 3.63-3.60 (t, J=5.1 Hz, 2H), 3.51 (s, 2H), 3.49-3.47 (t, J=5.1 Hz, 2H), 2.68-2.59 (m, 4H), 2.45-2.39 (m, 4H); $^{13}$C NMR (100.6 MHz, $CDCl_3$, δ): 173.7, 169.5, 137.6, 129.1, 128.3, 127.3, 62.9, 52.9, 52.7, 51.8, 45.3, 41.8, 29.1, 27.9; IR (KBr): 2949, 1736, 1646, 1438, 1226, 1165, 998, 744 cm$^{-1}$; MS m/z: 290.1 (M$^+$, 14.0), 259.1 (16.4), 146.1 (48.7), 134.1 (21.5), 91.1 (100.0); HRMS-EI (m/z): [M]$^+$ calculated for $C_{16}H_{22}N_2O_3$, 290.1630. found, 290.1634.

(3). Compound-3: methyl 4-(4-(3-chloropropyl)piperazin-1-yl)-4-oxobutanoate (step 3)

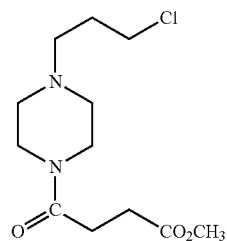 [SMILES: COC(=O)CCC(=O)N1CCN(CCCCl)CC1]

A mixture of Compound 2 (0.21 g, 0.72 mmol) and 10% palladium on carbon (Pd/C) (22 mg, 10 wt %) in methanol (20 mL) in a Parr glass vessel and carefully flushed three times with hydrogen gas. The vessel was finally charged with hydrogen gas (60 psi) and shaken mechanically for 12 hours. After completion of the reaction, the reaction mixture was filtered through a pad of celite and washed with excess methanol. The filtrate was concentrated under reduced pressure to obtain 4-oxo-4-piperazin-1-yl-butyric acid methyl ester (0.095 g, 0.48 mmol) in 66% yield. 4-oxo-4-piperazin-1-yl-butyric acid methyl ester was dissolved in tetrahydrofuran (hereinafter referred to THF) (10 mL), and subsequently added triethylamine (0.08 mL, 0.57 mmol) and 1-bromo-3-chloropropane (0.057 mL, 0.57 mmol). The solution was stirred at room temperature overnight. The reaction mixture was quenched by adding water. The resulting solution was extracted with ethyl acetate, dried over $MgSO_4$, and evaporated to give a residue purified by column chromatography ($Al_2O_3$), eluting by ethyl acetate to provide Compound-3 (0.024 g, 0.087 mmol) in 18% yield.

$^1$H NMR (400 MHz, $CDCl_3$, δ): 3.67 (s, 3H), 3.60-3.57 (t, J=6.3 Hz, 4H), 3.48-3.45 (t, J=5.1 Hz, 2H), 2.66-2.58 (m, 4H), 2.49-2.46 (t, J=7.1 Hz, 2H), 2.43-2.41 (t, J=5.0 Hz, 2H), 2.39-2.36 (t, J=5.1 Hz, 2H), 1.95-1.88 (m, 2H); $^{13}$C NMR (100.6 MHz, $CDCl_3$, δ): 173.6, 169.5, 55.1, 53.3, 52.8, 51.8, 45.2, 43.0, 41.7, 29.7, 29.0, 27.9; IR (KBr): 2950, 2814, 1736, 1647, 1438, 1369, 1227, 1168 cm$^{-1}$; MS m/z: 276.1 (M$^+$, 8.6), 245.1 (28.2), 213.1 (100.0), 132.1 (15.4); HRMS-EI (m/z): [M]$^+$ calculated for $C_{12}H_{21}ClN_2O_3$, 276.1241. found, 276.1242.

(4). Compound 4: 4-(3-chloro-4-fluorophenylamino)-7-methoxyquinazolin-6-ol (step 4)

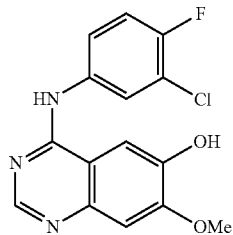 [SMILES: COc1cc2ncnc(Nc3ccc(F)c(Cl)c3)c2cc1O]

A mixture of 6-(benzyloxy)-N-(3-chloro-4-fluorophenyl)-7-methoxyquinazolin-4-amine (0.15 g, 0.37 mmol) and 10% Pd/C (25 mg, 10 wt %) in methanol (20 mL) in a Parr glass vessel and carefully flushed three times with hydrogen gas. The vessel was finally charged with hydrogen gas (60 psi) and shaken mechanically for 24 hours. After completion of the reaction, the reaction mixture was filtered through a pad of celite and washed with excess methanol. The filtrate was concentrated under reduced pressure to obtain Compound-4 (96 mg, 0.3 mmol) in 82% yield.

(5). Analogue-1: methyl 4-(4-(3-(4-(3-chloro-4-fluorophenylamino)-7-methoxyquinazolin-6-yloxy)propyl)piperazin-1-yl)-4-oxobutanoate (step 5)

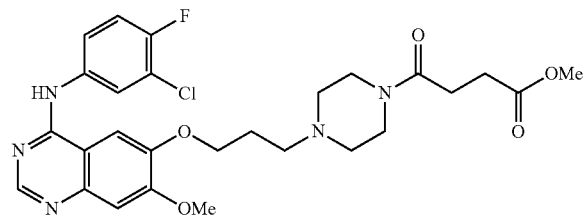 [SMILES: COC(=O)CCC(=O)N1CCN(CCCOc2cc3c(Nc4ccc(F)c(Cl)c4)ncnc3cc2OC)CC1]

Compound-4 (20 mg, 0.063 mmol) was dissolved in N,N-dimethylformamide (hereinafter referred to DMF) (0.4 mL), potassium carbonate (17 mg, 0.125 mmol) and Compound 3 (17 mg, 0.063 mmol) were added and heated at 90° C. overnight. The reaction mixture was then cooled to room temperature and quenched by addition of water. The resulting solution was extracted with ethyl acetate, dried over MgSO$_4$, and concentrated to give a residue which was purified with column chromatography, eluting by ethyl acetate to provide Analogue-1 (0.023 g, 0.041 mmol) in 57% yield.

$^1$H NMR (400 MHz, CDCl$_3$, δ): 8.65 (s, 1H), 7.89-7.86 (dd, J=6.4, 2.5 Hz, 1H), 7.74 (b, 1H), 7.56-7.53 (m, 1H), 7.24-7.23 (m, 2H), 7.20-7.06 (m, 1H), 4.18-4.15 (t, J=6.5 Hz, 2H), 3.97 (s, 3H), 3.68 (s, 3H), 3.63 (b, 2H), 3.51 (b, 2H), 3.66-2.59 (m, 6H), 2.51 (b, 2H), 2.46 (b, 2H), 2.12-2.07 (m, 4H); $^{13}$C NMR (100.6 MHz, CDCl$_3$, δ): 173.8, 169.6, 160.8, 158.4, 156.7, 155.1, 153.6, 148.9, 147.3, 134.6, 127.3, 124.2, 115.8, 115.6, 109.0, 107.7, 101.2, 67.4, 56.2, 54.7, 53.2, 52.7, 51.9, 45.1, 41.6, 29.7, 29.0, 27.9, 26.3; IR (KBr): 3322, 2949, 2893, 2838, 1747, 1644, 1633, 1579, 1502, 1472, 1433, 1220, 1172, 1005, 839 cm$^{-1}$; MS m/z: 559.2 (M$^+$, 2.9), 525.2 (20.1), 494.2 (23.1), 381.1 (21.0), 297.1 (28.2), 285.1 (32.3), 241.1 (28.5), 213.1 (100.0), 99.1 (33.2), 70.1 (29.7); HRMS-EI (m/z): [M]$^+$ calculated for C$_{27}$H$_{31}$ClFN$_5$O$_5$, 559.1998. found, 559.2007.

(6). Analogue-2: 4-(4-(3-(4-(3-chloro-4-fluorophenylamino)-7-methoxyquinazolin-6-yloxy)propyl)piperazin-1-yl)-4-oxobutanoic acid (step 6)

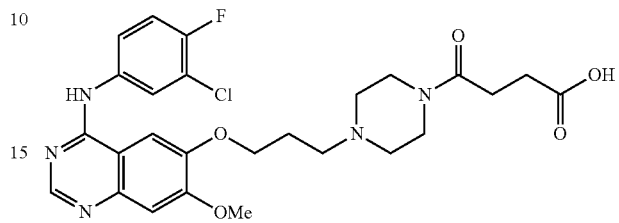

A solution of Analogue-1 (0.08 g, 0.143 mmol) and lithium hydroxide (9 mg, 0.214 mmol) in methanol (8 mL) was heated at 60° C. overnight. The reaction mixture was then cooled to room temperature and evaporated to give a crude product which was taken up in water, and the solution was extracted with ethyl acetate, dried over MgSO$_4$, and evaporated to obtain Analogue-2 (53 mg, 0.097 mmol) in 68% yield.

$^1$H NMR (400 MHz, MeOD, δ): 8.46 (s, 1H), 8.02-7.99 (dd, J=6.7, 2.4 Hz, 1H), 7.74 (s, 1H), 7.71-7.66 (m, 1H), 7.30-7.25 (t, J=8.9 Hz, 2H), 7.19-7.15 (m, 1H), 4.30-4.27 (t, J=5.9 Hz, 2H), 4.01 (s, 3H), 3.66-3.63 (t, J=4.9 Hz, 4H), 3.33-3.31 (m, 2H), 2.75-2.72 (t, J=7.2 Hz, 2H), 2.69-2.66 (m, 4H), 2.61-2.58 (m, 4H), 2.19-2.14 (m, 2H); $^{13}$C NMR (100.6 MHz, CDCl$_3$, δ): 174.4, 169.9, 156.5, 155.0, 154.8, 153.1, 152.4, 148.8, 147.5, 137.3, 124.0, 122.9, 122.8, 119.3, 119.1, 117.1, 116.9, 109.2, 107.8, 102.3, 67.6, 56.4, 54.9, 53.5, 53.1, 45.1, 41.6, 40.6, 29.5, 27.9, 26.6; IR (KBr): 3387, 2963, 2812, 1723, 1646, 1625, 1584, 1533, 1499, 1476, 1427, 1238, 854 cm$^{-1}$; MS m/z: 546.0 (M$^+$, 50.9), 512.0 (16.1), 389.0 (13.7), 320.0 (26.8), 307.0 (30.1), 227.0 (36.1), 199.0 (28.3), 154.0 (99.9), 136.0 (100.0), 90.0 (80.5), 78.0 (76.5); HRMS-FAB (m/z): [M+1]$^+$ calculated for C$_{26}$H$_{30}$ClFN$_5$O$_5$, 546.1920. found, 546.1930.

2. Synthesis of Analogue-3 to Analogue-7

(1). Compound-5: 1-(3-chloropropyl)-piperazine hydrocloride (step 7)

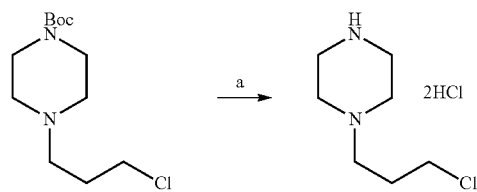 [SMILES: CC(C)(C)OC(=O)N1CCN(CCCCl)CC1 ; ClCCCN1CCNCC1]

1-(3-chloropropyl)-4-(t-butyloxycarbonyl)-piperaxine (4.0 g, 15.2 mmol) was treated with hydrochloric acid in ethyl acetate to obtain Compound-5 (3.17 g, 13.5 mmol) in yield 89%.

$^1$H NMR (400 MHz, D$_2$O, δ): 3.63-3.54 (m, 9H), 3.39 (s, 1H), 3.40-3.35 (m, 2H), 2.21-2.14 (m, 2H). $^{13}$C NMR (100.6 MHz, D$_2$O, δ): 54.8, 48.6, 41.1, 40.7, 26.2. IR (KBr): 3356, 3001, 1443, 1301, 1160, 1084 cm$^{-1}$ MS m/z: 162.1 (M$^+$, 13.6), 120.1 (100.0), 99.1 (79.5), 70.1 (29.2), 56.1 (49.6). HRMS-EI (m/z): [M]$^+$ calculated for, $C_7H_{15}ClN_2$, 162.0924. found, 162.0930.

(2). Compound-6 to Compound-10: (step 8)

A solution of monomethyl alkanoic acid (n=3 to 7) (1.2 eq) and thionyl chloride (1.4 eq) in benzene (5 mL) was refluxed for 3 hours. Subsequently, the majority of the thionyl chloride and benzene were removed by distillation. The mixture was cooled down to room temperature and dried under a vacuum to give a crude chlorocarbonyl-alkanoic acid methyl ester (n of the alkanoic acid=3-7). A solution of chlorocarbonyl-alkanonic acid methyl ester (n of the alkanoic acid=3-7) in 5 mL dichloromethane was added to a round flask containing Compound-5 (1 eq) by cannula, and subsequently added pyridine (3.5 eq). The resulting solution was stirred at room temperature overnight, and quenched by adding water. The solution was extracted with ethyl acetate, dried over MgSO$_4$, and evaporated to give a residue which was purified by column chromatography (Al$_2$O$_3$), eluting by ethyl acetate/hexane (1:15) to provide Compound-6 to Compound-10.

Compound-6: methyl 5-(4-(3-chloropropyl)piperazin-1-yl)-5-oxopentanoate

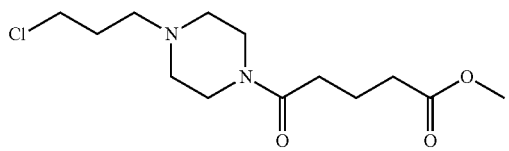 [SMILES: COC(=O)CCCC(=O)N1CCN(CCCCl)CC1]

Yield: 35%; $^1$H NMR (400 MHz, CDCl$_3$, δ): 3.65 (s, 3H), 3.60-3.57 (t, J=6.5 Hz, 4H), 3.46-3.43 (t, J=4.9 Hz, 2H), 2.49-2.46 (t, J=7.0 Hz, 2H), 2.46-2.33 (m, 8H), 1.96-1.92 (m, 4H); $^{13}$C NMR (100.6 MHz, CDCl$_3$, δ): 173.8, 170.6, 55.1, 53.4, 52.8, 51.5, 45.4, 43.0, 41.5, 33.2, 32.1, 30.0, 20.4; IR (KBr): 2923, 2853, 1735, 1647, 1457, 1373, 1105 cm$^{-1}$; MS m/z: 290.2 (M$^+$, 6.8), 259.2 (27.3), 227.2 (100.0), 132.1 (75.2), 99.1 (79.6), 70.1 (39.8), 55.1 (50.5); HRMS-EI (m/z): [M]$^+$ calculated for C$_{13}$H$_{23}$ClN$_2$O$_3$, 290.1397. found, 290.1391.

Compound-7: methyl 6-(4-(3-chloropropyl)piperazin-1-yl)-6-oxohexanoate

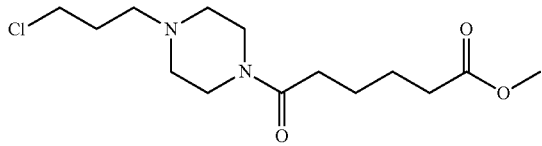 [SMILES: COC(=O)CCCCC(=O)N1CCN(CCCCl)CC1]

Yield: 56%; $^1$H NMR (400 MHz, CDCl$_3$, δ): 3.64 (s, 3H), 3.60-3.58 (t, J=6.4 Hz, 4H), 3.45-3.42 (t, J=4.9 Hz, 2H), 2.50-2.46 (t, J=7.0 Hz, 2H), 2.46-2.36 (m, 4H), 2.34-2.29 (m, 4H), 1.96-1.89 (m, 2H), 1.67-1.63 (m, 4H); $^{13}$C NMR (100.6 MHz, CDCl$_3$, δ): 173.9, 171.0, 55.1, 53.5, 52.8, 51.5, 45.5, 42.9, 41.5, 33.8, 32.8, 29.7, 24.7. IR (KBr): 2949, 1735, 1645, 1436, 1249, 1004 cm$^{-1}$; MS m/z: 304.2 (M$^+$, 6.2), 273.1 (25.1), 241.1 (100.0), 132.1 (96.0), 99.1 (41.7), 70.1 (27.8), 55.1 (55.6); HRMS-EI (m/z): [M]$^+$ calculated for C$_{14}$H$_{25}$ClN$_2$O$_3$, 304.1554. found, 304.1558.

Compound-8: methyl 7-(4-(3-chloropropyl)piperazin-1-yl)-7-oxoheptanoate

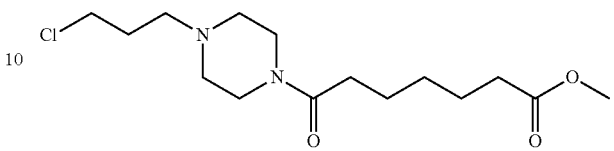

Yield: 60%; $^1$H NMR (400 MHz, CDCl$_3$, δ): 3.64 (s, 3H), 3.60-3.57 (t, J=6.3 Hz, 4H), 3.44-3.42 (t, J=4.6 Hz, 2H), 2.50-2.46 (t, J=6.9 Hz, 2H), 2.38-2.36 (m, 4H), 2.31-2.27 (m, 4H), 1.95-1.89 (m, 2H), 1.67-1.61 (m, 4H), 1.38-1.30 (m, 2H); $^{13}$C NMR (100.6 MHz, CDCl$_3$, δ): 174.1, 171.3, 55.1, 53.5, 52.8, 51.5, 45.5, 43.0, 41.5, 33.9, 33.0, 29.7, 28.9, 24.9, 24.7; IR (KBr): 2947, 1736, 1644, 1435, 1174, 1004 cm$^{-1}$. MS m/z: 318.2 (M$^+$, 4.5), 287.2 (22.4), 255.2 (100.0), 132.1 (90.2), 99.1 (70.5), 70.1 (23.7), 55.1 (27.9; HRMS-EI (m/z): [M]$^+$ calcd for C$_{15}$H$_{27}$ClN$_2$O$_3$, 318.1710. found, 318.1718.

Compound-9: methyl 8-(4-(3-chloropropyl)piperazin-1-yl)-8-oxooctanoate

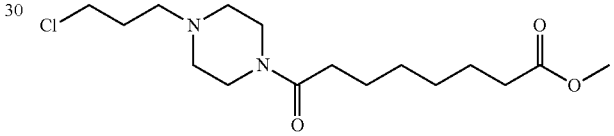

Yield: 67%; $^1$H NMR (400 MHz, CDCl$_3$, δ): 3.61 (s, 3H), 3.61-3.57 (m, 4H), 3.42-3.40 (t, J=4.9 Hz, 2H), 2.47-2.43 (m, 2H), 2.39-2.33 (m, 4H), 2.27-2.23 (t, J=7.5 Hz, 2H), 1.93-1.87 (m, 4H), 1.59-1.54 (m, 4H), 1.30-1.29 (b, 4H); $^{13}$C NMR (100.6 MHz, CDCl$_3$, δ): 174.1, 171.4, 55.1, 53.5, 52.8, 51.4, 45.5, 43.0, 41.4, 33.9, 33.0, 29.7, 29.0, 28.9, 25.0, 24.7; IR (KBr): 2934, 2858, 1737, 1645, 1462, 1435, 1370, 1173, 1004 cm$^{-1}$; MS m/z: 332.2 (M$^+$, 7.5), 301.2 (20.4), 269.2 (100.0), 132.1 (99.5), 120.1 (34.8), 99.1 (32.2), 70.1 (11.4), 55.1 (14.1); HRMS-EI (m/z): [M]$^+$ calculated for C$_{16}$H$_{29}$ClN$_2$O$_3$, 332.1867. found, 332.1880.

Compound-10: methyl 9-(4-(3-chloropropyl)piperazin-1-yl)-9-oxononanoate

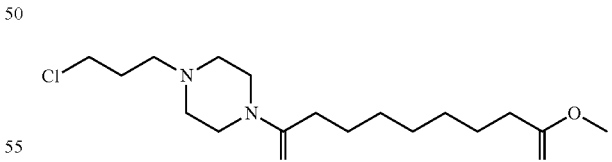

Yield: 63%; $^1$H NMR (400 MHz, CDCl$_3$, δ): 3.64 (s, 3H), 3.60-3.57 (m, 4H), 3.45-3.42 (t, J=4.8 Hz, 2H), 2.50-2.46 (t, J=7.0 Hz, 2H), 2.42-2.36 (m, 4H), 2.29-2.26 (m, 4H), 1.96-89 (m, 2H), 1.61-1.57 (m, 4H), 1.30 (b, 6H); $^{13}$C NMR (100.6 MHz, CDCl$_3$, δ): 174.2, 171.5, 55.2, 53.5, 52.9, 51.4, 45.6, 42.9, 41.5, 34.0, 33.2, 29.7, 29.2, 29.0, 28.9, 25.2, 24.9; IR (KBr): 2932, 2856, 1737, 1645, 1435, 1004 cm$^{-1}$; MS m/z: 346.2 (M$^+$, 0.5), 313.2 (53.4), 284.1 (54.3), 269.1 (26.9), 191.2 (100.0), 132.1 (99.5), 120.1 (10.2), 99.1 (12.3), 55.1 (90.6); HRMS-EI (m/z): [M]$^+$ calculated for C$_{17}$H$_{31}$ClN$_2$O$_3$, 346.2023. found, 346.2031.

(3). Analogue-3 to Analogue-7: (step 9)

Compound-4 (1 eq) was dissolved in N,N-dimethyl formamide (hereinafter referred to DMF) (1.0 mL), potassium carbonate (2 eq) and Compound-6 to Compound-10 (1 eq) were added and heated at 80° C. overnight. The reaction mixture was then cooled to room temperature and quenched by adding water. The resulting solution was extracted with ethyl acetate, and the combined extracts were washed with water and brine, dried over MgSO$_4$, and evaporated to give a residue which was purified by column chromatography to provide Analogue-3 to Analogue-7.

Analogue-3: methyl 5-(4-(3-(4-(3-chloro-4-fluorophenylamino)-7-methoxyquinazolin-6-yloxy)propyl)piperazin-1-yl)-5-oxopentanoate

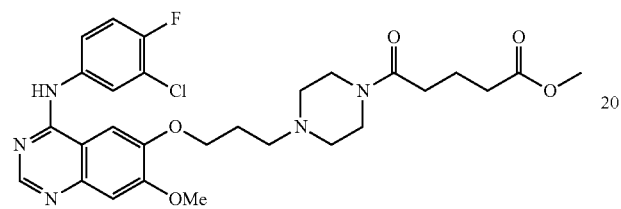

Yield: 40%; $^1$H NMR (400 MHz, CDCl$_3$, δ): 9.50 (s, 1H), 8.43 (s, 1H), 7.83 (s, 1H), 7.79-7.75 (m, 2H), 7.25-7.20 (t, J=8.3 Hz, 2H), 4.20-4.17 (t, J=6.1 Hz, 2H), 3.94 (s, 3H), 3.59 (s, 3H), 3.45-3.42 (m, 4H), 2.41 (b, 2H), 2.36-2.30 (m, 6H), 2.02-1.99 (m, 2H), 1.76-1.69 (m, 2H); $^{13}$C NMR (100.6 MHz, CDCl$_3$, δ): 173.6, 170.4, 160.0, 157.6, 156.9, 154.8, 153.3, 148.7, 147.3, 136.2, 124.9, 124.8, 115.6, 115.4, 109.2, 107.8, 103.2, 67.6, 56.3, 54.9, 53.6, 53.1, 51.7, 45.2, 41.4, 33.1, 31.8, 26.5, 20.7; IR (KBr): 3374, 2949, 1729, 1624, 1508, 1428, 1214, 854 cm$^{-1}$; MS m/z: 573.2 (M$^+$, 6.3), 539.2 (19.6), 508.2 (23.2), 381.2 (35.6), 297.1 (55.8), 285.1 (87.3), 227.1 (100.0), 213.1 (57.0), 99.1 (95.7), 70.1 (85.8), 55.0 (47.0); HRMS-EI (m/z): [M]$^+$ calculated for C$_{28}$H$_{33}$ClFN$_5$O$_5$, 573.2154. found, 573.2940.

Analogue-4: methyl 6-(4-(3-(4-(3-chloro-4-fluorophenylamino)-7-methoxyquinazolin-6-yloxy)propyl)piperazin-1-yl)-6-oxohexanoate

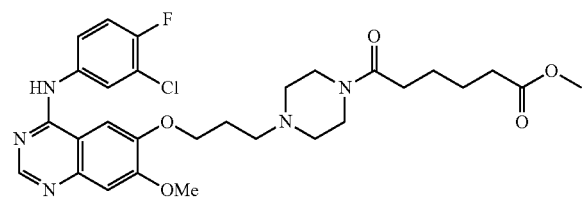 [SMILES: COC(=O)CCCCC(=O)N1CCN(CCCOc2cc3c(Nc4ccc(F)c(Cl)c4)ncnc3cc2OC)CC1]

Yield: 30%; $^1$H NMR (400 MHz, CDCl$_3$, δ): 8.62 (s, 1H), 7.62-7.58 (m, 2H), 7.37 (b, 1H), 7.24 (s, 1H), 7.12-7.07 (m, 2H), 4.18-4.15 (t, J=6.6 Hz, 2H), 3.98 (s, 3H), 3.65 (s, 3H), 3.62-3.60 (t, J=4.7 Hz, 2H), 3.46-3.44 (t, J=4.9 Hz, 2H), 2.59-2.56 (t, J=7.0 Hz, 2H), 2.47-2.40 (m, 4H), 2.35-2.29 (m, 4H), 2.13-2.06 (m, 2H), 1.66 (b, 4H); $^{13}$C NMR (100.6 MHz, CDCl$_3$, δ): 173.9, 171.0, 160.8, 158.4, 156.5, 155.1, 153.7, 148.9, 147.5, 134.5, 124.2, 124.1, 115.9, 115.7, 108.9, 108.0, 100.8, 67.5, 56.2, 54.8, 53.5, 52.9, 51.5, 45.5, 41.5, 33.8, 32.8, 26.4, 24.7, 24.6; IR (KBr): 3379, 2949, 1733, 1623, 1508, 1430, 1214 cm$^{-1}$; MS m/z: 587.2 (M$^+$, 0.9), 551.2 (14.3), 522.2 (23.4), 381.1 (33.5), 355.1 (19.5), 297.1 (53.2), 285.0 (100.0), 269.1 (56.4), 241.1 (80.4), 99.0 (73.4), 70.0 (56.2), 55.0 (44.9); HRMS-EI (m/z): [M]$^+$ calculated for C$_{29}$H$_{35}$ClFN$_5$O$_5$, 587.2311. found, 587.2314.

Analogue-5: methyl 7-(4-(3-(4-(3-chloro-4-fluorophenylamino)-7-methoxyquinazolin-6-yloxy)propyl)piperazin-1-yl)-7-oxoheptanoate

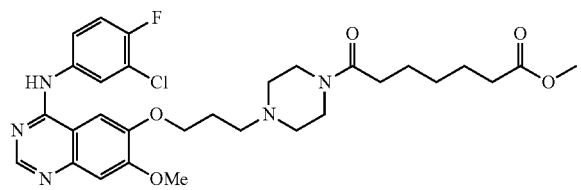 [SMILES: COC(=O)CCCCCC(=O)N1CCN(CCCOc2cc3c(Nc4ccc(F)c(Cl)c4)ncnc3cc2OC)CC1]

Yield: 33%; $^1$H NMR (400 MHz, CDCl$_3$, δ): 8.63 (s, 1H), 7.63-7.59 (m, 2H), 7.24 (s, 1H), 7.12-7.08 (m, 3H), 4.19-4.16 (t, J=6.3 Hz, 2H), 3.99 (s, 3H), 3.66 (s, 3H), 3.62 (b, 3H), 3.46 (b, 3H), 2.61-2.57 (t, J=6.9 Hz, 2H), 2.46-2.44 (m, 4H), 2.33-2.28 (m, 4H), 2.14-2.09 (m, 2H), 1.68-1.60 (m, 4H), 1.40-1.32 (m, 2H); $^{13}$C NMR (100.6 MHz, CDCl$_3$, δ): 174.1, 171.3, 160.9, 158.4, 156.5, 155.2, 153.7, 148.9, 147.6, 134.5, 124.2, 124.1, 115.9, 115.7, 108.8, 108.1, 100.7, 67.6, 56.2, 54.8, 53.5, 52.9, 51.5, 45.5, 41.5, 33.9, 32.9, 28.9, 26.4, 24.9, 24.7; IR (KBr): 2927, 1735, 1624, 1582, 1508, 1429, 1214, 732 cm$^{-1}$.

Analogue-6: methyl 8-(4-(3-(4-(3-chloro-4-fluorophenylamino)-7-methoxyquinazolin-6-yloxy)propyl)piperazin-1-yl)-8-oxooctanoate

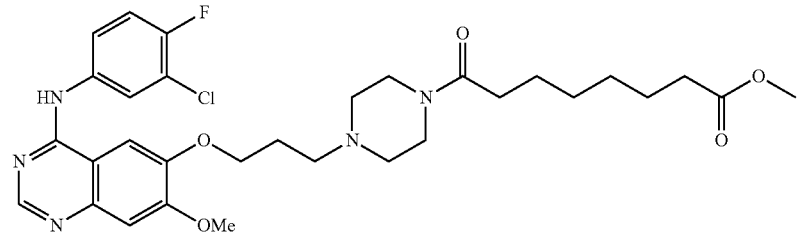 [SMILES: COC(=O)CCCCCCC(=O)N1CCN(CCCOc2cc3c(Nc4ccc(F)c(Cl)c4)ncnc3cc2OC)CC1]

Yield: 35%; $^1$H NMR (400 MHz, CDCl$_3$, δ): 8.63 (s, 1H), 7.63-7.59 (m, 2H), 7.25 (s, 1H), 7.13-7.08 (m, 3H), 4.21-4.18 (t, J=6.5 Hz, 2H), 4.00 (s, 3H), 3.66 (s, 3H), 3.64-3.61 (t, J=5.1 Hz, 2H), 3.48-3.45 (t, J=4.7 Hz, 2H), 2.61-2.58 (t, J=6.9 Hz, 2H), 2.48-2.43 (m, 4H), 2.31-2.28 (t, J=7.4 Hz, 4H), 2.15-2.08 (m, 2H), 1.66-1.60 (m, 4H), 1.36-1.32 (m, 4H); $^{13}$C NMR (100.6 MHz, CDCl$_3$, δ): 174.2, 171.5, 160.9, 158.4, 156.5, 155.2, 153.7, 148.9, 147.6, 134.5, 124.2, 124.1, 115.9, 115.7, 108.8, 108.1, 100.7, 67.6, 56.2, 54.8, 53.5, 52.9, 51.5, 45.6, 41.5, 33.9, 33.1, 29.1, 28.9, 26.4, 25.1, 24.8; IR (KBr): 2931, 1734, 1623, 1583, 1508, 1429, 1244, 1214, 1141, 1005, 833 cm$^{-1}$.

Analogue-7: methyl 9-(4-(3-(4-(3-chloro-4-fluoro-phenylamino)-7-methoxyquinazolin-6-yloxy)propyl)piperazin-1-yl)-9-oxononanoate

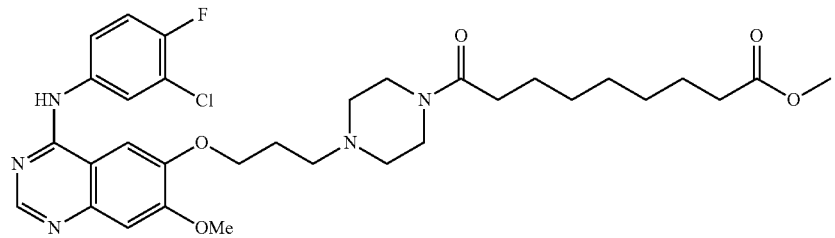 [SMILES: COC(=O)CCCCCCCC(=O)N1CCN(CCCOc2cc3c(Nc4ccc(F)c(Cl)c4)ncnc3cc2OC)CC1]

Yield: 31%; $^1$H NMR (400 MHz, CDCl$_3$, δ): 8.62 (s, 1H), 7.63-7.59 (m, 2H), 7.29 (s, 1H), 7.24 (s, 1H), 7.11-7.07 (m, 2H), 4.19-4.16 (t, J=6.3 Hz, 2H), 3.99 (s, 3H), 3.66 (s, 3H), 3.63-3.61 (t, J=4.7 Hz, 2H), 3.47-3.45 (t, J=4.7 Hz, 2H), 2.60-2.57 (t, J=6.9 Hz, 2H), 2.48-2.42 (m, 4H), 2.31-2.27 (t, J=7.4 Hz, 4H), 2.13-2.06 (m, 2H), 1.62-1.59 (m, 4H), 1.31 (b, 6H); $^{13}$C NMR (100.6 MHz, CDCl$_3$, δ): 174.2, 171.6, 160.8, 158.4, 156.5, 155.2, 153.7, 148.9, 147.6, 134.5, 124.2, 124.1, 115.9, 115.7, 108.9, 108.1, 100.9, 67.6, 56.2, 54.8, 53.5, 52.9, 51.4, 45.6, 41.5, 34.0, 33.2, 29.2, 29.0, 28.9, 26.5, 25.2, 24.9; IR (KBr): 2927, 1732, 1628, 1508, 1265, 739, 704 cm$^{-1}$; MS m/z: 629.4 (M$^+$, 0.9), 593.4 (20.8), 564.4 (27.7), 381.2 (54.3), 355.2 (32.6), 312.2 (40.8), 297.2 (80.6), 285.1 (100.0), 269.1 (25.8), 125.1 (31.2), 99.1 (99.6), 70.1 (77.6), 55.1 (64.7); HRMS-EI (m/z): [M]$^+$ calculated for C$_{32}$H$_{41}$ClFN$_5$O$_5$, 629.2780. found, 629.2789.

3. Synthesis of Analogue-8 to Analogue-26

(1). Compound-11 to Compound-29: (step 10)

A mixture of succinic anhydride (1.0 eq) and dry alcohol (carbon number is from 2 to 20) (1 eq) in 4 mL toluene was heated at reflux 2.5 hours. The toluene was removed under reduced pressure and the residue was taken up in water, and the solution was extracted with dichloromethane, dried over MgSO$_4$, and evaporated to obtain monoalkylsuccinic acid (carbon number is from 2 to 20).

A solution of monoalkyl succinic acid (carbon number of the alhyl is from 2 to 20) (1.2 eq) and thionyl chloride (1.4 eq) in benzene (5 mL) was refluxed for 3 hours. Subsequently, the majority of the thionyl chloride and benzene were removed by distillation. The mixture was cooled down to room temperature and dried under a vacuum to give a crude chlorocarbony-alkyl ester (carbon number of the alhyl is from 2 to 20). A solution of chlorocarbonyl-alkyl ester (carbon number of the alhyl is from 2 to 20) in 5 mL dichloromethane was added to a round flask containing Compound-5 (1 eq) by cannula, and subsequently added pyridine (1.4 eq). The resulting solution was stirred at room temperature overnight, and quenched by adding water. The solution was extracted with ethyl acetate, dried over MgSO$_4$, and evaporated to give a residue which was purified by column chromatography (Al$_2$O$_3$), eluting by ethyl acetate/hexane (1:15) to provide Compound-11 to Compound-29 (the physical and chemical data shown in Table 1).

Compound-11: ethyl 4-(4-(3-chloropropyl)piperazin-1-yl)-4-oxobutanoate

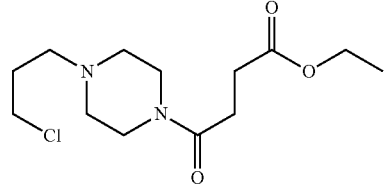 [SMILES: CCOC(=O)CCC(=O)N1CCN(CCCCl)CC1]

Compound-12: propyl 4-(4-(3-chloropropyl)piperazin-1-yl)-4-oxobutanoate

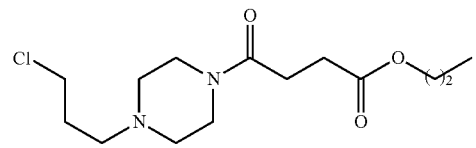

Compound-13: butyl 4-(4-(3-chloropropyl)piperazin-1-yl)-4-oxobutanoate

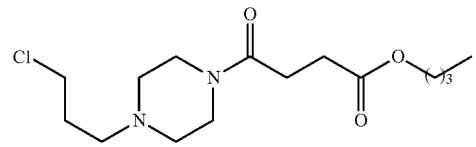

Compound-14: pentyl 4-(4-(3-chloropropyl)piper-
azin-1-yl)-4-oxobutanoate

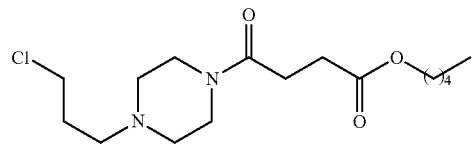

Compound-15: hexyl 4-(4-(3-chloropropyl)piper-
azin-1-yl)-4-oxobutanoate

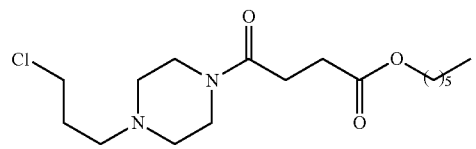

Compound-16: heptyl 4-(4-(3-chloropropyl)piper-
azin-1-yl)-4-oxobutanoate

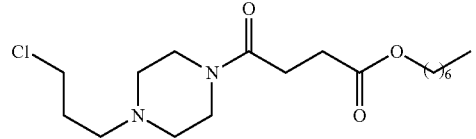

Compound-17: octyl 4-(4-(3-chloropropyl)piper-
azin-1-yl)-4-oxobutanoate

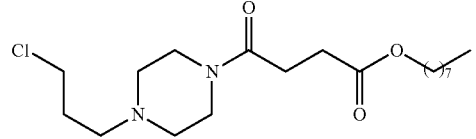

Compound-18: nonyl 4-(4-(3-chloropropyl)piper-
azin-1-yl)-4-oxobutanoate

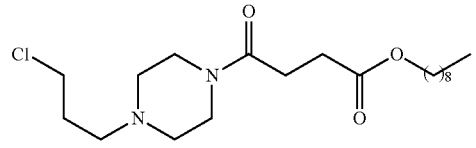

Compound-19: decyl 4-(4-(3-chloropropyl)piper-
azin-1-yl)-4-oxobutanoate

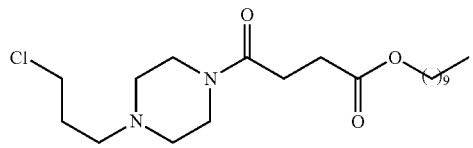

Compound-20: undecyl 4-(4-(3-chloropropyl)piper-
azin-1-yl)-4-oxobutanoate

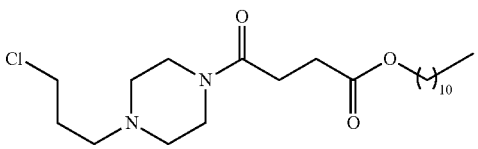

Compound-21: dodecyl 4-(4-(3-chloropropyl)piper-
azin-1-yl)-4-oxobutanoate

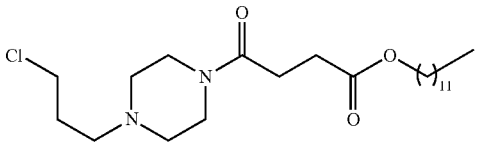

Compound-22: tridecyl 4-(4-(3-chloropropyl)piper-
azin-1-yl)-4-oxobutanoate

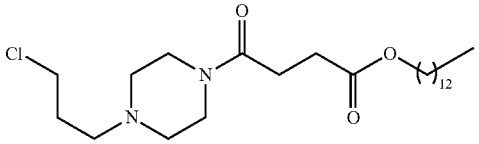

Compound-23: tetradecyl 4-(4-(3-chloropropyl)pip-
erazin-1-yl)-4-oxobutanoate

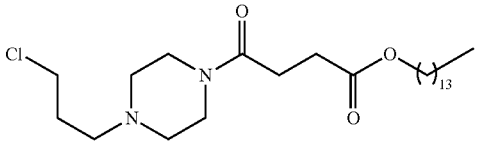

Compound-24: pentadecyl 4-(4-(3-chloropropyl)piperazin-1-yl)-4-oxobutanoate

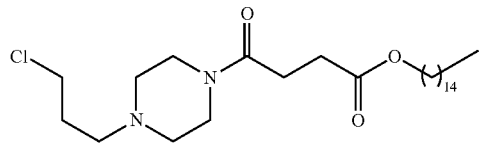

Compound-25: hexadecyl 4-(4-(3-chloropropyl)piperazin-1-yl)-4-oxobutanoate

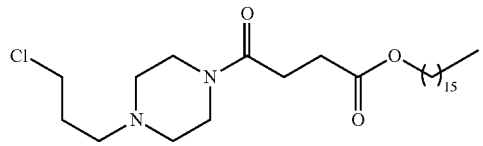

Compound-26: heptadecyl 4-(4-(3-chloropropyl)piperazin-1-yl)-4-oxobutanoate

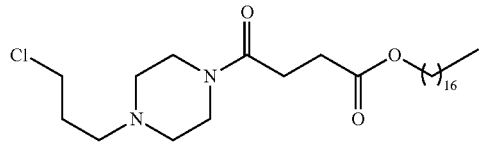

Compound-27: octadecyl 4-(4-(3-chloropropyl)piperazin-1-yl)-4-oxobutanoate

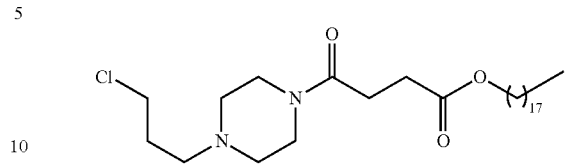

Compound-28: nonadecyl 4-(4-(3-chloropropyl)piperazin-1-yl)-4-oxobutanoate

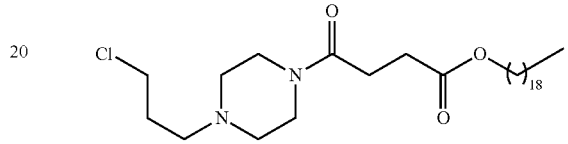

Compound-29: icosyl 4-(4-(3-chloropropyl)piperazin-1-yl)-4-oxobutanoate

TABLE 1

Physical and chemical data of Compound-11 to Compound-29

| Compound | Physical and chemical data |
|---|---|
| Compound-11 (Yield: 61%) | $^1$H NMR (400 MHz, CDCl$_3$, δ): 4.18-4.10 (q, J = 7.1 Hz, 2H), 3.60-3.58 (t, J = 4.1 Hz, 4H), 3.50-3.47 (t, J = 5.0 Hz, 2H), 2.64-2.52 (m, 4H), 2.51-2.47 (t, J = 6.9 Hz, 2H), 2.45-2.37 (m, 4H), 1.96-1.91 (dd, J = 13.5, 6.7 Hz, 2H), 1.28-1.23 (t, J = 7.1 Hz, 3H); IR (KBr): 2918, 2846, 1733, 1641, 1444, 1375, 1229, 1174 cm$^{-1}$. MS m/z: 255.3 (5.8), 207.1 (16.7), 147.1 (39.1), 73.0 (100.0). |
| Compound-12 (Yield: 66%) | $^1$H NMR (400 MHz, CDCl$_3$, δ): 4.05-4.02 (t, J = 6.7 Hz, 2H), 3.61-3.58 (m, 4H), 3.49-3.47 (t, J = 5.0 Hz, 2H), 2.67-2.59 (m, 4H), 2.51-2.47 (t, J = 6.9 Hz, 2H), 2.45-2.37 (m, 4H), 1.96-1.91 (dd, J = 13.5, 6.7 Hz, 2H), 1.28-1.23 (t, J = 7.1 Hz, 3H); $^{13}$C NMR (100.6 MHz, CDCl$_3$, δ): 173.1, 169.5, 66.1, 55.0, 53.2, 52.7, 45.2, 42.9, 41.6, 29.6, 29.2, 27.8, 21.9, 10.3; IR (KBr): 2963, 2920, 1730, 1646, 1444, 1351, 1266, 1173 cm$^{-1}$; HRFAB (m/z): [M]$^+$ calculated for C$_{14}$H$_{25}$ClN$_2$O$_3$, 304.1554; found, 304.1548. |
| Compound-13 (Yield: 55%) | $^1$H NMR (300 MHz, CDCl$_3$, δ): 4.10-4.06 (t, J = 6.6 Hz, 2H), 3.62-3.58 (m, 4H), 3.49-3.47 (t, J = 5.0 Hz, 2H), 2.65-2.62 (m, 4H), 2.52-2.47 (t, J = 6.9 Hz, 2H), 2.45-2.39 (m, 4H), 1.96-1.91 (dd, J = 13.5, 6.7 Hz, 2H), 1.28-1.23 (t, J = 7.1 Hz, 3H); $^{13}$C NMR (100.6 MHz, CDCl$_3$, δ): 173.1, 169.5, 64.4, 55.0, 53.2, 52.7, 45.1, 42.9, 41.6, 30.5, 29.6, 29.2, 27.7, 19.0, 13.6. |
| Compound-14 (Yield: 63%) | $^1$H NMR (400 MHz, CDCl$_3$, δ): 4.09-4.06 (t, J = 6.8 Hz, 2H), 3.62-3.59 (m, 4H), 3.50-3.47 (t, J = 5.0 Hz, 2H), 2.66-2.59 (m, 4H), 2.51-2.48 (t, J = 6.9 Hz, 2H), 2.45-2.38 (m, 4H), 1.95-1.90 (m, 2H), 1.64-1.61 (m, 2H), 1.34-1.25 (m, 4H), 0.91-0.88 (t, J = 6.6 Hz, 3H); $^{13}$C NMR (100.6 MHz, CDCl$_3$, δ): 173.1, 169.5, 64.7, 55.1, 53.3, 52.7, 45.2, 42.9, 41.7, 29.7, 29.3, 28.2, 28.0, 27.8, 22.3, 13.9; IR (KBr): 2959, 2934, 1731, 1647, 1449, 1366, 1238, 1173 cm$^{-1}$. |

TABLE 1-continued

Physical and chemical data of Compound-11 to Compound-29

| Compound | Physical and chemical data |
|---|---|
| Compound-15 (Yield: 52%) | $^1$H NMR (400 MHz, CDCl$_3$, δ): 4.09-4.05 (t, J = 6.7 Hz, 2H), 3.62-3.58 (m, 4H), 3.50-3.47 (t, J = 4.9 Hz, 2H), 2.66-2.60 (m, 4H), 2.51-2.48 (t, J = 6.9 Hz, 2H), 2.45-2.38 (m, 4H), 1.97-1.90 (m, 2H), 1.65-1.58 (m, 2H), 1.35-1.25 (m, 6H), 0.89-0.86 (t, J = 6.6 Hz, 3H); IR (KBr): 2927, 2856, 1728, 1646, 1456, 1351, 1265, 1175 cm$^{-1}$; HRFAB (m/z): [M]$^+$ calculated for C$_{17}$H$_{31}$ClN$_2$O$_3$, 346.2023; found, 346.2028. |
| Compound-16 (Yield: 57%) | $^1$H NMR (400 MHz, CDCl$_3$, δ): 4.08-4.05 (t, J = 6.8 Hz, 2H), 3.61-3.58 (m, 4H), 3.50-3.47 (t, J = 4.9 Hz, 2H), 2.67-2.60 (m, 4H), 2.51-2.48 (t, J = 7.0 Hz, 2H), 2.45-2.38 (m, 4H), 1.97-1.90 (m, 2H), 1.63-1.58 (m, 2H), 1.34-1.27 (m, 8H), 0.89-0.85 (t, J = 6.6 Hz, 3H); IR (KBr): 2937, 2859, 1734, 1649, 14418, 13539, 1265, 1033 cm$^{-1}$. |
| Compound-17 (Yield: 51%) | $^1$H NMR (400 MHz, CDCl$_3$, δ): 4.08-4.05 (t, J = 6.8 Hz, 2H), 3.61-3.58 (m, 4H), 3.50-3.47 (t, J = 4.9 Hz, 2H), 2.66-2.60 (m, 4H), 2.51-2.47 (t, J = 6.9 Hz, 2H), 2.45-2.38 (m, 4H), 1.97-1.90 (m, 2H), 1.63-1.57 (m, 2H), 1.34-1.23 (m, 10H), 0.88-0.85 (t, J = 6.6 Hz, 3H); $^{13}$C NMR (100.6 MHz, CDCl$_3$, δ): 173.2, 169.6, 64.8, 55.1, 53.2, 52.7, 45.2, 42.9, 41.7, 31.7, 29.7, 29.3, 29.1, 29.1, 28.5, 27.8, 25.8, 22.6, 14.0; IR (KBr): 2927, 2855, 1731, 1647, 1444, 1352, 1265, 1171 cm$^{-1}$; MS m/z: 375.3 (M$^+$, 21.4), 339.3 (77.1), 228.0 (87.5), 95.0 (85.3); HRFAB (m/z): [M]$^+$ calculated for C$_{19}$H$_{35}$ClN$_2$O$_3$, 374.2336; found, 374.2338. |
| Compound-18 (Yield: 51%) | $^1$H NMR (400 MHz, CDCl$_3$, δ): 4.09-4.05 (t, J = 6.8 Hz, 2H), 3.62-3.59 (m, 4H), 3.50-3.47 (t, J = 4.9 Hz, 2H), 2.67-2.59 (m, 4H), 2.51-2.48 (t, J = 6.9 Hz, 2H), 2.45-2.38 (m, 4H), 1.97-1.90 (m, 2H), 1.63-1.57 (m, 2H), 1.34-1.23 (m, 12H), 0.88-0.85 (t, J = 6.6 Hz, 3H); $^{13}$C NMR (100.6 MHz, CDCl$_3$, δ): 173.2, 169.6, 64.8, 55.1, 53.3, 52.7, 45.2, 42.9, 41.7, 31.8, 29.7, 29.4, 29.3, 29.2, 29.2, 28.6, 27.8, 25.8, 22.6, 14.0; IR (KBr): 2925, 2855, 1731, 1650, 1445, 1366, 1232, 1169 cm$^{-1}$. |
| Compound-19 (Yield: 51%) | $^1$H NMR (400 MHz, CDCl$_3$, δ): 4.08-4.05 (t, J = 6.8 Hz, 2H), 3.60-3.57 (m, 4H), 3.51-3.48 (t, J = 4.9 Hz, 2H), 2.66-2.58 (m, 4H), 2.50-2.47 (t, J = 6.9 Hz, 2H), 2.46-2.39 (m, 4H), 1.96-1.90 (m, 2H), 1.63-1.57 (m, 2H), 1.34-1.23 (m, 14H), 0.88-0.85 (t, J = 6.6 Hz, 3H); $^{13}$C NMR (100.6 MHz, CDCl$_3$, δ): 173.2, 169.6, 64.8, 55.1, 53.3, 52.7, 45.2, 42.9, 41.7, 31.8, 29.7, 29.4, 29.3, 29.3, 29.2, 29.2, 28.6, 27.8, 25.8, 22.6, 14.0; IR (KBr): 2925, 2855, 1733, 1650, 1444, 1365, 1232, 1169 cm$^{-1}$. HRFAB (m/z): [M]$^+$ calculated for C$_{21}$H$_{39}$ClN$_2$O$_3$, 402.2649; found, 402.2641. |
| Compound-20 (Yield: 50%) | $^1$H NMR (400 MHz, CDCl$_3$, δ): 4.06-4.02 (t, J = 6.8 Hz, 2H), 3.59-3.56 (m, 4H), 3.47-3.45 (t, J = 4.9 Hz, 2H), 2.64-2.56 (m, 4H), 2.48-2.45 (t, J = 6.9 Hz, 2H), 2.42-2.35 (m, 4H), 1.94-1.91 (m, 2H), 1.63-1.57 (m, 2H), 1.34-1.23 (m, 16H), 0.88-0.85 (t, J = 6.6 Hz, 3H); $^{13}$C NMR (100.6 MHz, CDCl$_3$, δ): 173.1, 169.5, 64.7, 55.1, 53.2, 52.7, 45.2, 42.9, 41.7, 31.8, 29.7, 29.5, 29.5, 29.4, 29.2, 29.2, 28.5, 27.8, 25.8, 22.6, 14.0; IR (KBr): 2925, 2854, 1735, 1650, 1440, 1363, 1222, 1169 cm$^{-1}$. MS m/z: 416.2 (M$^+$, 1.32), 281.1 (14.2), 221.1 (11.3), 207.1 (13.9), 139.4 (35.6), 60.3 (100.0). HRFAB (m/z): [M]$^+$ calculated for C$_{22}$H$_{41}$ClN$_2$O$_3$, 416.2806; found, 416.2799. |
| Compound-21 (Yield: 54%) | $^1$H NMR (400 MHz, CDCl$_3$, δ): 4.07-4.03 (t, J = 6.8 Hz, 2H), 3.60-3.57 (m, 4H), 3.48-3.46 (t, J = 4.9 Hz, 2H), 2.65-2.57 (m, 4H), 2.50-2.46 (t, J = 6.9 Hz, 2H), 2.44-2.37 (m, 4H), 1.95-1.92 (m, 2H), 1.63-1.57 (m, 2H), 1.34-1.23 (b, 18H), 0.88-0.85 (t, J = 6.6 Hz, 3H); $^{13}$C NMR (100.6 MHz, CDCl$_3$, δ): 173.2, 169.5, 64.8, 55.1, 53.2, 52.7, 45.2, 42.9, 41.7, 31.9, 29.7, 29.6, 29.5, 29.5, 29.3, 29.2, 29.2, 28.5, 27.8, 25.8, 22.6, 14.0; IR (KBr): 2925, 2854, 1734, 1651, 1444, 1365, 1223, 1169 cm$^{-1}$. MS m/z: 430.3 (M$^+$, 62.5), 281.1 (11.7), 228.0 (11.7), 221.1 (11.1), 207.1 (18.7), 139.4 (41.3), 60.3 (100.0). HRFAB (m/z): [M]$^+$ calculated for C$_{23}$H$_{43}$ClN$_2$O$_3$, 430.2963; found, 430.2954. |
| Compound-22 (Yield: 55%) | $^1$H NMR (400 MHz, CDCl$_3$, δ): 4.09-4.05 (t, J = 6.8 Hz, 2H), 3.62-3.59 (m, 4H), 3.50-3.47 (t, J = 4.9 Hz, 2H), 2.68-2.59 (m, 4H), 2.51-2.48 (t, J = 6.9 Hz, 2H), 2.45-2.38 (m, 4H), 1.97-1.90 (m, 2H), 1.63-1.57 (m, 2H), 1.34-1.23 (b, 20H), 0.88-0.85 (t, J = 6.6 Hz, 3H). $^{13}$C NMR (100.6 MHz, $^{13}$C NMR (100.6 MHz, CDCl$_3$, δ): 173.2, 169.6, 64.8, 55.1, 53.2, 52.7, 45.1, 42.9, 41.6, 31.9, 29.6, 29.5, 29.5, 29.3, 29.2, 28.6, 27.8, 25.9, 22.6, 14.1; IR (KBr): 2924, 2853, 1734, 1651, 1464, 1363, 1222, 1169 cm$^{-1}$. MS m/z: 444.2 (M$^+$, 2.0), 325.0 (5.0), 281.1 (11.8), 221.1 (12.3), 207.1 (17.5), 139.4 (29.6), 60.3 (100.0). HRFAB (m/z): [M]$^+$ calculated for C$_{24}$H$_{45}$ClN$_2$O$_3$, 444.3119; found, 444.3157. |
| Compound-23 (Yield: 49%) | $^1$H NMR (400 MHz, CDCl$_3$, δ): 4.09-4.05 (t, J = 6.8 Hz, 2H), 3.62-3.59 (m, 4H), 3.50-3.47 (t, J = 4.9 Hz, 2H), 2.68-2.59 (m, 4H), 2.51-2.48 (t, J = 6.9 Hz, 2H), 2.45-2.38 (m, 4H), 1.97-1.90 (m, 2H), 1.63-1.57 (m, 2H), 1.34-1.23 (b, 22H), 0.88-0.85 (t, J = 6.6 Hz, 3H); $^{13}$C NMR (100.6 MHz, CDCl$_3$, δ): 173.1, 169.5, 64.7, 55.1, 53.2, 52.7, 45.2, 42.9, 41.7, 31.8, 29.7, 29.5, 29.4, 29.2, 29.2, 28.5, 27.8, 25.8, 22.6, 14.0; IR (KBr): 2924, 2853, 1735, 1652, 1444, 1364, 1222, 1169 cm$^{-1}$. MS m/z: 458.1 (M$^+$, 60.3), 422.3 (17.1), 281.1 (17.1), 221.1 (16.1), 207.1 (17.7), 139.4 (40.33), 60.3 (100.0); HRFAB (m/z): [M]$^+$ calculated for C$_{25}$H$_{47}$ClN$_2$O$_3$, 458.3275; found, 458.3261. |

TABLE 1-continued

Physical and chemical data of Compound-11 to Compound-29

| Compound | Physical and chemical data |
| --- | --- |
| Compound-24 (Yield: 52%) | $^1$H NMR (400 MHz, CDCl$_3$, δ): 4.04-4.01 (t, J = 6.7 Hz, 2H), 3.57-3.54 (m, 4H), 3.46-3.43 (t, J = 4.8 Hz, 2H), 2.63-2.55 (m, 4H), 2.47-2.44 (t, J = 6.9 Hz, 2H), 2.41-2.34 (m, 4H), 1.93-1.86 (m, 2H), 1.63-1.57 (m, 2H), 1.30-1.19 (b, 24H), 0.88-0.85 (t, J = 6.6 Hz, 3H); $^{13}$C NMR (100.6 MHz, CDCl$_3$, δ): 173.1, 169.5, 64.7, 55.0, 53.2, 52.7, 45.2, 42.8, 41.7, 31.8, 29.7, 29.6, 29.6, 29.5, 29.4, 29.3, 29.2, 29.2, 28.5, 27.8, 25.8, 22.6, 14.0; IR (KBr): 2924, 2853, 1735, 1652, 1444, 1365, 1223, 1169 cm$^{-1}$. MS m/z: 473.3 (M$^+$, 19.1), 409.3 (10.3), 281.1 (11.4), 245.1 (19.8), 221.1 (10.2), 207.1 (18.8), 140.1 (37.2), 60.3 (100.0). HRFAB (m/z): [M]$^+$ calculated for C$_{26}$H$_{49}$ClN$_2$O$_3$, 472.3432; found, 472.3436. |
| Compound-25 (Yield: 45%) | $^1$H NMR (400 MHz, CDCl$_3$, δ): 4.02-3.99 (t, J = 6.7 Hz, 2H), 3.55-3.52 (m, 4H), 3.44-3.42 (t, J = 4.7 Hz, 2H), 2.60-2.54 (m, 4H), 2.45-2.42 (t, J = 6.9 Hz, 2H), 2.39-2.32 (m, 4H), 1.91-1.86 (m, 2H), 1.63-1.57 (m, 2H), 1.30-1.19 (b, 26H), 0.88-0.85 (t, J = 6.6 Hz, 3H); $^{13}$C NMR (100.6 MHz, CDCl$_3$, δ): 173.1, 169.5, 64.7, 55.0, 53.2, 52.7, 45.2, 42.8, 41.6, 31.8, 29.6, 29.6, 29.6, 29.5, 29.4, 29.3, 29.2, 29.2, 28.5, 27.8, 25.8, 22.6, 14.0; IR (KBr): 2924, 2852, 1735, 1652, 1444, 1364, 1222, 1170 cm$^{-1}$. MS m/z: 487.3 (M$^+$, 3.6), 423.3 (2.4), 281.1 (2.3), 221.1 (2.1), 207.1 (3.2), 140.1 (5.6), 53.6 (100.0). HRFAB (m/z): [M]$^+$ calculated for C$_{27}$H$_{51}$ClN$_2$O$_3$, 486.3588; found, 486.3562. |
| Compound-26 (Yield: 56%) | $^1$H NMR (400 MHz, CDCl$_3$, δ): 4.07-4.04 (t, J = 6.8 Hz, 2H), 3.60-3.57 (m, 4H), 3.48-3.46 (t, J = 4.9 Hz, 2H), 2.66-2.57 (m, 4H), 2.50-2.46 (t, J = 6.9 Hz, 2H), 2.44-2.37 (m, 4H), 1.96-1.92 (m, 2H), 1.63-1.57 (m, 2H), 1.34-1.23 (b, 28H), 0.88-0.85 (t, J = 6.6 Hz, 3H); $^{13}$C NMR (100.6 MHz, CDCl$_3$, δ): 173.2, 169.6, 64.8, 55.1, 53.3, 52.7, 45.2, 42.9, 41.7, 31.9, 29.6, 29.6, 29.5, 29.5, 29.3, 29.3, 29.2, 28.6, 27.8, 25.9, 22.6, 14.1; IR (KBr): 2919, 2850, 1732, 1642, 1465, 1306, 1188, 1170 cm$^{-1}$. MS m/z: 501.3 (M$^+$, 1.94), 429.0 (2.11), 400.9 (3.59), 355.0 (5.0), 281.1 (19.1), 221.1 (10.3), 207.1 (18.6), 140.1 (45.7), 60.3 (100.0). HRFAB (m/z): [M]$^+$ calculated for C$_{28}$H$_{53}$ClN$_2$O$_3$, 500.3745; found, 500.3749. |
| Compound-27 (Yield: 48%) | $^1$H NMR (400 MHz, CDCl$_3$, δ): 4.09-4.05 (t, J = 6.8 Hz, 2H), 3.62-3.59 (m, 4H), 3.50-3.47 (t, J = 4.9 Hz, 2H), 2.68-2.59 (m, 4H), 2.51-2.48 (t, J = 6.9 Hz, 2H), 2.45-2.38 (m, 4H), 1.97-1.91 (m, 2H), 1.63-1.57 (m, 2H), 1.30-1.25 (b, 30H), 0.89-0.86 (t, J = 6.6 Hz, 3H); $^{13}$C NMR (100.6 MHz, CDCl$_3$, δ): 173.1, 169.5, 64.7, 55.0, 53.2, 52.7, 45.2, 42.8, 41.6, 31.8, 29.6, 29.6, 29.5, 29.5, 29.3, 29.2, 29.2, 28.5, 27.8, 25.9, 22.6, 14.1. MS m/z: 515.3 (M$^+$, 9.2), 451.3 (5.0), 400.9 (5.7), 281.1 (18.1), 207.1 (16.8), 140.1 (36.8), 60.3 (100.0). HRFAB (m/z): [M]$^+$ calculated for C$_{29}$H$_{55}$ClN$_2$O$_3$, 514.3901; found, 514.3895. |
| Compound-28 (Yield: 44%) | $^1$H NMR (400 MHz, CDCl$_3$, δ): 4.08-4.05 (t, J = 6.8 Hz, 2H), 3.61-3.58 (m, 4H), 3.49-3.47 (t, J = 4.9 Hz, 2H), 2.66-2.59 (m, 4H), 2.51-2.47 (t, J = 6.9 Hz, 2H), 2.45-2.38 (m, 4H), 1.97-1.90 (m, 2H), 1.63-1.57 (m, 2H), 1.34-1.23 (m, 32H), 0.88-0.85 (t, J = 6.6 Hz, 3H); $^{13}$C NMR (100.6 MHz, CDCl$_3$, δ): 173.2, 169.6, 64.8, 55.1, 53.3, 52.7, 45.2, 42.9, 41.7, 31.9, 29.6, 29.5, 29.5, 29.3, 29.3, 29.2, 28.6, 27.8, 25.9, 22.6, 14.0; IR (KBr): 2918, 2850, 1732, 1633, 1464, 1364, 1306, 1169 cm$^{-1}$. MS m/z: 529.3 (M$^+$, 5.5), 465.3 (2.9), 400.9 (2.7), 355.0 (2.9), 281.1 (10.2), 207.1 (11.6), 140.1 (33.4), 60.3 (100.0). HRFAB (m/z): [M]$^+$ calculated for C$_{30}$H$_{57}$ClN$_2$O$_3$, 528.4058; found, 528.4052. |
| Compound-29 (Yield: 46%) | $^1$H NMR (400 MHz, CDCl$_3$, δ): 4.09-4.05 (t, J = 6.8 Hz, 2H), 3.62-3.58 (m, 4H), 3.50-3.47 (t, J = 4.9 Hz, 2H), 2.67-2.59 (m, 4H), 2.51-2.48 (t, J = 6.9 Hz, 2H), 2.45-2.38 (m, 4H), 1.97-1.91 (m, 2H), 1.63-1.57 (m, 2H), 1.30-1.25 (b, 34H), 0.89-0.86 (t, J = 6.6 Hz, 3H); $^{13}$C NMR (100.6 MHz, CDCl$_3$, δ): 173.2, 169.6, 64.8, 55.1, 53.3, 52.7, 45.2, 42.9, 41.7, 31.9, 29.7, 29.6, 29.5, 29.5, 29.3, 29.2, 29.2, 28.6, 27.8, 25.9, 22.6, 14.1; IR (KBr): 2919, 2850, 1732, 1642, 1465, 1367, 1226, 1171 cm$^{-1}$. MS m/z: 543.4 (M$^+$, 10.8), 507.4 (6.2), 355.0 (3.5), 281.1 (14.7), 221.1 (16.3) 207.1 (17.9), 140.1 (40.3), 60.4 (100.0). HRFAB (m/z): [M]$^+$ calculated for C$_{31}$H$_{59}$ClN$_2$O$_3$, 542.4214; found, 542.4220. |

(2). Synthesis of Analogue-8 to Analogue-26: (step 11)

Compound-4 (1 eq) was dissolved in DMF (1.0 mL), potassium carbonate (2 eq) and Compound-11 to Compound-29 (1 eq) were added respectively and heated at 80° C. overnight. The reaction mixture was then cooled to room temperature and quenched by adding water. The resulting solution was extracted with ethyl acetate; the combined extracts were washed with water and brine, dried over MgSO$_4$, and evaporated to give a crude residue which was purified by column chromatography to provide Analogue-8 to Analogue-26 (physical and chemical data shown in Table 2).

Analogue-8: ethyl 4-(4-(3-(4-(3-chloro-4-fluorophenylamino)-7-methoxyquinazolin-6-yloxy)propyl)piperazin-1-yl)-4-oxobutanoate

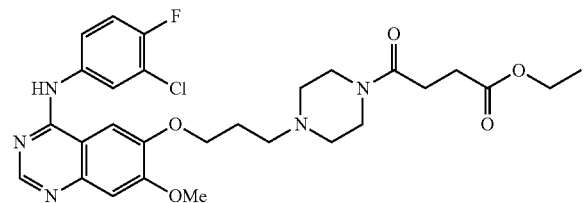 [SMILES: CCOC(=O)CCC(=O)N1CCN(CCCOc2cc3c(Nc4ccc(F)c(Cl)c4)ncnc3cc2OC)CC1]

Analogue-9: propyl 4-(4-(3-(4-(3-chloro-4-fluorophenylamino)-7-methoxyquinazolin-6-yloxy)propyl)piperazin-1-yl)-4-oxobutanoate

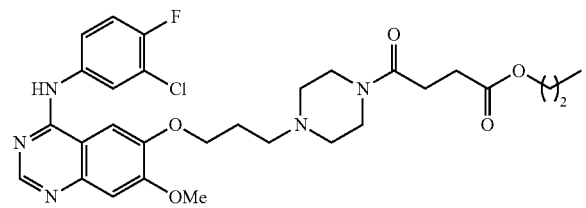

Analogue-10: butyl 4-(4-(3-(4-(3-chloro-4-fluorophenylamino)-7-methoxyquinazolin-6-yloxy)propyl)piperazin-1-yl)-4-oxobutanoate

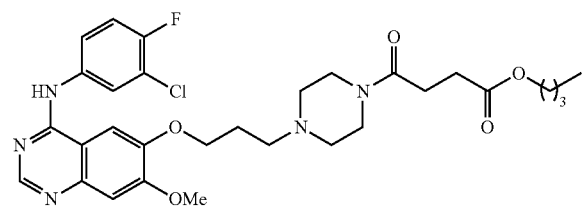

Analogue-11: pentyl 4-(4-(3-(4-(3-chloro-4-fluorophenylamino)-7-methoxyquinazolin-6-yloxy)propyl)piperazin-1-yl)-4-oxobutanoate

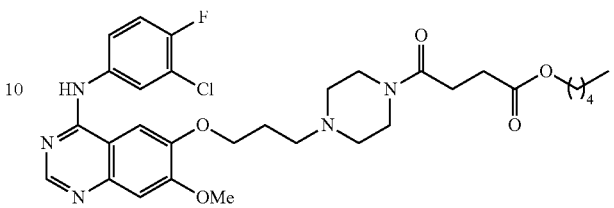

Analogue-12: hexyl 4-(4-(3-(4-(3-chloro-4-fluorophenylamino)-7-methoxyquinazolin-6-yloxy)propyl)piperazin-1-yl)-4-oxobutanoate

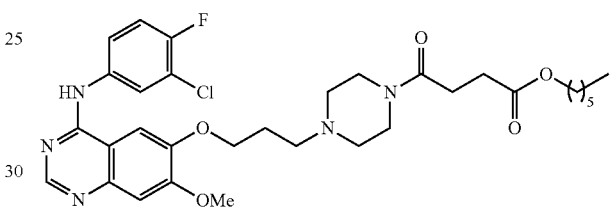

Analogue-13: heptyl 4-(4-(3-(4-(3-chloro-4-fluorophenylamino)-7-methoxyquinazolin-6-yloxy)propyl)piperazin-1-yl)-4-oxobutanoate

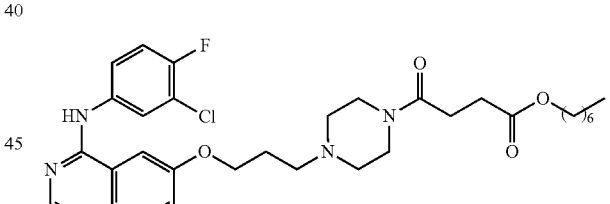

Analogue-14: octyl 4-(4-(3-(4-(3-chloro-4-fluorophenylamino)-7-methoxyquinazolin-6-yloxy)propyl)piperazin-1-yl)-4-oxobutanoate

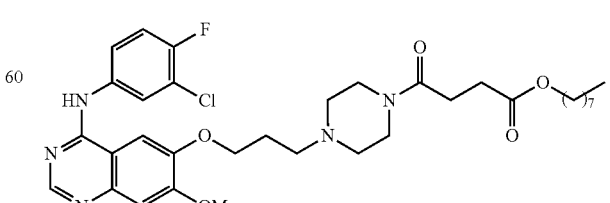

Analogue-15: nonyl 4-(4-(3-(4-(3-chloro-4-fluoro-phenylamino)-7-methoxyquinazolin-6-yloxy)propyl)piperazin-1-yl)-4-oxobutanoate

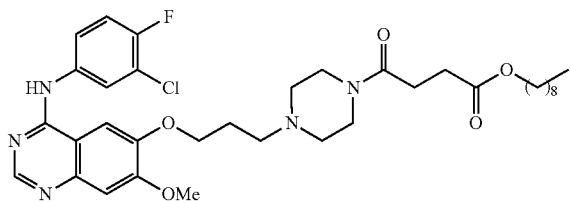

Analogue-16: decyl 4-(4-(3-(4-(3-chloro-4-fluoro-phenylamino)-7-methoxyquinazolin-6-yloxy)propyl)piperazin-1-yl)-4-oxobutanoate

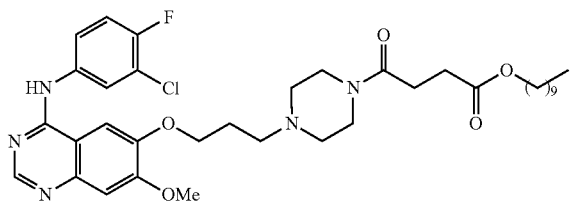

Analogue-17: undecyl 4-(4-(3-(4-(3-chloro-4-fluoro-phenylamino)-7-methoxyquinazolin-6-yloxy)propyl)piperazin-1-yl)-4-oxobutanoate

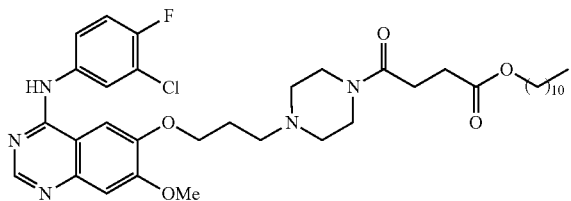

Analogue-18: dodecyl 4-(4-(3-(4-(3-chloro-4-fluoro-phenylamino)-7-methoxyquinazolin-6-yloxy)propyl)piperazin-1-yl)-4-oxobutanoate

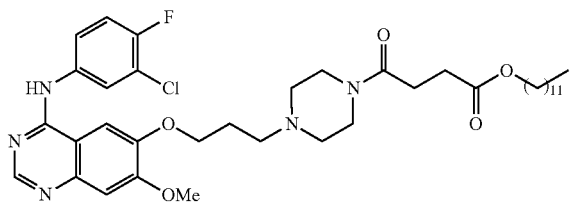

Analogue-19: tridecyl 4-(4-(3-(4-(3-chloro-4-fluoro-phenylamino)-7-methoxyquinazolin-6-yloxy)propyl)piperazin-1-yl)-4-oxobutanoate

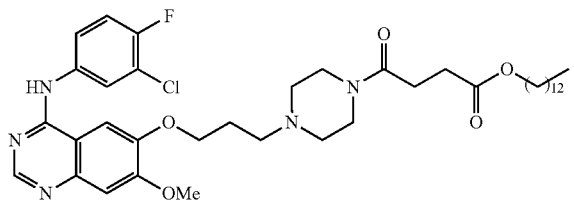

Analogue-20: tetradecyl 4-(4-(3-(4-(3-chloro-4-fluorophenylamino)-7-methoxyquinazolin-6-yloxy)propyl)piperazin-1-yl)-4-oxobutanoate

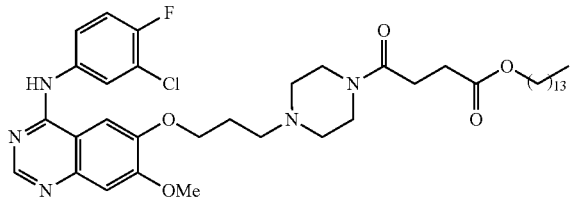

Analogue-21: pentadecyl 4-(4-(3-(4-(3-chloro-4-fluorophenylamino)-7-methoxyquinazolin-6-yloxy)propyl)piperazin-1-yl)-4-oxobutanoate

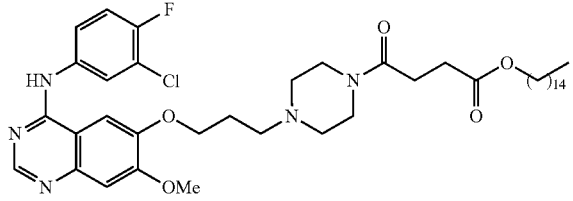

Analogue-22: hexadecyl 4-(4-(3-(4-(3-chloro-4-fluorophenylamino)-7-methoxyquinazolin-6-yloxy)propyl)piperazin-1-yl)-4-oxobutanoate

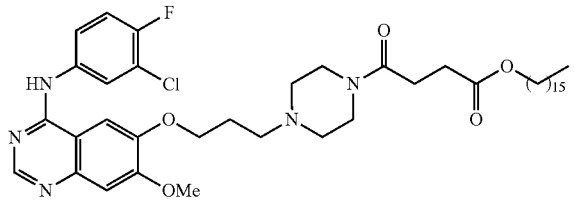

29

Analogue-23: heptadecyl 4-(4-(3-(4-(3-chloro-4-fluorophenylamino)-7-methoxyquinazolin-6-yloxy)propyl)piperazin-1-yl)-4-oxobutanoate

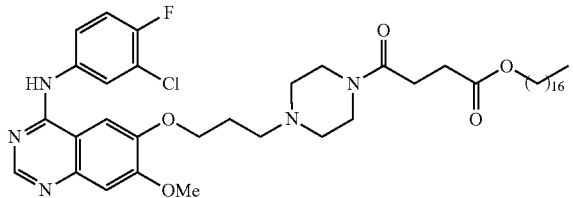

Analogue-24: octadecyl 4-(4-(3-(4-(3-chloro-4-fluorophenylamino)-7-methoxyquinazolin-6-yloxy)propyl)piperazin-1-yl)-4-oxobutanoate

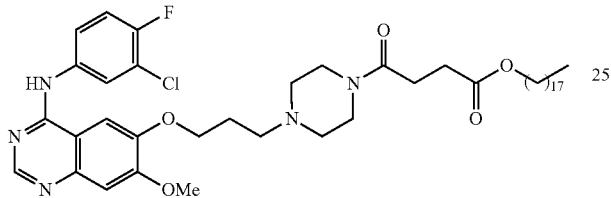

30

Analogue-25: nonadecyl 4-(4-(3-(4-(3-chloro-4-fluorophenylamino)-7-methoxyquinazolin-6-yloxy)propyl)piperazin-1-yl)-4-oxobutanoate

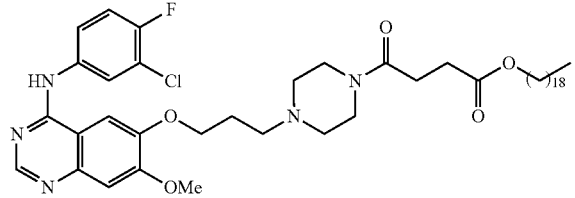

Analogue-26: icosyl 4-(4-(3-(4-(3-chloro-4-fluorophenylamino)-7-methoxyquinazolin-6-yloxy)propyl)piperazin-1-yl)-4-oxobutanoate

TABLE 2

Physical and chemical data of Analogue-8 to Analogue-26

| Analogue | Physical and chemical data |
|---|---|
| Analogue-8 (Yield: 40%) | $^1$H NMR (400 MHz, CDCl$_3$, δ): 8.65 (s, 1H), 7.86-7.84 (m, 1H), 7.52 (s, 1H), 7.40 (s, 1H), 7.25 (s, 1H), 7.18-7.14 (t, J = 8.7 Hz, 1H), 7.11 (s, 1H), 4.19-4.10 (m, 4H), 3.99 (s, 3H), 3.61 (b, 2H), 3.49-3.47 (m, 2H), 2.66-2.57 (m, 6H), 2.49-2.47 (m, 2H), 2.44-2.42 (m, 2H), 2.12-2.08 (m, 2H), 1.26-1.23 (t, J = 7.1 Hz, 3H); $^{13}$C NMR (100.6 MHz, CDCl$_3$, δ): 173.3, 169.7, 156.4, 155.9, 155.1, 153.4, 148.9, 147.3, 135.5, 124.2, 121.8, 121.8, 116.6, 116.4, 109.0, 107.6, 101.2, 67.4, 60.6, 56.1, 54.6, 53.1, 52.7, 45.1, 41.6, 29.2, 27.8, 26.2, 14.1; IR (KBr): 3346, 2933, 2824, 1731, 1625, 1579, 1501, 1472, 1429, 1218, 1176, 1005, 859 cm$^{-1}$; MS m/z: 574.2 (M$^+$, 14.8), 154.1 (61.3), 136.1 (63.7), 55.1 (100); HRFAB (m/z): [M]$^+$ calculated for C$_{28}$H$_{33}$ClFN$_5$O$_5$, 573.2154; found, 573.2166. |
| Analogue-9 (Yield: 37%) | $^1$H NMR (400 MHz, CDCl$_3$, δ): 8.62 (s, 1H), 8.32 (s, 1H), 7.79-7.7 (m, 1H), 7.53-7.51 (m, 1H), 7.37 (s, 1H), 7.18 (s, 1H), 7.11-7.07 (t, J = 8.7 Hz, 1H), 4.07-4.04 (t, J = 6.4 Hz 2H), 4.00-3.96 (t, J = 6.7 Hz 2H), 3.90 (s, 3H), 3.53 (b, 2H), 3.42-3.39 (m, 2H), 2.62-2.58 (m, 4H), 2.50-2.47 (t, J = 6.9 Hz, 2H), 2.41-2.39 (m, 2H), 2.34-2.31 (m, 2H), 2.02-1.99 (J = 6.7 Hz, 2H), 1.61-1.56 (m, 2H), 0.89-0.86 (t, J = 7.4 Hz, 3H); $^{13}$C NMR (100.6 MHz, CDCl$_3$, δ): 173.3, 169.7, 156.5, 155.8, 155.1, 153.3, 148.9, 147.2, 135.6, 124.2, 121.9, 121.8, 120.8, 120.7, 116.5, 116.3, 109.1, 107.5, 101.3, 67.3, 66.3, 56.1, 54.6, 53.1, 52.6, 45.1, 41.6, 29.1, 27.8, 26.3, 21.9, 14.1; IR (KBr): 3326, 2964, 2820, 1731, 1625, 1579, 1501, 1471, 1428, 1217, 1174, 1004, 859 cm$^{-1}$; MS m/z: 588.3 (M$^+$, 13.94), 413.3 (24.7), 143.2 (48.6), 55.1 (100); HRFAB (m/z): [M]$^+$ calculated for C$_{29}$H$_{35}$ClFN$_5$O$_5$, 587.2311; found, 587.2300. |
| Analogue-10 (Yield: 42%) | $^1$H NMR (400 MHz, CDCl$_3$, δ): 8.63 (s, 1H), 8.01 (s, 1H), 7.79-7.7 (m, 1H), 7.53-7.51 (m, 1H), 7.28 (s, 1H), 7.20 (s, 1H), 7.14-7.10 (t, J = 8.8 Hz, 1H), 4.13-4.09 (t, J = 6.4 Hz 2H), 4.06-4.03 (t, J = 6.7 Hz 2H), 3.94 (s, 3H), 3.57 (b, 2H), 3.46-3.43 (m, 2H), 2.63-2.59 (m, 4H), 2.55-2.52 (t, J = 6.9 Hz, 2H), 2.46-2.43 (m, 2H), 2.39-2.37 (m, 2H), 2.07-2.03 (t, J = 6.7 Hz, 2H), 1.59-1.55 (m, 2H), 1.36-1.30 (m, 2H), 0.91-0.87 (t, J = 7.4 Hz, 3H); $^{13}$C NMR (100.6 MHz, CDCl$_3$, δ): 173.3, 169.7, 156.3, 155.9, 155.2, 153.5, 153.3, 149.0, 147.3, 135.4, 124.2, 121.8, 121.7, 121.0, 120.8, 116.6, 116.4, 109.0, 107.6, 101.0, 67.2, 64.6, 56.1, 54.7, 53.1, 52.7, 45.1, |

TABLE 2-continued

Physical and chemical data of Analogue-8 to Analogue-26

| Analogue | Physical and chemical data |
|---|---|
| | 41.6, 30.5, 29.2, 27.8, 26.3, 19.1, 13.7; IR (KBr): 3327, 2956, 2820, 1731, 1624, 1579, 1501, 1471, 14289, 1218, 1173, 1005, 859 cm$^{-1}$; MS m/z: 602.3 (M$^+$, 22.2), 154.1 (21.3), 136.1 (29.7), 55.0 (100); HRFAB (m/z): [M]$^+$ calculated for C$_{30}$H$_{37}$ClFN$_5$O$_5$, 601.2467; found, 601.2456. |
| Analogue-11 (Yield: 47%) | $^1$H NMR (400 MHz, CDCl$_3$, δ): 8.62 (s, 1H), 8.32 (s, 1H), 7.79-7.7 (m, 1H), 7.53-7.51 (m, 1H), 7.37 (s, 1H), 7.18 (s, 1H), 7.11-7.07 (t, J = 8.8 Hz, 1H), 4.07-4.04 (t, J = 6.4 Hz 2H), 4.02-3.99 (t, J = 6.7 Hz 2H), 3.90 (s, 3H), 3.53 (b, 2H), 3.41-3.39 (m, 2H), 2.61-2.57 (m, 4H), 2.49-2.46 (t, J = 6.9 Hz, 2H), 2.40-2.38 (m, 2H), 2.33-2.31 (m, 2H), 2.02-2.00 (t, J = 6.7 Hz, 2H), 1.57-1.54 (m, 2H), 1.27-1.23 (m, 4H), 0.87-0.83 (t, J = 6.9 Hz, 3H); $^{13}$C NMR (100.6 MHz, CDCl$_3$, δ): 173.3, 169.7, 156.5, 155.8, 155.1, 153.3, 148.9, 147.2, 135.6, 124.2, 121.9, 121.8, 120.8, 120.7, 116.5, 116.3, 109.1, 107.5, 101.3, 67.3, 66.3, 56.1, 54.6, 53.1, 52.6, 45.1, 41.6, 29.1, 27.8, 26.3, 21.9, 14.1; IR (KBr): 3326, 2959, 2820, 1731, 1625, 1579, 1500, 1471, 1428, 1217, 1174, 1005, 858 cm$^{-1}$; MS m/z: 616.3 (M$^+$, 58.9), 413.3 (31.2), 269.3 (30.7), 154.1 (54.9), 143.2 (64.3), 136.1 (48.7), 57.0 (100); HRFAB (m/z): [M]$^+$ calculated for C$_{31}$H$_{39}$ClFN$_5$O$_5$, 615.2624; found, 615.2613. |
| Analogue-12 (Yield: 42%) | $^1$H NMR (400 MHz, CDCl$_3$, δ): 8.63 (s, 1H), 8.04 (s, 1H), 7.83 (s, 1H), 7.53-7.51 (m, 1H), 7.30 (s, 1H), 7.20 (s, 1H), 7.14-7.09 (t, J = 8.8 Hz, 1H), 4.12-4.09 (t, J = 6.4 Hz 2H), 4.04-4.01 (t, J = 6.7 Hz 2H), 3.93 (s, 3H), 3.57 (b, 2H), 3.46-3.43 (m, 2H), 2.63-2.59 (m, 4H), 2.55-2.51 (t, J = 6.9 Hz, 2H), 2.45-2.43 (m, 2H), 2.39-2.36 (m, 2H), 2.06-2.03 (t, J = 6.7 Hz, 2H), 1.59-1.55 (m, 2H), 1.28-1.24 (m, 8H), 0.87-0.84 (t, J = 6.7 Hz, 3H); $^{13}$C NMR (100.6 MHz, CDCl$_3$, δ): 173.3, 169.7, 156.3, 155.9, 155.1, 153.4, 153.4, 149.0, 147.4, 135.5, 124.2, 121.8, 121.7, 121.0, 120.8, 116.6, 116.4, 109.0, 107.7, 101.1, 67.4, 64.9, 56.1, 54.7, 53.1, 52.7, 45.1, 41.6, 31.4, 29.2, 28.5, 27.8, 26.2, 25.5, 22.5, 13.7; IR (KBr): 3333, 2930, 2858, 1731, 1625, 1579, 1500, 1476, 1428, 1217, 1173, 1005, 859 cm$^{-1}$; MS m/z: 630.3 (M$^+$, 100), 413.3 (36.0), 154.1 (91.2), 136.1 (96.8), 55.1 (91.8); HRFAB (m/z): [M]$^+$ calculated for C$_{32}$H$_{41}$ClFN$_5$O$_5$, 629.2780; found, 629.2783. |
| Analogue-13 (Yield: 47%) | $^1$H NMR (400 MHz, CDCl$_3$, δ): 8.62 (s, 1H), 8.32 (s, 1H), 7.79-7.7 (m, 1H), 7.53-7.51 (m, 1H), 7.37 (s, 1H), 7.18 (s, 1H), 7.11-7.07 (t, J = 8.8 Hz, 1H), 4.07-4.04 (t, J = 6.4 Hz 2H), 4.02-3.99 (t, J = 6.7 Hz 2H), 3.90 (s, 3H), 3.53 (b, 2H), 3.41-3.39 (m, 2H), 2.61-2.57 (m, 4H), 2.49-2.46 (t, J = 6.9 Hz, 2H), 2.40-2.38 (m, 2H), 2.33-2.31 (m, 2H), 2.02-2.00 (t, J = 6.7 Hz, 2H), 1.57-1.54 (m, 2H), 1.27-1.23 (m, 8H), 0.87-0.83 (t, J = 6.9 Hz, 3H); $^{13}$C NMR (100.6 MHz, CDCl$_3$, δ): 173.3, 169.7, 156.5, 155.8, 155.1, 153.3, 148.9, 147.2, 135.6, 124.2, 121.9, 121.8, 120.8, 120.7, 116.5, 116.3, 109.1, 107.5, 101.3, 67.3, 66.3, 56.1, 54.6, 53.1, 52.6, 45.1, 41.6, 29.1, 27.8, 26.3, 21.9, 14.1; IR (KBr): 3330, 2929, 2857, 1731, 1624, 1578, 1500, 1471, 1428, 1217, 1172, 1005, 859 cm$^{-1}$; MS m/z: 644.3 (M$^+$, 4.9), 154.1 (4.6), 136.1 (5.3), 55.1 (100); HRFAB (m/z): [M]$^+$ calculated for C$_{33}$H$_{43}$ClFN$_5$O$_5$, 643.2937; found, 643.2957. |
| Analogue-14 (Yield: 41%) | $^1$H NMR (400 MHz, CDCl$_3$, δ): 8.61 (s, 1H), 8.32 (s, 1H), 7.83 (s, 1H), 7.53-7.51 (m, 1H), 7.36 (s, 1H), 7.18 (s, 1H), 7.11-7.07 (t, J = 8.8 Hz, 1H), 4.08-4.05 (t, J = 6.4 Hz 2H), 4.03-3.99 (t, J = 6.7 Hz 2H), 3.91 (s, 3H), 3.54 (b, 2H), 3.43-3.41 (m, 2H), 2.62-2.58 (m, 4H), 2.51-2.48 (t, J = 6.9 Hz, 2H), 2.41-2.40 (m, 2H), 2.35-2.33 (m, 2H), 2.03-2.00 (t, J = 6.7 Hz, 2H), 1.56-1.54 (m, 2H), 1.26-1.23 (m, 10H), 0.87-0.83 (t, J = 6.7 Hz, 3H); $^{13}$C NMR (100.6 MHz, CDCl$_3$, δ): 173.3, 169.7, 156.4, 155.8, 155.1, 153.4, 153.3, 148.9, 147.2, 135.5, 124.2, 121.9, 121.8, 120.9, 120.7, 116.5, 116.3, 109.1, 107.4, 101.3, 67.3, 64.9, 56.1, 54.6, 53.1, 52.6, 45.1, 41.6, 31.7, 29.1, 29.1, 28.5, 27.8, 26.2, 25.8, 22.6, 14.0; IR (KBr): 3328, 2928, 2856, 1731, 1625, 1578, 1500, 1471, 1428, 1217, 1172, 1005, 859 cm$^{-1}$; MS m/z: 658.3 (M$^+$, 5.50), 154.1 (4.7), 136.1 (8.4), 55.1 (100); HRFAB (m/z): [M]$^+$ calculated for C$_{34}$H$_{45}$ClFN$_5$O$_5$, 657.3093; found, 657.3099. |
| Analogue-15 (Yield: 36%) | $^1$H NMR (400 MHz, CDCl$_3$, δ): 8.63 (s, 1H), 8.09 (s, 1H), 7.82-7.79 (m, 1H), 7.53-7.51 (m, 1H), 7.31 (s, 1H), 7.20 (s, 1H), 7.13-7.09 (t, J = 8.8 Hz, 1H), 4.10-4.07 (t, J = 6.4 Hz 2H), 4.04-4.00 (t, J = 6.8 Hz 2H), 3.93 (s, 3H), 3.55 (b, 2H), 3.43-3.42 (m, 2H), 2.62-2.58 (m, 4H), 2.53-2.49 (t, J = 6.9 Hz, 2H), 2.42 (b, 2H), 2.36-2.35 (m, 2H), 2.05-2.01 (t, J = 6.7 Hz, 2H), 1.58-1.55 (m, 2H), 1.23 (b, 12H), 0.87-0.84 (t, J = 6.7 Hz, 3H); $^{13}$C NMR (100.6 MHz, CDCl$_3$, δ): 173.4, 169.7, 156.3, 155.9, 155.1, 153.4, 149.0, 147.4, 135.5, 124.2, 121.8, 121.8, 120.7, 116.6, 116.4, 109.0, 107.6, 101.1, 67.3, 64.9, 56.1, 54.6, 53.1, 52.7, 45.1, 41.6, 31.8, 29.4, 29.2, 29.2, 28.5, 27.8, 26.3, 25.8, 22.6, 14.1; IR (KBr): 3330, 2926, 2855, 1731, 1624, 1578, 1500, 1471, 1428, 1217, 1176, 1005, 858 cm$^{-1}$; MS m/z: 672.3 (M$^+$, 100), 371.3 (37.8), 325.3 (48.7), 154.1 (23.3), 136.1 (25.0), 55.1 (60.1); HRFAB (m/z): [M]$^+$ calculated for C$_{35}$H$_{47}$ClFN$_5$O$_5$, 671.32504; found, 671.3248. |
| Analogue-16 (Yield: 37%) | $^1$H NMR (400 MHz, CDCl$_3$, δ): 8.63 (s, 1H), 8.14 (s, 1H), 7.82-7.80 (m, 1H), 7.53-7.51 (m, 1H), 7.33 (s, 1H), 7.19 (s, 1H), 7.12-7.08 (t, J = 8.7 Hz, 1H), 4.10-4.07 (t, J = 6.4 Hz, 2H), 4.03-4.00 (t, J = 6.8 Hz, 2H), 3.92 (s, 3H), 3.55 (b, 2H), 3.43-3.41 (m, 2H), 2.62-2.58 (m, 4H), 2.52-2.49 (t, |

TABLE 2-continued

Physical and chemical data of Analogue-8 to Analogue-26

| Analogue | Physical and chemical data |
|---|---|
| | J = 6.9 Hz, 2H), 2.42 (b, 2H), 2.36-2.34 (m, 2H), 2.04-2.01 (t, J = 6.7 Hz, 2H), 1.58-1.55 (m, 2H), 1.29-1.23 (b, 14H), 0.87-0.84 (t, J = 6.7 Hz, 3H); $^{13}$C NMR (100.6 MHz, CDCl$_3$, δ): 173.3, 169.7, 156.4, 155.8, 155.1, 153.4, 149.0, 147.4, 135.5, 135.5, 124.2, 121.8, 121.8, 120.9, 120.7, 116.6, 116.3, 109.1, 107.6, 101.2, 67.3, 64.9, 56.1, 54.6, 53.1, 52.7, 45.1, 41.6, 31.8, 29.5, 29.2, 29.2, 28.5, 27.8, 26.3, 25.8, 22.6, 14.1; IR (KBr): 3330, 2926, 2854, 1732, 1624, 1578, 1500, 1471, 1428, 1217, 1171, 1005, 858 cm$^{-1}$; MS m/z: 686.3 (M$^+$, 6.41), 154.1 (12.3), 136.1 (22.7), 55.0 (100); HRFAB (m/z): [M]$^+$ calculated for C$_{36}$H$_{49}$ClFN$_5$O$_5$, 685.3406; found, 685.3406. |
| Analogue-17 (Yield: 44%) | $^1$H NMR (400 MHz, CDCl$_3$, δ): 8.65 (s, 1H), 7.86-7.84 (m, 1H), 7.54-7.52 (m, 1H), 7.52 (s, 1H), 7.23 (s, 1H), 7.17-7.13 (t, J = 8.7 Hz, 1H), 7.12 (s, 1H), 4.16-4.13 (t, J = 6.4 Hz, 2H), 4.07-4.04 (t, J = 6.8 Hz, 2H), 3.98 (s, 3H), 3.60 (b, 2H), 3.48 (b, 2H), 2.65-2.60 (m, 4H), 2.58-2.55 (t, J = 7.1 Hz, 2H), 2.47 (b, 2H), 2.43-2.42 (m, 2H), 2.10-2.07 (t, J = 6.7 Hz, 2H), 1.62-1.58 (m, 2H), 1.25 (b, 16H), 0.89-0.85 (t, J = 6.7 Hz, 3H); $^{13}$C NMR (100.6 MHz, CDCl$_3$, δ): 173.3, 169.7, 156.4, 155.8, 155.1, 153.3, 149.0, 147.3, 135.5, 124.1, 121.8, 121.7, 120.9, 120.7, 116.6, 116.3, 109.1, 107.6, 101.2, 67.3, 64.9, 56.1, 54.6, 53.1, 52.7, 45.1, 41.6, 31.8, 29.5, 29.5, 29.3, 29.2, 28.5, 27.8, 26.3, 25.8, 22.6, 14.1; IR (KBr): 3331, 2925, 2854, 1732, 1624, 1578, 1500, 1470, 1428, 1217, 1171, 1005, 858 cm$^{-1}$. MS m/z: 700.3 (M$^+$, 11.0), 87.2 (20.9), 52.8 (100). HRFAB (m/z): [M − H]$^+$ calculated for C$_{37}$H$_{51}$ClFN$_5$O$_5$, 699.3563; found, 699.3559. |
| Analogue-18 (Yield: 39%) | $^1$H NMR (400 MHz, CDCl$_3$, δ): 8.65 (s, 1H), 7.86-7.84 (m, 1H), 7.54-7.51 (m, 2H), 7.24 (s, 1H), 7.17-7.13 (m, 2H), 4.18-4.15 (t, J = 6.4 Hz, 2H), 4.07-4.03 (t, J = 6.8 Hz, 2H), 3.98 (s, 3H), 3.61 (b, 2H), 3.48 (b, 2H), 2.65-2.56 (m, 6H), 2.48 (b, 2H), 2.44-2.42 (m, 2H), 2.11-2.08 (t, J = 6.7 Hz, 2H), 1.61-1.58 (m, 2H), 1.32-1.25 (b, 18H), 0.89-0.85 (t, J = 6.7 Hz, 3H). $^{13}$C NMR (100.6 MHz, CDCl$_3$, δ): 173.3, 169.8, 156.3, 155.2, 153.5, 153.4, 149.0, 147.3, 135.4, 124.2, 121.8, 121.7, 121.0, 120.8, 116.6, 116.4, 109.0, 107.8, 101.2, 67.5, 64.9, 56.1, 54.7, 53.2, 52.7, 45.1, 41.6, 31.9, 29.6, 29.5, 29.3, 29.2, 28.6, 27.8, 26.2, 25.9, 22.7, 14.1. IR (KBr): 3672, 2925, 2854, 1732, 1625, 1578, 1500, 1470, 1429, 1217 cm$^{-1}$. MS m/z: 714.3 (M$^+$, 3.4), 551.4 (1.5), 71.7 (49.1), 52.8 (100). HRFAB (m/z): [M]$^+$ calculated for C$_{38}$H$_{53}$ClFN$_5$O$_5$, 713.3719; found, 713.3717. |
| Analogue-19 (Yield: 40%) | $^1$H NMR (400 MHz, CDCl$_3$, δ): 8.63 (s, 1H), 7.98 (s, 1H), 7.81-7.80 (m, 1H), 7.53-7.51 (m, 1H), 7.29 (s, 1H), 7.20 (s, 1H), 7.14-7.09 (t, J = 8.7 Hz, 1H), 4.11-4.08 (t, J = 6.4 Hz, 2H), 4.04-4.01 (t, J = 6.8 Hz, 2H), 3.93 (s, 3H), 3.56 (b, 2H), 3.43 (b, 2H), 2.63-2.58 (m, 4H), 2.53-2.50 (t, J = 6.9 Hz, 2H), 2.42 (b, 2H), 2.36 (m, 2H), 2.05-2.02 (t, J = 6.7 Hz, 2H), 1.59-1.55 (m, 2H), 1.23 (b, 20H), 0.88-0.84 (t, J = 6.7 Hz, 3H); $^{13}$C NMR (100.6 MHz, CDCl$_3$, δ): 173.3, 169.7, 156.5, 155.7, 155.1, 153.3, 148.9, 147.3, 135.7, 124.2, 121.9, 121.8, 120.8, 120.6, 116.5, 116.2, 109.2, 107.4, 101.5, 67.3, 64.9, 56.0, 54.6, 53.1, 52.6, 45.1, 41.6, 31.8, 29.6, 29.5, 29.4, 29.3, 29.2, 28.5, 27.8, 26.3, 25.8, 22.6, 14.0; IR (KBr): 3334, 2925, 2854, 1733, 1624, 1578, 1500, 1470, 1428, 1217, 1172, 1005, 858 cm$^{-1}$. MS m/z: 728.3 (M$^+$, 15.2), 528.1 (1.2), 87.1 (19.2), 53.7 (100). HRFAB (m/z): [M]$^+$ calculated for C$_{39}$H$_{55}$ClFN$_5$O$_5$, 727.3876; found, 727.3873. |
| Analogue-20 (Yield: 41%) | $^1$H NMR (400 MHz, CDCl$_3$, δ): 8.64 (s, 1H), 7.83-7.81 (m, 2H), 7.51 (m, 1H), 7.25 (s, 1H), 7.22 (s, 1H), 7.15-7.10 (t, J = 8.7 Hz, 1H), 4.13-4.10 (t, J = 6.4 Hz, 2H), 4.05-4.02 (t, J = 6.8 Hz, 2H), 3.95 (s, 3H), 3.57 (b, 2H), 3.44 (b, 2H), 2.63-2.58 (m, 4H), 2.55-2.52 (t, J = 6.9 Hz, 2H), 2.44 (b, 2H), 2.38 (m, 2H), 2.07-2.04 (t, J = 6.7 Hz, 2H), 1.60-1.56 (m, 2H), 1.28-1.24 (b, 22H), 0.88-0.85 (t, J = 6.7 Hz, 3H); $^{13}$C NMR (100.6 MHz, CDCl$_3$, δ): 173.4, 169.8, 156.5, 155.8, 155.2, 153.4, 149.0, 147.3, 135.7, 124.2, 121.9, 121.8, 120.9, 120.7, 116.6, 116.3, 109.2, 107.5, 101.5, 76.7, 67.4, 65.0, 56.1, 54.7, 53.2, 52.7, 45.1, 41.6, 32.0, 29.6, 29.6, 29.5, 29.3, 29.2, 29.2, 28.6, 27.8, 25.9, 22.7, 14.1; IR (KBr): 3332, 2925, 2854, 1732, 1626, 1579, 1501, 1471, 1429, 1218 cm$^{-1}$; MS m/z: 742.3 (M$^+$, 57.8), 423.4 (31.2), 395.3 (29.4), 320.1 (28.6), 209.2 (11.7), 140.1 (12.9), 109.0 (13.4), 58.7 (59.8), 52.8 (100); HRFAB (m/z): [M]$^+$ calculated for C$_{40}$H$_{57}$ClFN$_5$O$_5$, 741.4032; found, 741.4046. |
| Analogue-21 (Yield: 46%) | $^1$H NMR (400 MHz, CDCl$_3$, δ): 8.65 (s, 1H), 7.85-7.83 (m, 1H), 7.53-7.51 (m, 2H), 7.24 (s, 1H), 7.17-7.13 (m, 2H), 4.18-4.14 (t, J = 6.4 Hz, 2H), 4.07-4.03 (t, J = 6.8 Hz, 2H), 3.98 (s, 3H), 3.60 (b, 2H), 3.47-3.46 (b, 2H), 2.64-2.55 (m, 6H), 2.47 (b, 2H), 2.43-2.40 (m, 2H), 2.10-2.07 (t, J = 6.7 Hz, 2H), 1.61-1.58 (m, 2H), 1.24 (b, 24H), 0.89-0.85 (t, J = 6.7 Hz, 3H); $^{13}$C NMR (100.6 MHz, CDCl$_3$, δ): 173.3, 169.7, 156.5, 155.7, 155.1, 153.3, 148.9, 147.2, 135.7, 124.1, 121.9, 121.8, 120.8, 120.6, 116.5, 116.2, 109.1, 107.4, 101.6, 76.7, 67.3, 64.9, 64.8, 56.0, 54.6, 53.1, 52.6, 45.1, 41.6, 31.8, 29.6, 29.6, 29.5, 29.4, 29.3, 29.2, 28.5, 27.8, 26.2, 25.8, 22.6, 14.1; IR (KBr): 3337, 2924, 2853, 1733, 1625, 1578, 1500, 1469, 1429, 1217, 1172, 1005, 859 cm$^{-1}$. MS m/z: 756.3 (M$^+$, 38.3), 437.3 (23.7), 409.3 (20.6), 320.1 (21.7), 109.0 (13.6), 58.7 (48.8), 53.7 (100). HRFAB (m/z): [M]$^+$calculated for C$_{41}$H$_{59}$ClFN$_5$O$_5$, 755.4189; found, 755.4190. |

TABLE 2-continued

Physical and chemical data of Analogue-8 to Analogue-26

| Analogue | Physical and chemical data |
| --- | --- |
| Analogue-22 (Yield: 39%) | $^1$H NMR (400 MHz, CDCl$_3$, δ): 8.65 (s, 1H), 7.85-7.83 (m, 1H), 7.54-7.52 (m, 2H), 7.24 (s, 1H), 7.17-7.13 (m, 2H), 4.17-4.14 (t, J = 6.4 Hz, 2H), 4.06-4.03 (t, J = 6.8 Hz, 2H), 3.97 (s, 3H), 3.60 (b, 2H), 3.47 (b, 2H), 2.64-2.55 (m, 6H), 2.47 (b, 2H), 2.41 (b, 2H), 2.10-2.07 (t, J = 6.7 Hz, 2H), 1.61-1.58 (m, 2H), 1.24 (b, 26H), 0.89-0.85 (t, J = 6.7 Hz, 3H); $^{13}$C NMR (100.6 MHz, CDCl$_3$, δ): 173.3, 169.8, 156.5, 155.7, 155.1, 153.3, 153.2, 148.9, 147.2, 135.7, 124.1, 121.8, 121.8, 120.8, 120.6, 116.4, 116.2, 109.1, 107.4, 101.7, 67.3, 64.9, 56.0, 54.6, 53.1, 52.6, 45.1, 41.6, 31.8, 29.6, 29.6, 29.6, 29.5, 29.4, 29.3, 29.2, 28.5, 27.8, 26.2, 25.8, 22.6, 14.0 IR (KBr): 3334, 2924, 2853, 1732, 1625, 1579, 1501, 1470, 1428, 1218, 1172, 1005, 859 cm$^{-1}$. MS m/z: 770.3 (M$^+$, 22.7), 71.7 (29.7), 53.7 (100). HRFAB (m/z): [M]$^+$ calculated for C$_{42}$H$_{61}$ClFN$_5$O$_5$, 769.4345; found, 769.4327. |
| Analogue-23 (Yield: 37%) | $^1$H NMR (400 MHz, CDCl$_3$, δ): 8.63 (s, 1H), 8.13 (s, 1H), 7.81-7.79 (m, 1H), 7.53-7.51 (m, 1H), 7.32 (s, 1H), 7.19 (s, 1H), 7.12-7.08 (t, J = 8.7 Hz, 1H), 4.08 (b, 2H), 4.03-4.00 (t, J = 6.8 Hz, 2H), 3.92 (s, 3H), 3.55 (b, 2H), 3.42 (b, 2H), 2.62-2.58 (m, 4H), 2.52-2.49 (t, J = 6.9 Hz, 2H), 2.42 (b, 2H), 2.35 (m, 2H), 2.04-2.01 (t, J = 6.7 Hz, 2H), 1.58-1.55 (m, 2H), 1.28-1.23 (b, 28H), 0.88-0.84 (t, J = 6.7 Hz, 3H); $^{13}$C NMR (100.6 MHz, CDCl$_3$, δ): 173.3, 173.1, 169.7, 156.4, 155.8, 155.2, 153.3, 149.0, 147.3, 135.6, 124.1, 121.8, 121.7, 120.9, 120.7, 116.5, 116.3, 109.1, 107.6, 101.4, 67.4, 64.9, 56.0, 54.6, 53.1, 52.6, 45.1, 41.7, 31.8, 29.6, 29.6, 29.5, 29.4, 29.3, 29.2, 28.5, 27.8, 26.3 25.8, 22.6, 14.0; IR (KBr): 3334, 2924, 2853, 1732, 1625, 1578 1501, 1470, 1429 1218, 1172, 1005, 859 cm$^{-1}$. MS m/z: 784.3 (M$^+$, 83.0), 465.3 (50.3), 437.4 (40.2), 320.1 (18.7), 58.7 (70.2), 53.7 (100). HRFAB (m/z): [M]$^+$ calculated for C$_{43}$H$_{63}$ClFN$_5$O$_5$, 783.4502; found, 783.4487. |
| Analogue-24 (Yield: 34%) | $^1$H NMR (400 MHz, CDCl$_3$, δ): 8.62 (s, 1H), 8.14 (b, 1H), 7.82-7.81 (m, 1H), 7.54-7.52 (m, 1H), 7.32 (s, 1H), 7.20 (s, 1H), 7.13-7.08 (t, J = 8.7 Hz, 1H), 4.09-4.08 (b, 2H), 4.04-4.01 (t, J = 6.8 Hz, 2H), 3.92 (s, 3H), 3.57 (b, 2H), 3.44 (b, 2H), 2.62-2.58 (m, 4H), 2.54-2.51 (t, J = 6.9 Hz, 2H), 2.44 (b, 2H), 2.37 (b, 2H), 2.05-2.02 (t, J = 6.7 Hz, 2H), 1.57-1.55 (m, 2H), 1.23 (b, 30H), 0.87-0.84 (t, J = 6.7 Hz, 3H); $^{13}$C NMR (100.6 MHz, CDCl$_3$, δ): 173.3, 169.8, 156.4, 155.8, 155.1, 153.3, 153.2, 148.9, 147.1, 135.7, 124.1, 121.8, 121.7, 120.8, 120.6, 116.5, 116.3, 109.1, 107.4, 101.6, 76.7, 67.4, 64.9, 56.0, 54.6, 53.1, 52.6, 45.0, 41.5, 31.8, 29.6, 29.6, 29.5, 29.4, 29.3, 29.2, 28.5, 27.7, 26.2 25.8, 22.6, 14.0. IR (KBr): 3319, 2924, 2853, 1733, 1626, 1579, 1501, 1471, 1429 1218 cm$^{-1}$. MS m/z: 798.3 (M$^+$, 58.2), 479.4 (22.9), 451.4 (22.4), 320.1 (20.4), 124.4 (15.8), 53.7 (100). HRFAB (m/z): [M]$^+$ calculated for C$_{44}$H$_{65}$ClFN$_5$O$_5$, 797.4658; found, 797.4664. |
| Analogue-25 (Yield: 37%) | $^1$H NMR (400 MHz, CDCl$_3$, δ): 8.64 (s, 1H), 7.83-7.80 (m, 2H), 7.53-7.50 (m, 1H), 7.21 (s, 1H), 7.14-7.10 (t, J = 8.7 Hz, 1H), 4.11-4.10 (b, 2H), 4.05-4.01 (t, J = 6.8 Hz, 2H), 3.94 (s, 3H), 3.57 (b, 2H), 3.44 (b, 2H), 2.63-2.59 (m, 4H), 2.54-2.51 (t, J = 6.9 Hz, 2H), 2.43 (b, 2H), 2.37 (b, 2H), 2.06-2.03 (t, J = 6.7 Hz, 2H), 1.59-1.56 (m, 2H), 1.26-1.24 (b, 32H), 0.88-0.85 (t, J = 6.7 Hz, 3H); $^{13}$C NMR (100.6 MHz, CDCl$_3$, δ): 173.3, 169.8, 156.5, 155.7, 155.1, 153.3, 148.9, 147.2, 135.7, 124.1, 121.8, 121.8, 120.7, 120.5, 116.4, 116.2, 109.2, 107.4, 101.7, 67.3, 64.9, 56.0, 54.6, 53.1, 52.6, 45.1, 41.6, 31.8, 29.6, 29.5, 29.4, 29.3, 29.2, 28.5, 27.7, 26.3 25.8, 22.6, 14.0; IR (KBr): 3335 2924, 2853, 1733 1625, 1578 1501, 1470, 1429, 1217, 1172, 1005, 858 cm$^{-1}$. MS m/z: 812.3 (M$^+$, 52.1), 493.4 (38.3), 465.3 (28.6), 320.1 (30.6), 60.3 (50.2), 53.7 (100). HRFAB (m/z): [M]$^+$ calculated for C$_{45}$H$_{67}$ClFN$_5$O$_5$, 811.4815; found, 811.4828. |
| Analogue-26 (Yield: 38%) | $^1$H NMR (400 MHz, CDCl$_3$, δ): 8.63 (s, 1H), 7.93 (s, 1H), 7.83-7.82 (m, 1H), 7.55-7.52 (m, 1H), 7.26 (s, 1H), 7.21 (s, 1H), 7.14-7.10 (t, J = 8.7 Hz, 1H), 4.13-4.10 (t, J = 6.4 Hz, 2H), 4.05-4.02 (t, J = 6.8 Hz, 2H), 3.95 (s, 3H), 3.57 (b, 2H), 3.45 (b, 2H), 2.63-2.59 (m, 4H), 2.55-2.51 (t, J = 6.9 Hz, 2H), 2.44 (b, 2H), 2.37 (m, 2H), 2.06-2.03 (t, J = 6.7 Hz, 2H), 1.59-1.54 (m, 2H), 1.28-1.23 (b, 34H), 0.88-0.84 (t, J = 6.7 Hz, 3H); $^{13}$C NMR (100.6 MHz, CDCl$_3$, δ): 173.2, 169.7, 156.5, 155.7, 155.1, 153.2, 148.9, 147.2, 135.8, 124.1, 121.8, 121.8, 120.7, 120.5, 116.4, 116.2, 109.2, 107.3, 101.8, 67.3, 64.9, 56.0, 54.6, 53.1, 52.6, 45.1, 41.6, 31.8, 29.6, 29.5, 29.4, 29.3, 29.2, 28.5, 27.7, 26.3 25.8, 22.6, 14.0; IR (KBr): 3329, 2918, 2850, 1732, 1625, 1579, 1501, 1470, 1429, 1217, 1174, 1005, 858 cm$^{-1}$; MS m/z: 826.3 (M$^+$, 37.6), 507.4 (28.2), 479.4 (20.6), 150.1 (13.8), 109.0 (14.1), 58.7 (69.8), 52.8 (100); HRFAB (m/z): [M]$^+$ calculated for C$_{46}$H$_{69}$ClFN$_5$O$_5$, 825.4971; found, 825.4968. |

Example 2

Toxicity Effect of Irresa Analogues Against Cancer Cells

First of all, in order to evaluate the toxicity effect of the synthesized Irresa Analogues of the present invention (hereinafter referred to Analogues) against cancer cells, RKO cell line, BFTC905 cell line and A549 cell line were treated with the synthesized Analogues in Example 1 of the present invention.

The above cell lines were plated in 96-well plates at a density of $1 \times 10^4$ cells/well for 16 to 20 hours. Then, the cell lines were treated with or without Iressa or Analogues, including Analogue-1 to Analogue-26, for 24 hours in RPMI-1640 medium. After drug treatment, the cell lines were washed with phosphate-buffered saline (hereinafter referred to PBS), and were replaced with fresh complete RPMI-1640 medium for 2 days. Thereafter, the medium was replaced and the cells were incubated with 0.5 mg/ml of 3-(4,5-dimethylthiazol-2-yl)-2,5-diphenyltetrazolium bromide reagent (hereinafter referred to MTT, Sigma Chemical Co., St. Louis, Mo.) in complete RPMI-1640 medium for 4 hours. The viable cells converted MTT to formazan that generates a blue-purple color when dissolved in dimethyl sulfoxide (hereinafter referred to DMSO). The intensity of formazan was measured at 565 nm using a plate reader (VERSAmax, Molecular Dynamics, Sunnyvale, Calif.). The relative percentage of cell viability was calculated by dividing the absorbance of treated cells by that of the control in each experiment.

Figure 1B:
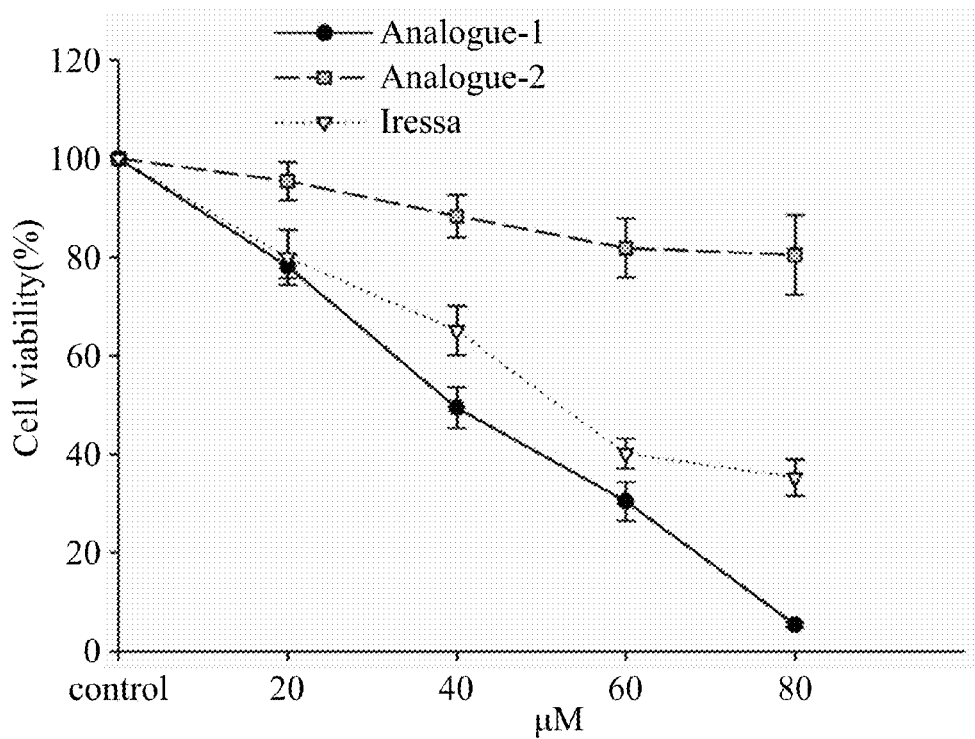

As shown in FIGS. 1A and 1B, the results of cell viability show that Analogue-1 is more effective on cell death of RKO cells and BFTC905 cells than Iressa. However, in comparison with Iressa and Analogue-1, Analogue-2 has no toxicity effect on RKO cells but has minor toxicity effect on BFTC905 cells. Therefore, it can be confirmed from the above results that the end of the morpholino group of Analogues should be bound with ester group. The following designs of synthesizing Analogue-3 to Analogue-7 and Analogue-26 to Analogue-44 were based on the structure of Analogue-1.

As shown in Table. 3, the results of cell viability of Analogue-3 to Analogue-7 show that: in comparison with Iressa, there is no significant toxicity effect on A549 cell line, when the number of carbon chain between two carboxylic acid of Analogue-1 is increased. (The carbon chain number is increasing from 1 to 5 respectively for Analogue 3 to Analogue 7.) As shown in Table. 3, the results of cell viability of Analogue-8 to Analogue-26 show that: in comparison with Iressa, there is a similar or significant toxicity effect on A549 cell line, when the number of carbon chain at the end of the morpholino of Analogue-1 is increased. (The carbon chain number is increasing from 1 to 19 respectively for Analogue 8 to Analogue 26.) Among these Analogues, Analogue-18 shows the best toxicity effect when A549 cell line was treated with 40 µM Analogue-18. The results show increased toxicity effect by 15-20 times. Therefore, it is confirm that Analogue-18, dodecyl 4-(4-(3-(4-(3-chloro-4-fluorophenylamino)-7-methoxyquinazolin-6-yloxy)propyl)piperazin-1-yl)-4-oxobutanoate, is a novel synthesized compound for treating lung cancer. The following examples determine the mechanism of inhibiting lung cancers for Analogue-18.

TABLE 3

The cell viability results of treatments with Iressa and Analogues in various concentrations.

| Analogue number | 0(µM) | 10 (µM) | 20 (µM) | 40 (µM) | 60 (µM) | 80 (µM) |
|---|---|---|---|---|---|---|
| Iressa | 100% | 86.7% ± 4.6 | 82.1% ± 5.6 | 74.3% ± 4.0 | 64.6% ± 3.0 | 60.8% ± 8.5 |
| 1 | 100% | 89.1% ± 4.5 | 85.6% ± 2.9 | 75.9% ± 5.4 | 74.4% ± 3.4 | 75.9% ± 5.3 |
| 3 | 100% | 99.9% ± 4.8 | 94.8% ± 2.8 | 91.9% ± 7.6 | 91.3% ± 7.9 | 89.8% ± 7.5 |
| 4 | 100% | 94.6% ± 3.5 | 90.4% ± 7.2 | 84.3% ± 3.7 | 83.3% ± 7.0 | 79.4% ± 5.9 |
| 5 | 100% | 95.2% ± 3.8 | 91.7% ± 1.5 | 90.1% ± 3.4 | 83.4% ± 5.6 | 82.4% ± 3.5 |
| 6 | 100% | 92.0% ± 5.1 | 94.3% ± 1.8 | 90.7% ± 5.5 | 88.5% ± 6.3 | 88.9% ± 4.4 |
| 7 | 100% | 90.3% ± 5.5 | 89.7% ± 4.2 | 85.8% ± 8.7 | 84.8% ± 8.7 | 80.9% ± 8.5 |
| 8 | 100% | 77.6% ± 2.0 | 70.0% ± 1.6 | 67.4% ± 2.0 | 61.6% ± 4.4 | 35.6% ± 10.4 |
| 9 | 100% | 95.1% ± 2.5 | 87.0% ± 1.5 | 80.9% ± 1.5 | 70.4% ± 4.4 | 23.4% ± 4.3 |
| 10 | 100% | 94.4% ± 1.6 | 86.0% ± 0.6 | 79.1% ± 3.0 | 64.1% ± 1.0 | 36.9% ± 2.4 |
| 11 | 100% | 87.1% ± 3.5 | 81.2% ± 3.7 | 63.6% ± 2.7 | 30.0% ± 3.7 | 18.2% ± 1.7 |
| 12 | 100% | 89.3% ± 0.5 | 85.1% ± 2.2 | 74.2% ± 3.2 | 63.6% ± 2.6 | 42.9% ± 3.4 |
| 13 | 100% | 89.1% ± 0.7 | 79.9% ± 0.4 | 59.1% ± 5.1 | 35.7% ± 1.1 | 27.2% ± 1.1 |
| 14 | 100% | 87.3% ± 1.3 | 80.0% ± 1.1 | 48.7% ± 7.9 | 26.0% ± 2.7 | 21.7% ± 2.1 |
| 15 | 100% | 90.0% ± 5.4 | 79.7% ± 1.1 | 17.9% ± 1.1 | 10.3% ± 1.8 | 7.8% ± 2.1 |
| 16 | 100% | 95.7% ± 2.1 | 88.2% ± 1.8 | 15.5% ± 5.9 | 3.9% ± 0.8 | 2.0% ± 0.3 |
| 17 | 100% | 93.4% ± 5.5 | 85.2% ± 4.0 | 12.0% ± 4.6 | 3.9% ± 2.0 | 2.8% ± 0.5 |
| 18 | 100% | 95.5% ± 2.3 | 86.8% ± 1.5 | 5.7% ± 2.0 | 2.0% ± 0.6 | 2.3% ± 0.7 |
| 19 | 100% | 93.7% ± 3.1 | 93.8% ± 5.6 | 71.1% ± 3.8 | 20.6% ± 5.5 | 6.8% ± 2.9 |
| 20 | 100% | 100.0% ± 1.5 | 92.3% ± 1.6 | 88.6% ± 0.9 | 84.9% ± 5.1 | 77.2% ± 1.1 |
| 21 | 100% | 92.0% ± 1.4 | 91.2% ± 1.5 | 85.5% ± 0.8 | 81.6% ± 1.4 | 81.1% ± 2.4 |
| 22 | 100% | 97.7% ± 1.1 | 91.7% ± 2.6 | 82.6% ± 3.7 | 80.0% ± 2.2 | 74.3% ± 4.4 |
| 23 | 100% | 95.7% ± 2.8 | 97.2% ± 2.0 | 85.2% ± 3.1 | 84.1% ± 5.3 | 83.2% ± 4.3 |
| 24 | 100% | 94.8% ± 2.6 | 90.5% ± 2.9 | 91.0% ± 0.7 | 87.2% ± 0.9 | 86.7% ± 1.1 |
| 25 | 100% | 94.5% ± 2.0 | 94.8% ± 3.7 | 92.3% ± 0.6 | 89.3% ± 1.2 | 88.4% ± 0.7 |
| 26 | 100% | 94.0% ± 2.0 | 90.8% ± 0.8 | 87.1% ± 1.6 | 86.9% ± 0.4 | 85.2% ± 0.6 |

Example 3

Analogue-18 has Toxicity Effect on Various Lung Cancer Cells

A549, H1299, CL3 and HFL1 cell lines (as the control group) were separately plated in 96-well plates at a density of $1 \times 10^4$ cells/well for 16 to 20 hours. Then the cells were treated with 0 to 40 µM Analogue-18 or Iressa for 24 hours in RPMI-1640 medium at 37° C. After drug treatment, the cells were washed with PBS and replaced with fresh complete RPMI-1640 medium for 2 days. Thereafter, the medium was replaced and the cells were incubated with 0.5 mg/mL of MTT reagent (Sigma Chemical Co., St. Louis, Mo.) in complete RPMI-1640 medium for 4 hours. The intensity of formazan was measured at 565 nm using a plate reader (VERSAmax, Molecular Dynamics, Sunnyvale, Calif.). The relative percentage of cell viability was calculated by dividing the absorbance of treated cells by that of the control in each experiment.

Figure 2A:
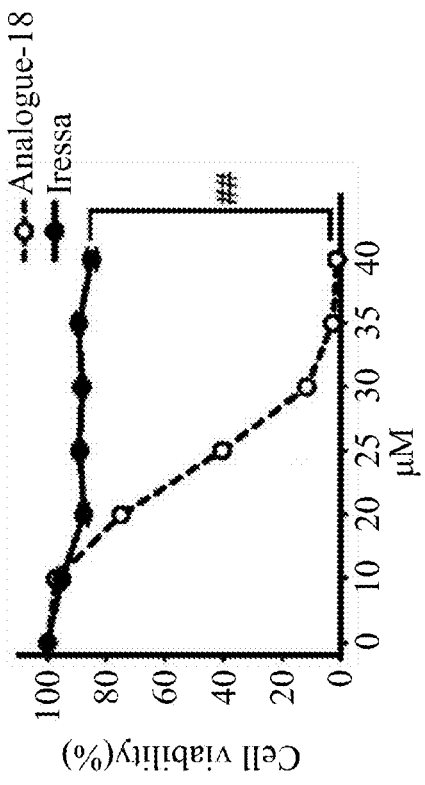
FIGS. 2A-2D show that Analogue-18 is more effective in inducing cell death than Irresa in various human lung cancer cell lines. A variety of human lung cell lines were treated with 0 to 40 µM Irresa or Analogue-18 for 24 hours, respectively. The cell viability was analyzed by MTT assays.
Figure 2C:
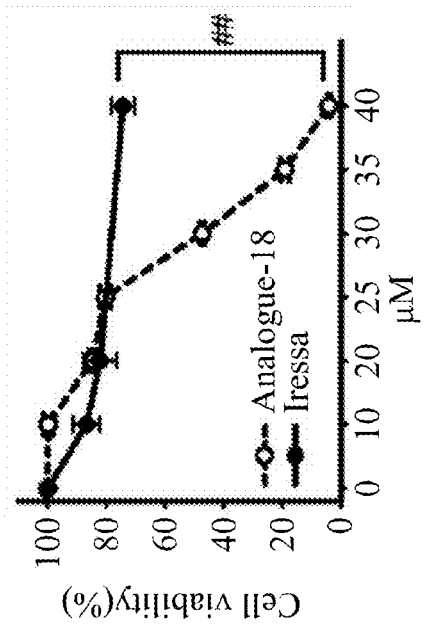
Figure 2B:
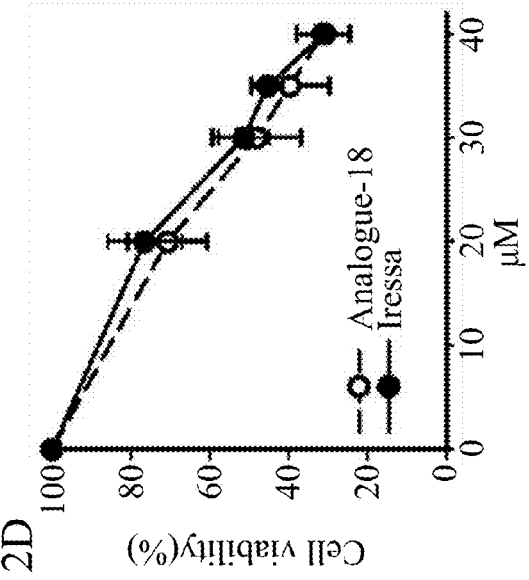
Figure 2D:
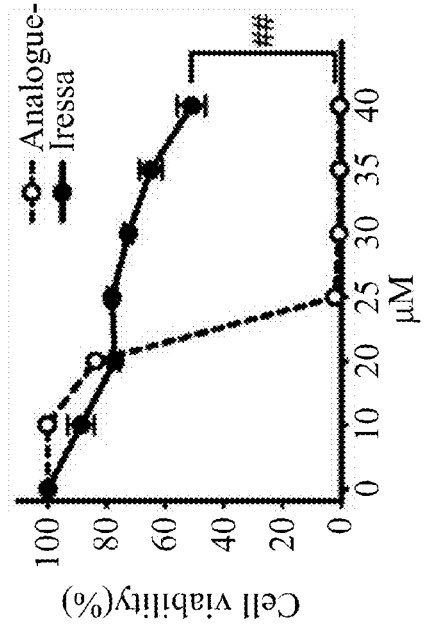

As shown in FIGS. 2A-2C, Analogue-18 is more effective on reducing cell viability than Iressa in A549, H1299 and CL3 cell lines. However, as shown in FIG. 2D, the effect of Analogue-18 on cell viability toward HFL1 cells is similar to that of Iressa. Analogue-18 at 40 µM has more than 99% of toxicity effects in the three lung cancer cell lines, including A549, H1299 and CL3 cell lines, while both Analogue-18 and Iressa keep more than 30% of cell viability in HFL1 cells. These results indicate that Analogue-18 has better toxicity effect on lung cancer cells and it does not cause severe toxicity effect on normal lung cells.

Example 4

Analogue-18 Inhibits EGFR Kinase Activity in Lung Cancer Cells

The present invention determines whether Analogue-18 reduces cell viability of lung cancer cells by inhibiting EGFR protein kinase activity.

Step 1: Examining EGFR Expression in Various Human Lung Cancer Cells.

A549, H1299, CL3 and A431 cell lines (A431, EGFR overexpressed, used as a positive control group) were lysed in the ice-cold cell extract buffer (pH 7.6) containing 0.5 mM DTT, 0.2 mM EDTA, 20 mM HEPES, 2.5 mM $MgCl_2$, 75 mM NaCl, 0.1 mM $Na_3VO_4$, 50 mM NaF, and 0.1% Triton X-100. The protease inhibitors including 1 µg/ml aprotinin, 0.5 µg/ml leupeptin, and 100 µg/ml 4-(2-aminoethyl)benzenesulfonyl fluoride were added to the cell suspensions. The lysates were vibrated for 30 minutes at 4° C. and centrifuged at 10,000 rpm for 10 minutes. The protein concentrations were determined by the BCA protein assay kit (Pierce, Rockford, Ill.). The total cellular protein extracts were prepared, separated on 8-12% sodium dodecyl sulfate-polyacrylamide (hereinafter referred to SDS) gels, and transferred electrophoretically onto polyvinylidene difluoride membranes. The membranes were blocked overnight at 4° C. using blocking buffer (5% non-fat dried milk in solution containing 50 mM Tris/HCl (pH 8.0), 2 mM $CaCl_2$, 80 mM NaCl, 0.05% Tween 20 and 0.02% sodium azide). The membranes were sequentially hybridized with primary antibody and followed with a horseradish peroxidase-conjugated secondary antibody. The protein bands were visualized on the X-ray film using the enhanced chemiluminescence detection system (PerkinElmer Life and Analytical Sciences, Boston, Mass.). Specific antibodies were used for Western Blot analysis for detecting EGFR and phosphor-EGFR (Tyr 1068). To verify equal protein loading and transfer, actin was used as the protein loading control. The gel digitizing software, Un-Scan-It gel (Ver. 5.1, Silk Scientific, Inc., Orem, Utah), was used to analyze the intensity of protein bands on X-ray film.

Figure 3:
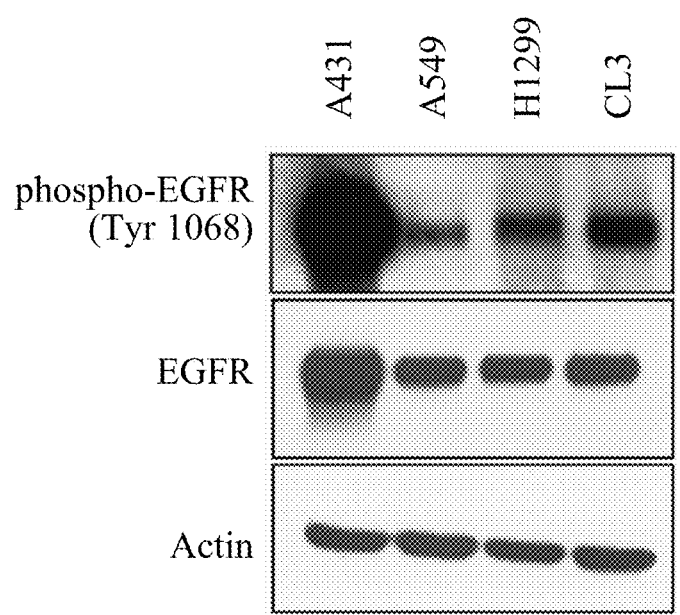
FIG. 3 shows protein expression of EGFR and phosphorylated EGFR (hereinafterafter referred to phosphor-EGFR) in different human lung cancer cells. The total proteins extract from A549 cells, H1299 cells, CL3 cells and A431 human epidermoid carcinoma cell line (EGFR overexpressed, as a positive control group) (hereinafterafter referred to "A431 cells") were subjected to Western blot analysis using anti-EGFR, anti-phosphor-EGFR and anti-actin antibodies. The actin was used as an internal protein control group. The representative Western blot data were shown from one of three independent experiments with similar findings.

As shown in FIG. 3, A549 cells, H1299 cells and CL3 cells express EGFR and phosphor-EGFR (Tyr 1068) which indicate that the lung cancer cells have active EGFR protein kinases.

Step 2: Determining the Inhibition of Analogue-18 to the Activity of EGFR Protein Kinase.

Figure 4A:
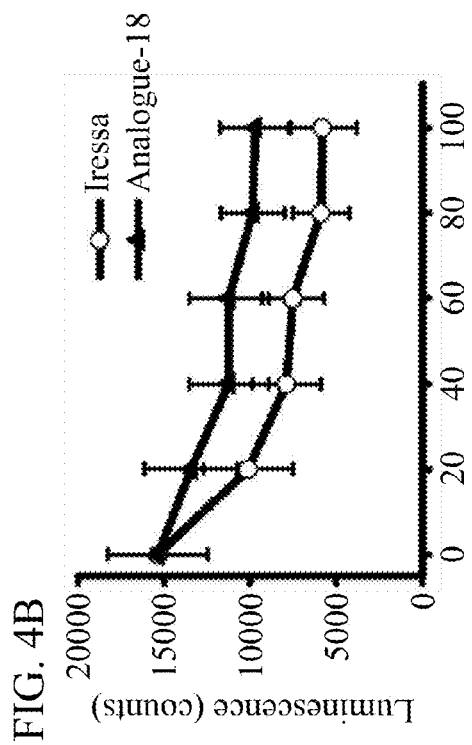
FIGS. 4A-4D show that both of Analogue-18 and Irresa inhibit the protein kinase activity of EGFR.

Activity of the EGFR protein kinases was determined using the ADP-Glo™ Kinase Assay and EGFR Kinase Enzyme Systems (Promega, Madison, Wis.) following manufacturer's protocol. The EGFR protein kinase reactions were performed in Reaction Buffer A (pH 7.5), 2 mM $MnCl_2$ and 2 mM DTT. Briefly, the protocol included the following steps:

(1) Preparing an ATP to ADP conversion standard curve at 50 µM ATP/ADP range. As shown in FIG. 4A, the standard curve is positively correlates with ADP amount.

(2) Adding the following reaction components into a 96-well plate: 5 ng active EGFR, 0.25 µg/µl ($Glu_4$, $Tyr_1$) polypeptide substrate, Reaction Buffer A (40 mM Tris-HCl (pH 7.5), 20 mM $MgCl_2$ and 0.1 mg/mL BSA) containing 20 to 100 nM Analogue-18 or Iressa.

(3) Adding 50 µM ATP to initiate the EGFR protein kinase reactions at 30□ for 15 minutes.

(4) Adding ADP-Glo™ reagent to terminate the EGFR protein kinase reaction and deplete the remaining ATP at room temperature for 40 minutes.

(5) Adding Kinase Detection Reagent to convert ADP to ATP at room temperature for 30 minutes.

(6) Observing and analyzing the luminescence produced during the conversion of ADP to ATP by IVIS system (Xenogen IVIS Spectrum, Caliper Life Sciences) and Luminometer (Modulus Single Tube, Turner Biosystems, Inc., Sunnyvale, Calif.). The conversion curves were used to determine the amount of ADP produced in the presence and absence of substrate. Based on these data, we calculated the specific activity of protein kinase as the nmole of phosphate transferred to the kinase substrates per minute per mg of total protein.

The formula of kinase specific activity: (ADP-ADP (blank)) in nmol/(reaction time in minute)×(enzyme amount in mg).

Figure 4B:
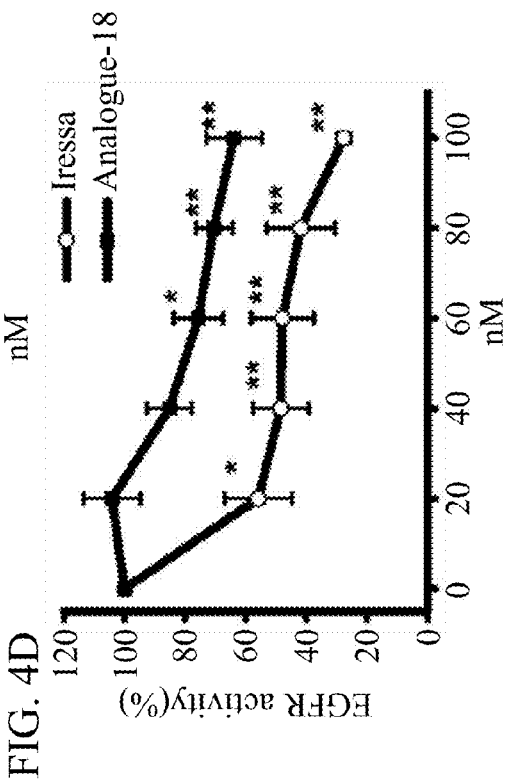
Figure 4C:
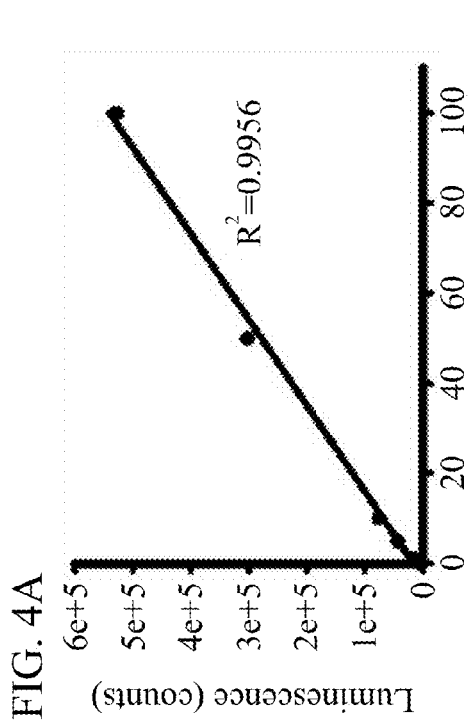
Figure 4D:
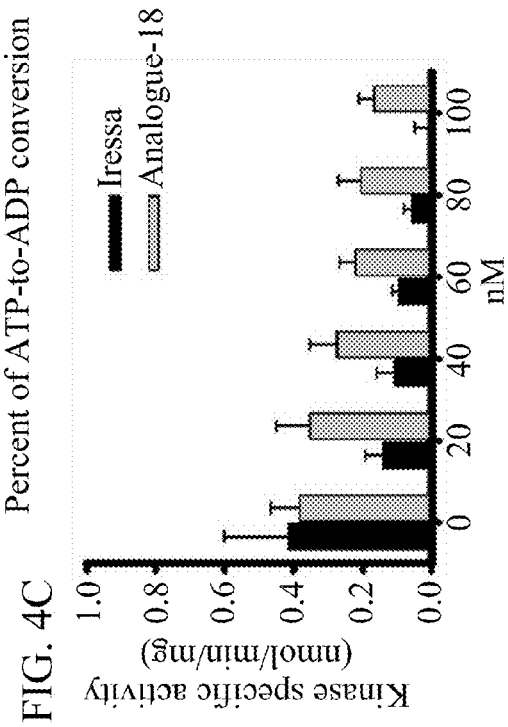

As shown in FIGS. 4B-4D, the results show that treatment with 20 to 100 nM of Analogue-18 or Iressa reduced the luminescence intensities. After quantification, the EGFR protein kinase specific activities (nmol/min/mg) and EGFR protein kinase activity (representative with %, the EGFR protein kinase specific activity treated with 0 nM Analogue-18 or Iressa as 100%) were reduced, when the concentrations of drug treatments increased. In addition, by the IVIS system, the $IC_{50}$ values of Analogue-18 or Iressa are about 130.1 nM and 56.3 nM, respectively. Similarly, by the Luminometer, the $IC_{50}$ values of Analogue-18 and Iressa are about 125.9 nM and 55.4 nM, respectively.

Step 3: Determining the Specific Inhibition of Analogue-18 on EGFR Protein Kinase.

The kinase selectivity profile of Analogue-18 and Iressa on various protein kinases was performed by KinaseProfiler™ service assays (Merck Millipore, Billerica, Mass.). The kinase activity remaining (KAR) value is inversely related to kinase activity. When KAR value equals to 50, it means that the concentration of Analogue-18 or Iressa inducing 50% inhibition of kinase activity is 10 µM.

As shown in Table. 4, both of Analogue-18 and Iressa are potential EGFR protein kinase inhibitors.

TABLE 4

Inhibition of Analogue-18 and Iressa on various protein kinases determined by KinaseProfiler ™ assays.

| Protein kinases | Full name | KAR value of Iressa | KAR value of Analogue-18 |
| --- | --- | --- | --- |
| EGFR | epidermal growth factor receptor | −10 | −2 |
| CHEK1 | checkpoint kinase-1 | 63 | 69 |
| MARK2 | PAR-1Ba | 86 | 84 |
| MKNK2 | MAPK-interacting kinase-2 | 9 | 85 |
| CSNK2A1 | casein kinase-2 | 92 | 76 |
| MAPK14 | stress-activated protein kinase-2a | 20 | 87 |
| STK10 | lymphocyte-oriented kinase | 19 | 43 |
| FGFR1 | fibroblast growth factor receptor-1 | 27 | 82 |
| RET | product of ret proto-oncogene | 30 | 98 |
| LCK | lymphocyte kinase | 9 | 89 |
| SYK | splenic tyrosine kinase | 84 | 87 |
| LIMK1 | LIM motif-containing protein kinase-1 | 76 | 82 |

Example 5

Analogue-18 is More Effective on Inducing Apoptosis than Iressa in Lung Cancer Cells This Example determine whether Analogue-18 reduces cell viability by inducing apoptosis in lung cancer cells and whether Analogue-18 is more effective on inducing apoptosis than Iressa in lung cancer cells.

The levels of apoptosis induced by Analogue-18 and Iressa were determined by Annexin V-propidium iodide (PI) analysis. The Annexin V-PI staining kit (BioVision, Mountain View, Calif.) was used to exam the cells by incubating with fluorescent isothiocyanate (FITC)-conjugated-Annexin V and PI according to the manufacturer's instruction. The cells showed Annexin $V^+/PI^-$ and Annexin $V^+/PI^+$ were indicated at early and late apoptosis, respectively. The cells were cultured in 60-mm Petri dish at a density of $7 \times 10^5$ cells for 16 to 20 hours. After treatment with 0 to 40 μM of Analogue-18 or Iressa for 4 hours, the cells were washed with PBS. The cells were trypsinized and collected by centrifugation at 1500 rpm for 5 minutes. Thereafter, the cells were incubated with 500 μl Annexin V-PI labeling solution (containing 5 μl Annexin V-FITC and 5 μl PI in PBS) at room temperature in the dark for 5 minutes. To avoid cell aggregation, the cell solutions were filtered through a nylon mesh membrane (Becton-Dickinson, San Jose, Calif.). Finally, the samples were analyzed immediately using flow cytometer (FACS Calibur, BD Biosciences, Heidelberg, Germany). The percentage of Annexin V-PI staining cells was quantified from a minimum of 10,000 cells by CellQuest software (BD Biosciences).

Figures 5A, 5B:
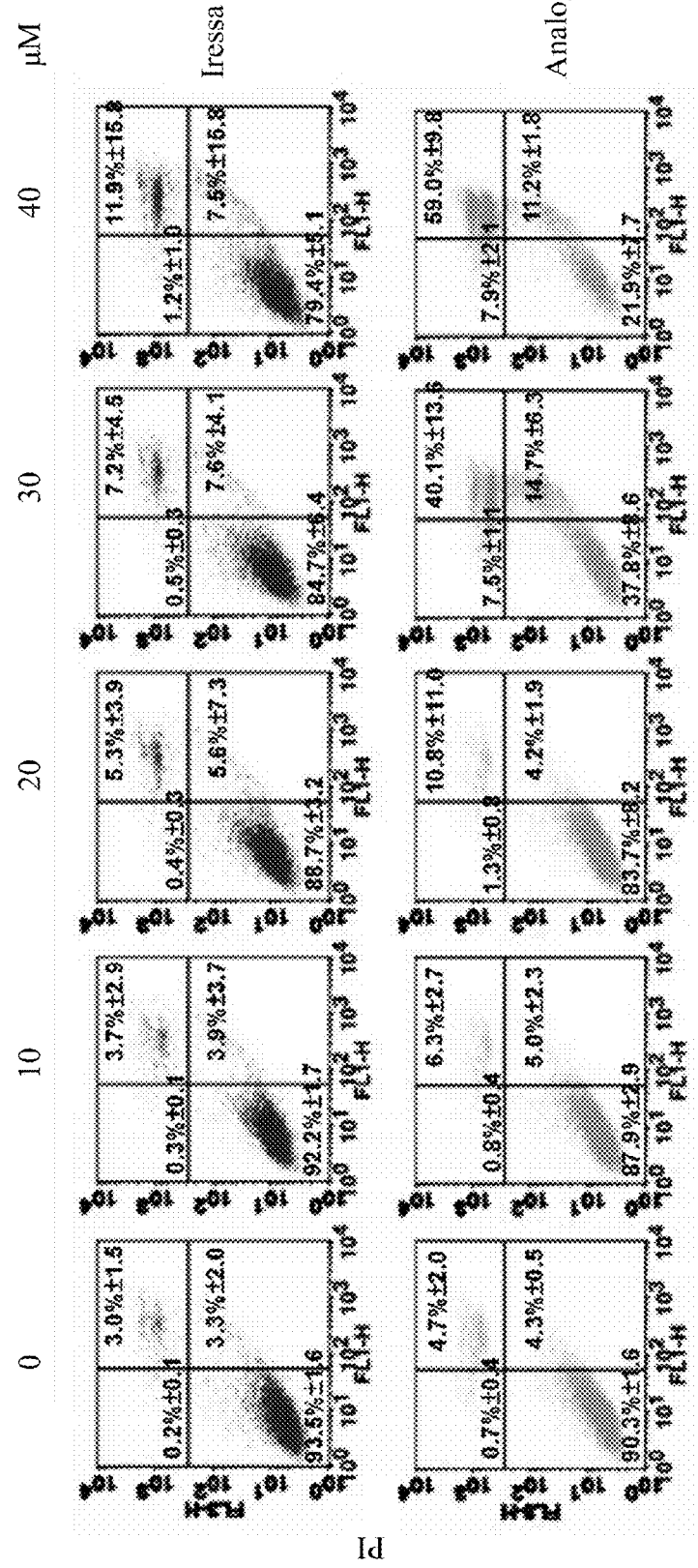
FIGS. 5A and 5B show that Analogue-18 is more effective in inducing an apoptosis than Irresa in human lung cancer cells. A549 cells were treated with 0 to 40 μM of Analogue-18 (FIG. 5A) or Irresa (FIG. 5B) for 24 hours. After treatment, apoptosis was determined by Annexin V-PI (propidium iodise, hereinafter referred to PI) staining using flow cytometry analysis. The cell population of Annexin $V^+/PI^-$ indicated early apoptosis (referred to lower right). The cell population of Annexin $V^+/PI^+$ indicated late apoptosis (referred to upper right). The results were shown from one of three independent experiments with similar findings.
Figure 6A:
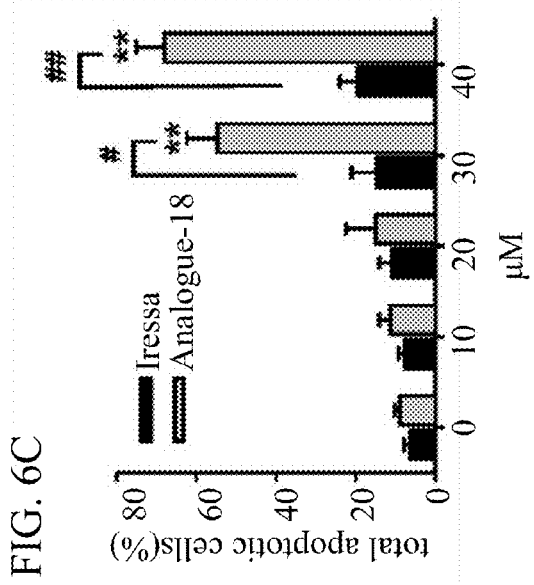
FIGS. 6A-6C show the percentage of (FIG. 6A) early apoptosis, (FIG. 6B) late apoptosis, and (FIG. 6C) total apoptosis quantified by CellQuest software. The bar represents the mean±S.E., *$p<0.05$ and **$p<0.01$ indicate significant differences between the control (without any compound) and the sample treated with Analogue-18. #$p<0.05$ and ##$p<0.01$ indicate significant differences between the sample treated with Irresa and the one treated with Analogue-18.
Figure 6B:
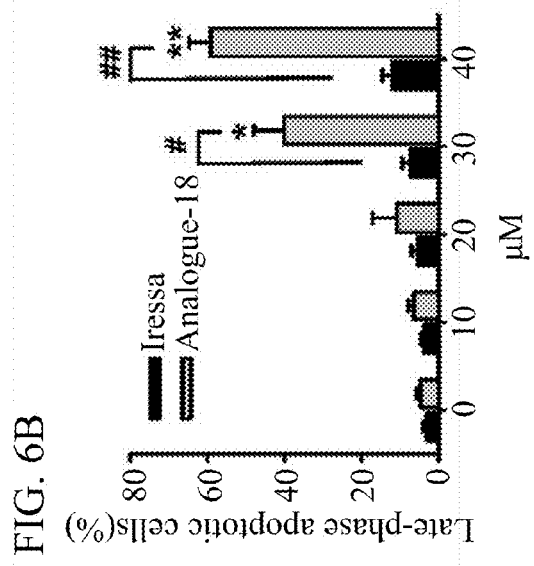
Figure 6C:
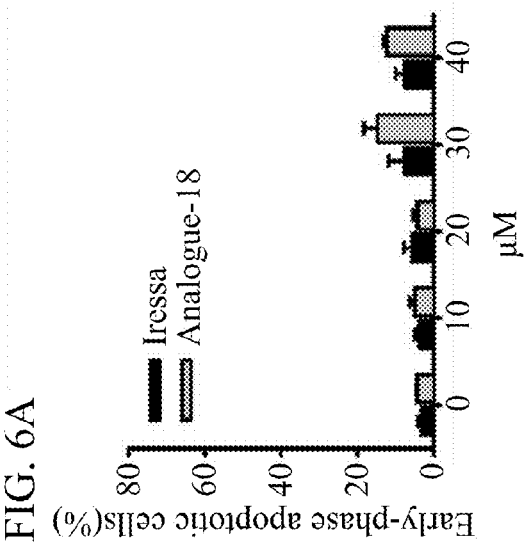

As shown in FIG. 5A, the Annexin $V^+/PI^-$ cells and Annexin $V^+/PI^+$ cells were increased by the following treatment with 10-40 μM Analogue-18 or Iressa for 24 hours, which indicates the number of apoptotic cell was increased. In addition, as shown in FIGS. 6A-C, Analogue-18 induces the average of total apoptosis around 67.9% but Iressa only induces the average of total apoptosis around 19.6%. These results indicate that Analogue-18 induces apoptosis in lung cancer cells more effectively so as to reduce the cell viability.

Example 6

Analogue-18 Inhibits the Growth of Cancer Cells and Increases the Sub-G1 Phase in Lung Cancer Cells The present invention determines whether Analogue-18 inhibits the growth of lung cancer cells by inducing apoptosis in the lung cancer cells and it further determines the effect of Analogue-18 on cell cycle of lung cancer cells.

Step 1: Examining the Inhibition Effect of Analogue-18 on Cell Growth of Lung Cancer Cells A549 cells were plated at a density of $1 \times 10^6$ cells per 60-mm Petri dish in complete medium for 18 hours then treated with 30 μM Analogue-18 or Iressa for 24 hours. The cells were washed with PBS after the treatment. Then the cells were replaced with a fresh RPMI-1640 complete medium in the Petri dish and cultured for 2-6 days. The cell number was calculated with hemocytometer.

Figure 7:
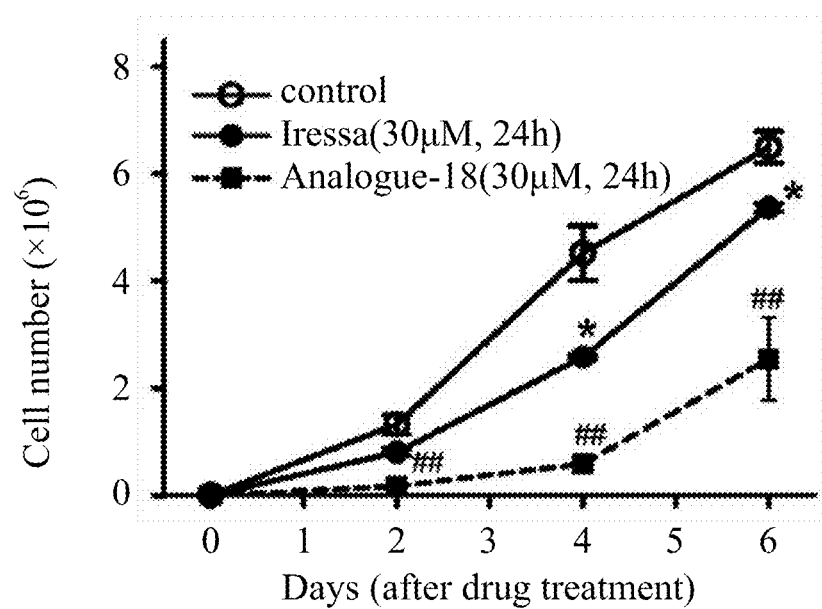
FIG. 7 shows that Analogue-18 is more effective in inhibiting the cell growth and cell cycle of human lung cancer cells than Irresa. A549 cells were plated at a density of $10^6$ cells/p60 in 60 mm Petri dish for 18 hours. Then, the cells were treated with or without 30 μM Analogue-18 or Irresa for 24 hours. After treatment, the cells were incubated for 2 to 6 days before they were counted by hemocytometer. The results were obtained from 3 experiments and the bar represents the mean±S.E. *$p<0.05$ indicates significant difference between the control (without any compound) and the sample treated with Irresa. ##$p<0.01$ indicates significant difference between the control (without any compound) and the sample treated with Analogue-18.
Figures 8A, 8B:
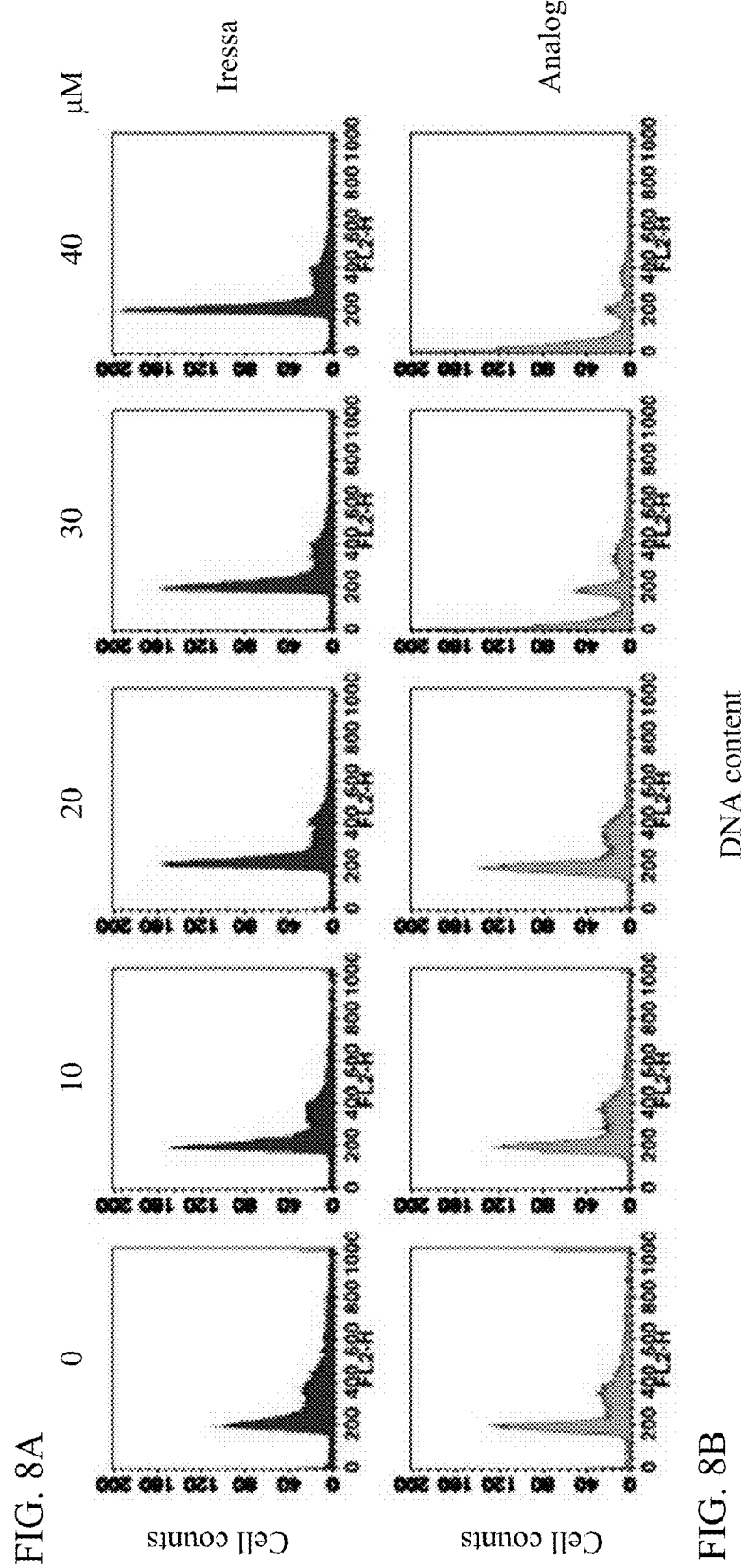
FIGS. 8A and 8B show that A549 cells were treated with 0 to 40 μM of (FIG. 8A) Irresa or (FIG. 8B) Analogue-18 for 24 hours. After treatment, the cells were trypsinized and subjected to flow cytometry analysis. The results were shown from one of three independent experiments with similar findings.
Figure 9A:
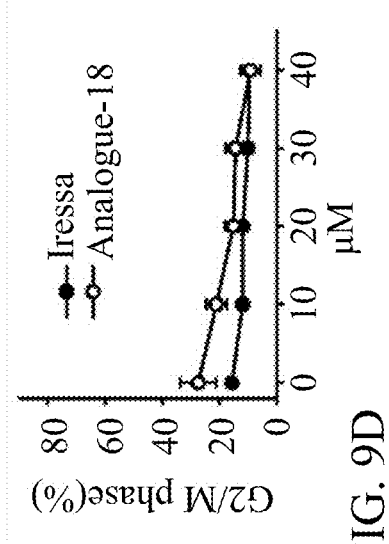
FIGS. 9A-9D show the percentage of (FIG. 9A) G0/G1, (FIG. 9B) S, (FIG. 9C) G2/M and (FIG. 9D) sub-G1 phases quantified by ModFit LT software. The results were obtained from 3 experiments and the bar represents the mean±S.E. *$p<0.05$ and **$p<0.01$ indicate significant differences between control (without any compound) and the sample treated with Irresa or Analogue-18. ##$p<0.01$ indicates significant difference between the sample treated with Irresa and the one treated with Analogue-18.
Figure 9B:
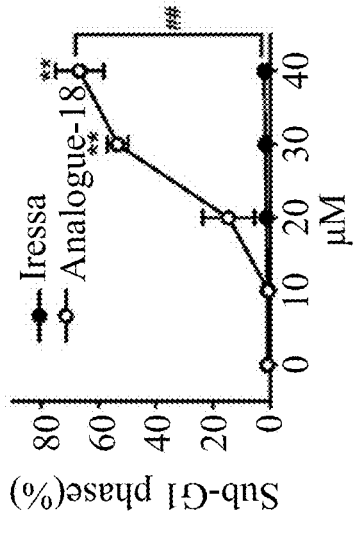
Figure 9C:
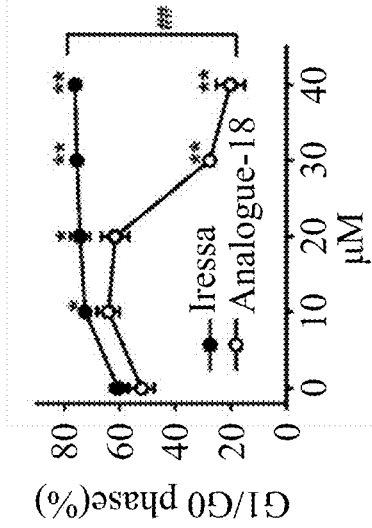
Figure 9D:
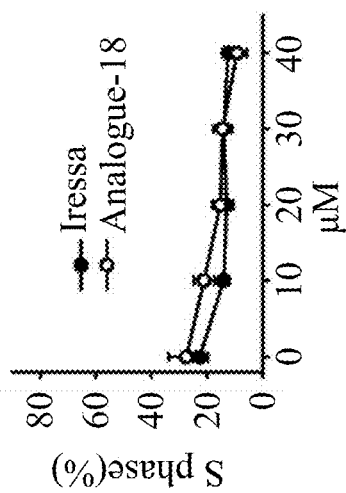
Figure 11A:
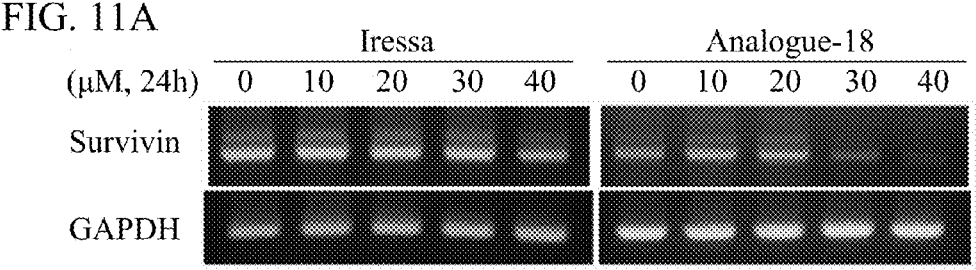
FIGS. 11A-11D show that Analogue-18 is more effective in inhibiting the gene and protein expression of surviving in human lung cancer cells than Irresa.
Figure 11B:
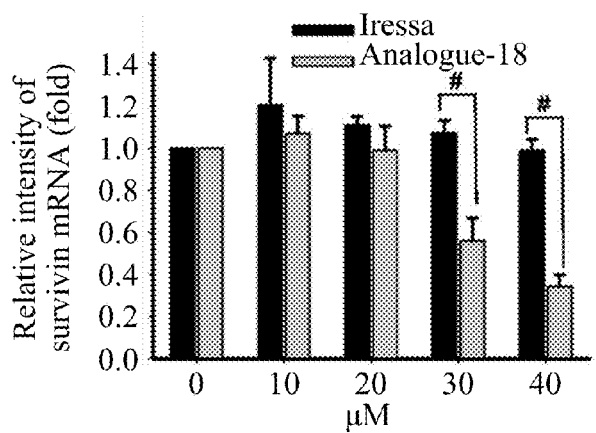
Figure 11C:
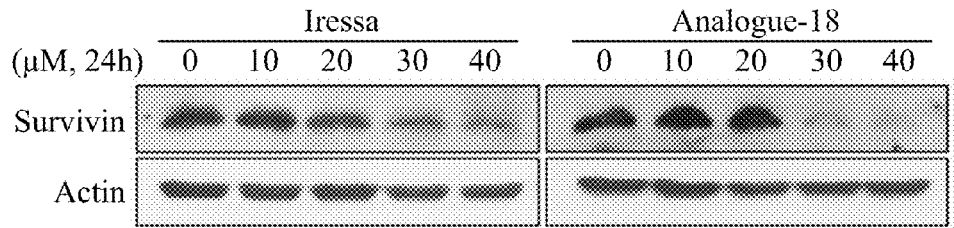
Figure 11D:
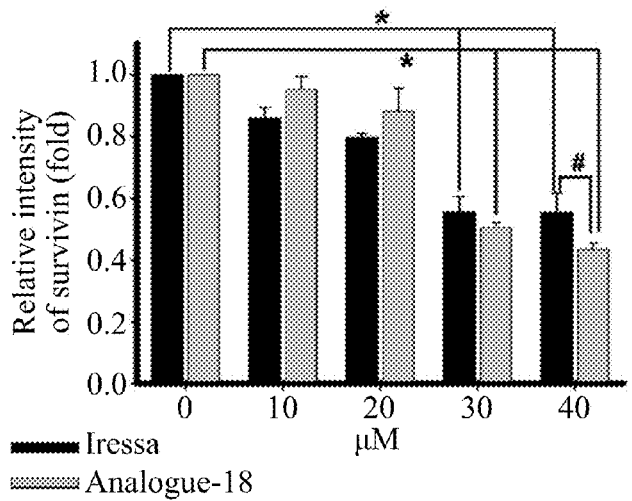

As shown in FIG. 7, both Analogue-18 and Iressa inhibit cell growth of A549 cells, and Analogue-18 is more effective.

Step 2: Examining the Effect of Analogue-18 in Regulation of Cell Cycle Progression in Lung Cancer Cells A549 cells were plated at a density of $7 \times 10^5$ cells per 60-mm Petri dish in complete medium for 16 to 20 hours, and then treated with 0 to 40 μM Analogue-18 or Iressa for 24 hours at 37° C. After the treatment, the cells were collected and fixed with ice-cold 70% ethanol overnight at −20° C. After centrifugation at 1500 rpm for 5 minutes, the pellets were treated with 4 μg/ml PI solution containing 1% Triton X-100 and 50 μg/ml RNase at 37□ for 30 minutes in the dark. To avoid cell aggregation, the cell solutions were filtrated through nylon membrane (Becton-Dickinson, San Jose, Calif.). Subsequently, the samples were analyzed by flow cytometry. For each measurement, 10,000 cells were analyzed for DNA content. The percentage of cell cycle phases was quantified by ModFit LT software (Ver. 2.0, Becton-Dickinson).

As shown in FIGS. 8A and 8B, and FIGS. 9A-9D, Analogue-18 does not significantly alter the fractions of G1, S and G2/M phases in A549 cells. However, it markedly increases the fractions of sub-G1 phase in A549 cells. The average percentage of sub-G1 fractions is elevated to 66.7% by treatment with 40 μM Analogue-18 in A549 cells. Nonetheless, the average percentage of G1 fractions is elevated from 60.5% to 76.1% after treatment with 40 μM Iressa. These results indicate that Analogue-18 does not alter the cell cycle progression in A549 cells. The increase in the fraction of sub-G1 phase indicates the increase of apoptotic cells, namely Analogue-18 induce apoptosis in A549 cells so as to inhibit the cell growth in a more effective way than Iressa.

Example 7

Analogue-18 Induce Activation of Caspase 3 and Cleavage of PARP in Lung Cancer Cells The present invention further determines that Analogue-18 can induce apoptosis in lung cancer cells by activating caspase 3 and cleaving poly ADP ribose polymerase (PARP).

A549 cells were plated at a density of $1 \times 10^6$ cells per 60-mm Petri dish in complete medium for 16 to 20 hours. Then A549 cells were treated with 0 to 40 μM Analogue-18 or Iressa for 24 hours at 37° C. After the treatment, the total proteins were extracted according to Example 4 and were subjected to Western blot analysis using specific antibodies. To verify equal protein loading and transfer, actin was used as the protein loading control.

As shown in FIG. 10A, the active form of caspase 3 was significantly induced following treatment with 10-40 μM Analogue-18 for 24 hours in A549 cells. In addition, Analogue-18 induced the cleaved form of PARP. However, Iressa did not induce any significant change of caspase 3 and PARP. As shown in FIGS. 10B and 10C, Analogue-18 significantly increased the active caspase 3 and the cleaved PARP, so as to induce apoptosis in A549 cells. However, the active caspase 3 and cleaved PARP are not significantly altered following Iressa treatment in A549 cells Example 8

Analogue-18 Inhibits Protein and Gene Expression of Survivin in Lung Cancer Cells The present invention determines Analogue-18 induces apoptosis by inhibiting protein and gene expression of surviving in lung cancer cells.

A549 cells were plated at a density of $1 \times 10^6$ cells per 60-mm Petri dish in complete medium for 16 to 20 hours. Then A549 cells were treated with 0 to 40 μM Analogue-18 or Iressa for 24 hours at 37° C. After the treatment, the total proteins were extracted according to Example 4 and were subjected to Western blot analysis using specific antibodies. To verify equal protein loading and transfer, actin was used as the protein loading control.

In addition, A549 cells were plated at a density of $2 \times 10^6$ cells per 60-mm Petri dish in complete medium for 16 to 20 hours. Then A549 cells were treated with 0 to 40 μM Analogue-18 or Iressa for 24 hours at 37° C. After the treatment, total cellular RNA was purified by ZR RNA MiniPrep™ (Zymo Research, Irvine, Calif.) according to the manufacturer's protocol. RNA concentrations were determined by spectrophotometry. cDNAs were synthesized by SuperScript™ III reverse transcriptase with oligo $(dT)_{12-18}$ primer (Invitrogen). Each reverse transcript was amplified with GAPDH as an internal control. Reverse transcription polymerase chain reaction (RT-PCR) was performed by a DNA thermal cycler (Mastercycler gradient, Hamburg, Germany). The reaction reagents are showed in Table 5 and the primers are showed in Table 6. The conditions of RT-PCR are stated as followed: the initial denaturation was performed at 94° C. for 2 minutes, followed by 30 cycles at 94° C. for 30 seconds, 56° C. for 30 seconds, and 72° C. for 40 seconds; and 72° C. for 5 minutes. The PCR products were visualized on 1.2% agarose gels with ethidium bromide staining under UV transillumination, and photograph was taken by a camera DH27-S3 (Medclub, Taoyuan, Taiwan).

To further determine the effect that Analogue-18 inhibits surviving so as to induce apoptosis. The pCT-GFP2 and pCT-GFP-sur8 were employed for transfection using Lipofectamine™ 2000 (Invitrogen) according to the manufacturer's instructions. The pCT-GFP-sur8 overexpressed surviving, and the pCT-GFP2 only overexpressed green fluorescent protein and was used as a control. A549 cells were plated in 60-mm Petri dish at a density of $2 \times 10^6$ per well for 16 to 20 hours, then were transfected with 20 μg of pCT-GFP-sur8 or pCT-GFP2 in serum-free medium for 8 hours at 37° C. in a $CO_2$ incubator. Then, the equal amount medium with 20% fetal bovine serum (FBS) was added without removing the transfection mixture. And proceed the incubation for additional 24 hours. After transfection, the cells were subjected to cytotoxicity assay according to Example 2 and Western blot analysis according to Example 4.

TABLE 5

Reaction reagents of RT-PCR

| Reagent | Use | Manufacturer |
|---|---|---|
| SuperScript ® III Reverse Transcriptase | Reverse-transcript the RNA template into cDNA. | Invitrogen |
| 2X buffer | For reverse transcriptase functioning. | Invitrogen |
| oligo (dT) 12-18 primer | Hybridize to the poly(A) tail of mRNA. | Invitrogen |
| DNA polymerase | Catalyze polymerization of deoxy ribonucleotide. | Promega |
| dNTP | Materials for DNA replication. | Promega |
| 10X buffer | For DNA polymerase functioning. | Promega |

TABLE 6

Primers used for PCR

| Primer | Sequence |
|---|---|
| Forward primer of survivin | 5'-GGCATGGGTGCCCCGACGTTG-3' |
| Reverse primer of survivin | 5'-CAGAGGCCTCAATCCATGGCA-3' |
| Forward primer of GAPDH | 5'-CGGAGTCAACGGATTTGGTCGTAT-3' |
| Reverse primer of GAPDH | 5'-AGCCTTCTCCATGGTGGTGAAGAC-3' |

As shown in FIGS. 11A-11D, surviving gene expression was significantly inhibited in a concentration-dependent manner in A549 cells after Analogue-18 treatment but no significant change after treatment with Iressa. In addition, both Analogue-18 and Iressa significantly inhibited surviving protein expression. These results show that Analogue-18 significantly inhibits surviving gene expression and induce apoptosis in A549 cells and is more effective than Iressa.

Figure 12A:
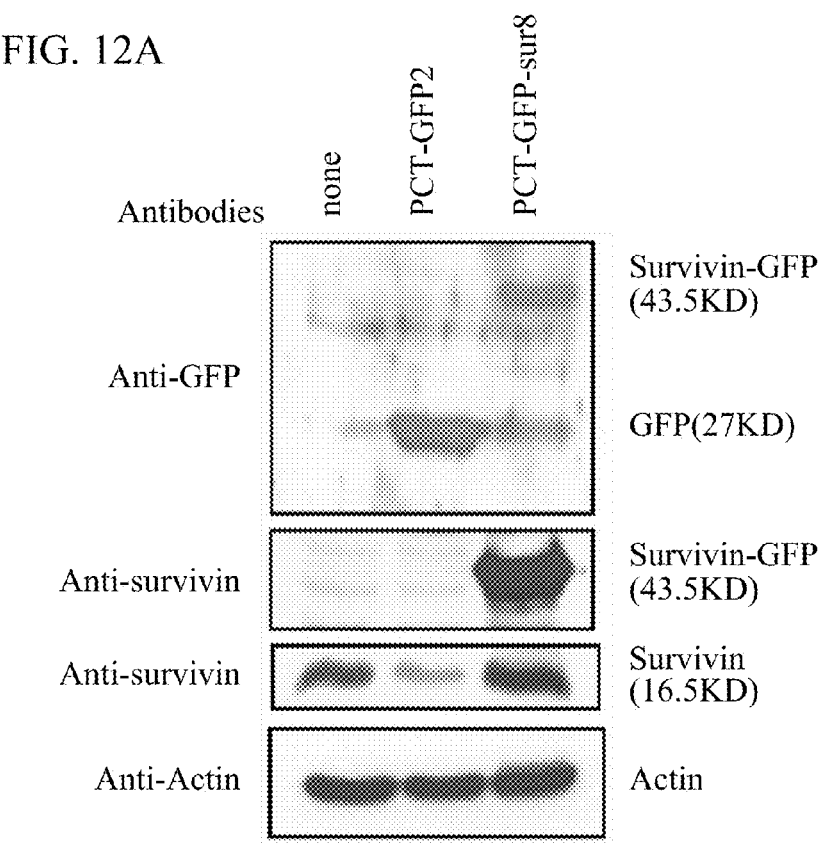
FIGS. 12A and 12B show that overexpression of surviving by transfection with a GFP-surviving expressed vector can inhibit the Analogue-18-induced cell death in lung cancer cells.
Figure 12B:
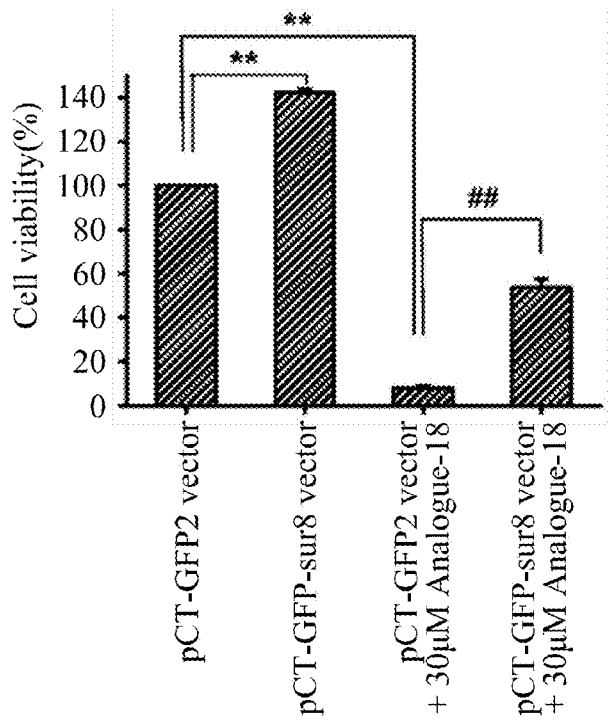

As shown in FIG. 12A, transfection with pCT-GFP-sur8 expressed a surviving-GFP-fusion protein (43.5 kDa) determined by using anti-GFP or anti-surviving antibodies in A549 cells, and pCT-GFP2 only expressed GFP proteins (27 kDa) in A549 cells. As shown in FIG. 12B, overexpression of surviving by pCT-GFP-sur8 vector increased cell viability in A549 cells. Besides, the transfection of pCT-GFP-sur8 was more resistant to the Analogue-18-induced apoptosis than pCT-GFP2. These results indicate that Analogue-18 induces apoptosis by inhibiting surviving in lung cancer cells.

Example 9

Analogue-18 Inhibits Tumorigenesis of Lung Cancer

The present invention determines the effect of Analogue-18 on tumor growth of the xenograft human lung tumors in nude mice. BALB/cAnN.Cg-FoxnInu/CrlNarl mice (3-week-old male) were obtained from BioLASCO (Bio- LASCO Co., Ltd., Taipei, Taiwan). After 2 weeks for environmental adaption, the mice were used for human lung cancer cell inoculation. Solid A549 flank tumors were established by subcutaneous injection of 2×10⁶ cells. After 10 days, the mice bearing A549 human lung xenograft tumors were injected with 100 μl corn oil (control) or 30 mg/kg Analogue-18 for three times every 4 days. The tumor size of the mice was measured by a digital caliper every 4 days and calculated by the following formula: (length)×(width)²×0.5. The xenograft tumors were harvested from scarified mice. The tumors were homogenized and the total lysate were subjected to Western blot analysis according to Example 4.

Figure 13A:
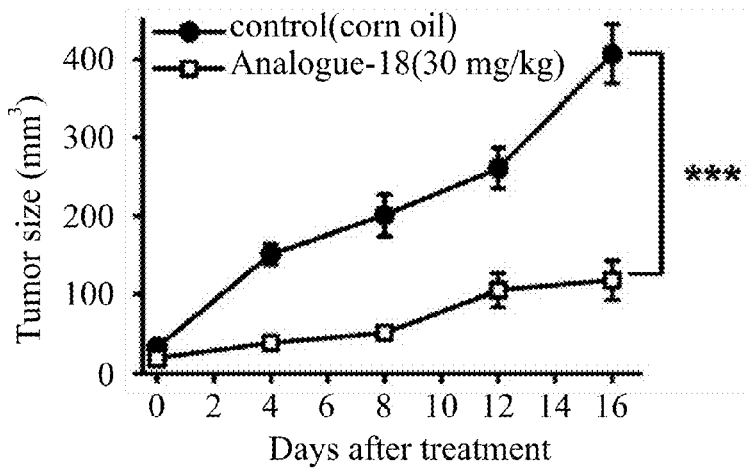
FIGS. 13A-13C show that Analogue-18 inhibits tumor size and surviving protein expression in the xenograft human lung tumors in nude mice.
Figure 13B:
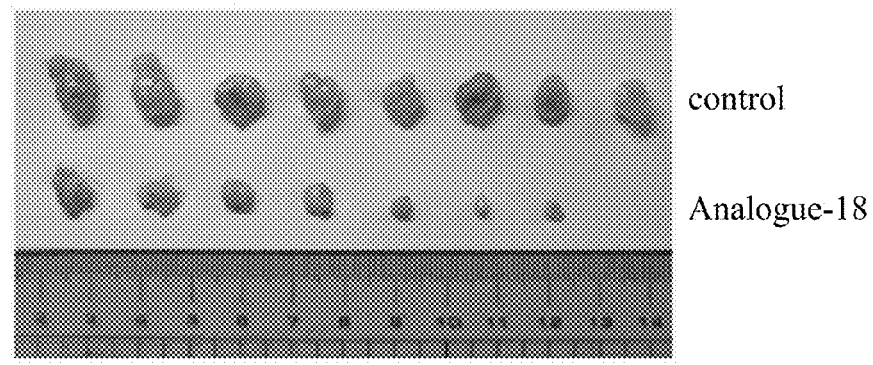
Figure 13C:
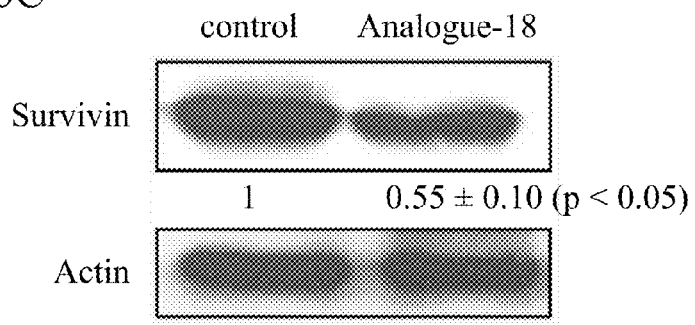

As shown in FIGS. 13A and 13B, the tumor sizes were significantly decreased in the Analogue-18 groups when comparing with the control groups. The average tumor size was 406.52 mm³ in the control groups after inoculation for 16 days, but treatment with Analogue-18 reduced average tumor size to 118.19 mm³. Besides, as shown in FIG. 13C, the surviving protein levels of xenograft tumors were significantly reduced about half amount in the Analogue-18 groups. These results indicate that Analogue-18 can inhibit tumorigenesis in the xenograft human lung tumors of nude mice by inhibiting surviving expression.

The invention claimed is:

1. A compound of Formula (I) and a salt thereof,

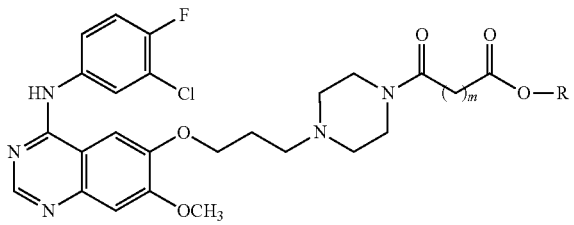

wherein, m is an integer of 2 to 7, and R is independently at least one selected from the group consisting of hydrogen and $C_1$-$C_{20}$ alkyl.

2. The compound of claim 1, wherein m is 2 and R is $C_1$-$C_{13}$ alkyl.

3. A pharmaceutical composition, comprising the compound of claim 1 and a pharmaceutically acceptable carrier.

4. A method for treating a cancer in a subject, comprising a step of administrating an effective amount of the pharmaceutical composition of claim 3 to the subject, wherein the cancer is at least one selected from the group consisting of lung cancer, rectal cancer and bladder cancer.

5. The method of claim 4, wherein the pharmaceutical composition treats the cancer by suppressing the activity of EGFR protein kinase.

6. The method of claim 4, wherein the pharmaceutical composition treats the cancer by promoting an apoptosis of a cancer cell of the cancer and inhibiting a growth of the cancer cell.

* * * * *